US012721887B2

(12) United States Patent
Hahn et al.

(10) Patent No.: US 12,721,887 B2
(45) Date of Patent: Sep. 1, 2026

(54) VACCINE COMPOSITION COMPRISING PLANT-EXPRESSED RECOMBINANT ZIKA VIRUS ENVELOPE PROTEIN AND PREPARATION METHOD THEREFOR

(71) Applicants: BIOAPPLICATIONS INC., Gyeongsangbuk-do (KR); INNOVAC CORPORATION, Gangwon-do (KR)

(72) Inventors: Tae-Wook Hahn, Seoul (KR); Minna Shin, Gangwon-do (KR); Eun-Ju Sohn, Gyeongsangbuk-do (KR); Hyangju Kang, Gyeongsangbuk-do (KR)

(73) Assignees: BIOAPPLICATIONS INC., Gyeongsangbuk-do (KR); INNOVAC CORPORATION, Gangwon-do (KR)

( * ) Notice: Subject to any disclaimer, the term of this patent is extended or adjusted under 35 U.S.C. 154(b) by 628 days.

(21) Appl. No.: 18/041,703

(22) PCT Filed: Aug. 11, 2021

(86) PCT No.: PCT/KR2021/010650

§ 371 (c)(1),
(2) Date: Feb. 15, 2023

(87) PCT Pub. No.: WO2022/039438

PCT Pub. Date: Feb. 24, 2022

(65) Prior Publication Data

US 2023/0293665 A1 Sep. 21, 2023

(30) Foreign Application Priority Data

Aug. 18, 2020 (KR) ........................ 10-2020-0103211

(51) Int. Cl.
*A61K 39/145* (2006.01)
*A61K 39/00* (2006.01)
*A61P 37/04* (2006.01)

(52) U.S. Cl.
CPC ............ *A61K 39/145* (2013.01); *A61K 39/00* (2013.01); *A61P 37/04* (2018.01); *A61K 2039/55505* (2013.01); *A61K 2039/55572* (2013.01)

(58) Field of Classification Search
None
See application file for complete search history.

(56) References Cited

U.S. PATENT DOCUMENTS

| | | | | |
|---|---|---|---|---|
| 8,211,852 B2 * | 7/2012 | Karin | ...................... | A61P 19/02 530/402 |
| 9,833,505 B1 * | 12/2017 | Anderson | ............... | A61P 31/14 |
| 11,723,967 B2 * | 8/2023 | Petsch | ................ | A61K 47/6455 424/186.1 |
| 2002/0078472 A1 * | 6/2002 | Christou | ............ | C12N 15/8257 800/278 |
| 2014/0127749 A1 * | 5/2014 | Mason | .................. | C07K 16/10 435/320.1 |
| 2019/0298818 A1 | 10/2019 | Kinney | | |

FOREIGN PATENT DOCUMENTS

| | | |
|---|---|---|
| KR | 20200033037 | 3/2020 |
| KR | 102128453 | 7/2020 |
| KR | 102148265 | 8/2020 |
| KR | 20200093723 | 8/2020 |
| WO | 2010129033 | 11/2010 |

OTHER PUBLICATIONS

Anonymous, "Fc IgG1 heavy chain constant region, partial [Homo sapiens]", Protein, (Jul. 25, 2016), Database accession No. AEV43323.1, URL: NCBI, XP055499927.

Wang Xinyi, Tai Wanbo, Zhang Xiaolu, Zhou Yusen, Du Lanying, Shen Chuanlai, "Effects of Adjuvants on the Immunogenicity and Efficacy of a Zika Virus Envelope Domain III Subunit Vaccine", Vaccines, (Oct. 27, 2019), vol. 7, No. 4, doi:10.3390/vaccines7040161, XP055901580.

* cited by examiner

*Primary Examiner* — Agnieszka Boesen
(74) *Attorney, Agent, or Firm* — Riverside Law LLP

(57) ABSTRACT

The present invention relates to a vaccine composition including, as active ingredients, a recombinant Zika virus envelope protein including an amino acid sequence of SEQ ID NO: 1, and an adjuvant selected from alum, monophosphoryl lipid A (MPL), or a combination thereof, a recombinant vector for producing the recombinant Zika virus envelope protein in a plant, a transformant transformed with the vector, and a method for producing the recombinant Zika virus envelope protein.

6 Claims, 30 Drawing Sheets

Specification includes a Sequence Listing.

B. Expression cassette of Zika:Env

Zika:Env
M
2 µg
1 µg
0.5 µg
180
100
75
63
48
35
28

Zika:Env1
Zika:Env
100 nm
50 nm
100 nm
50 nm

Figure 6A
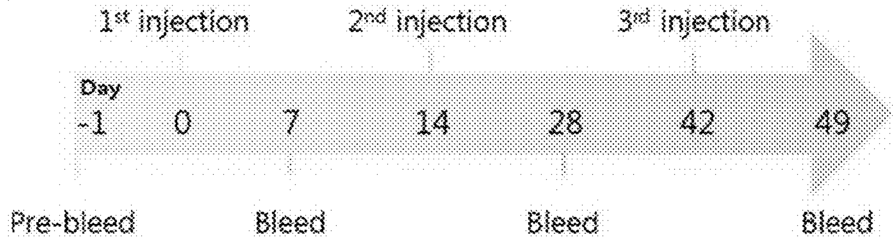
Figure 6B
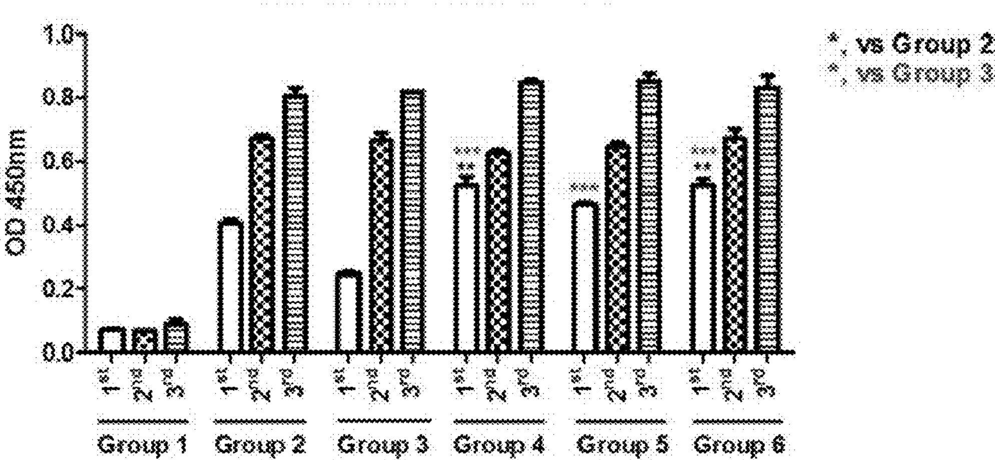
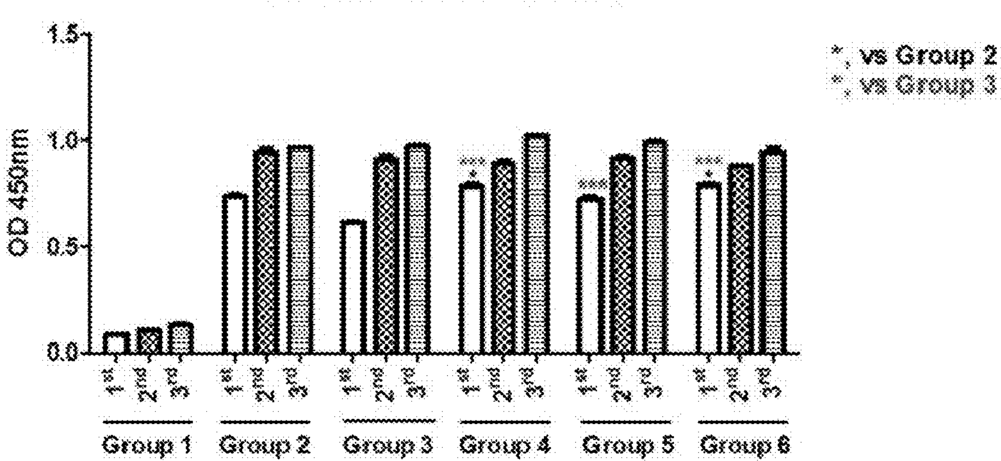
Figure 6

Figure 17A
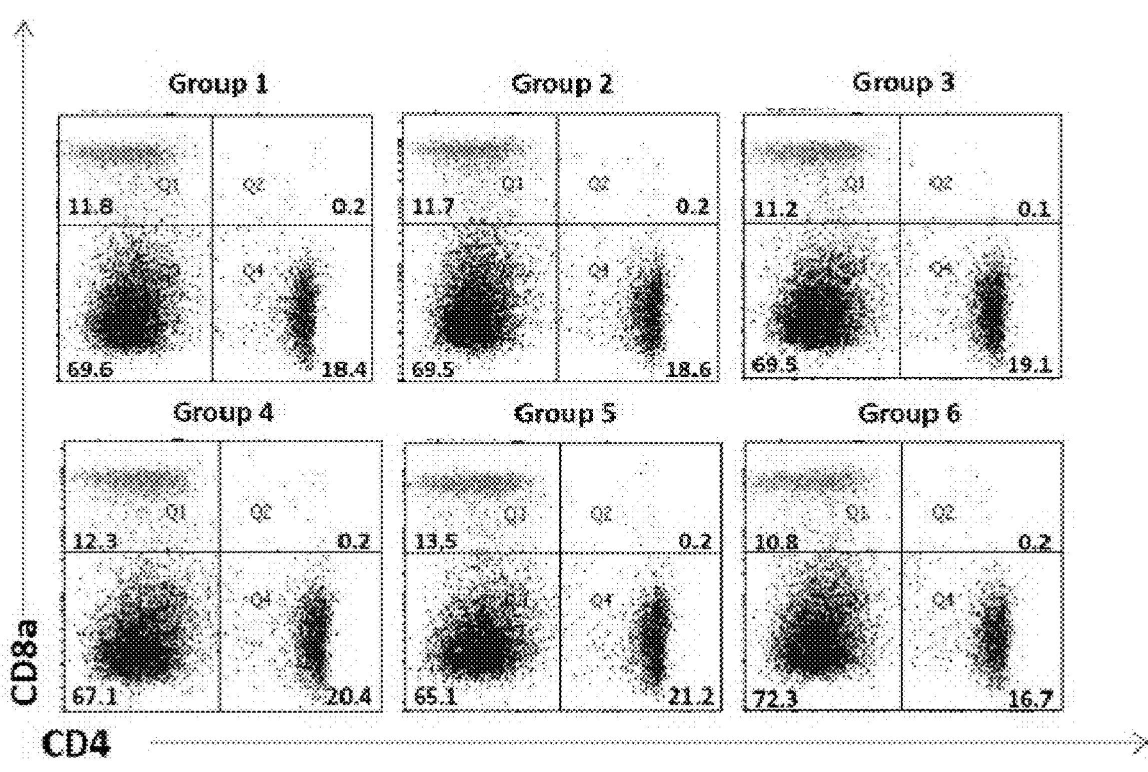
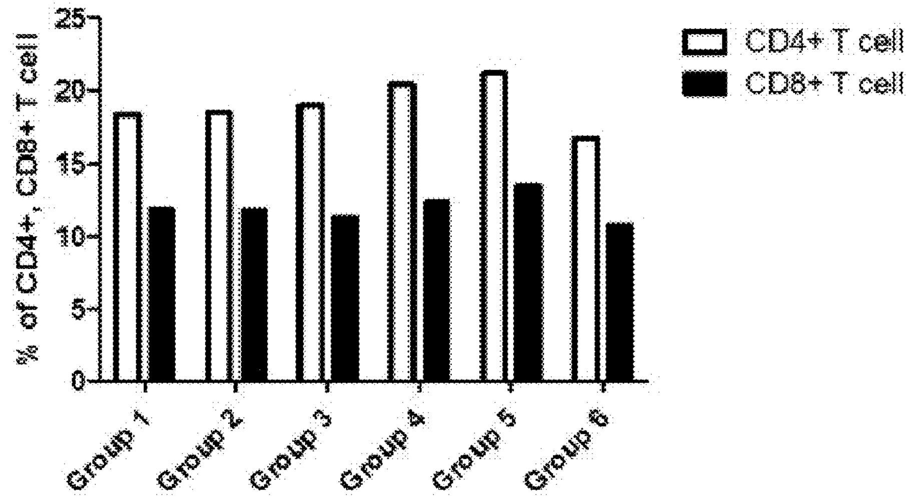
Figure 17

Figure 17B
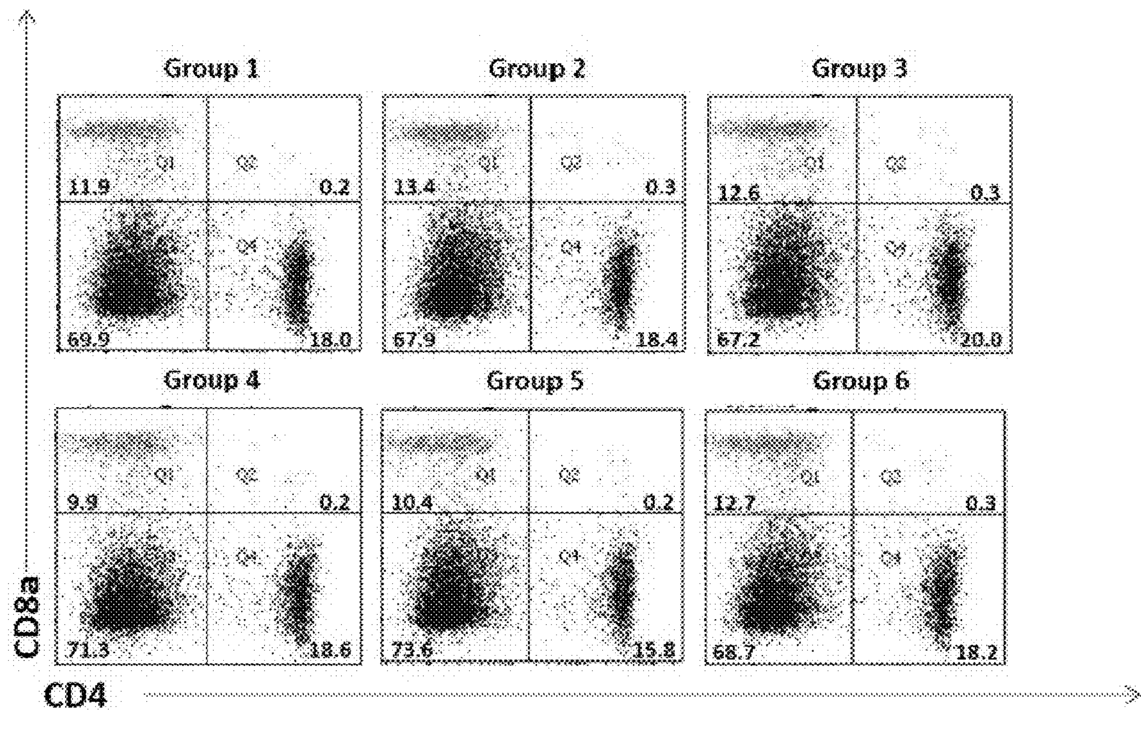
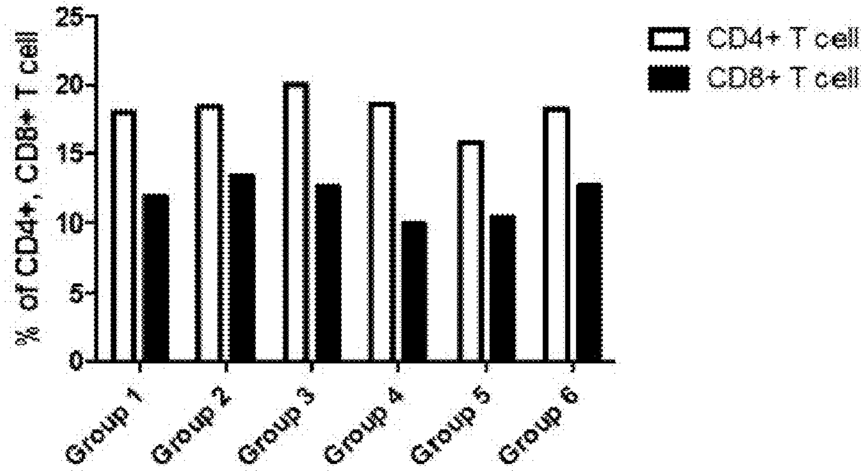
Figure 17 Cont.

Figure 18A
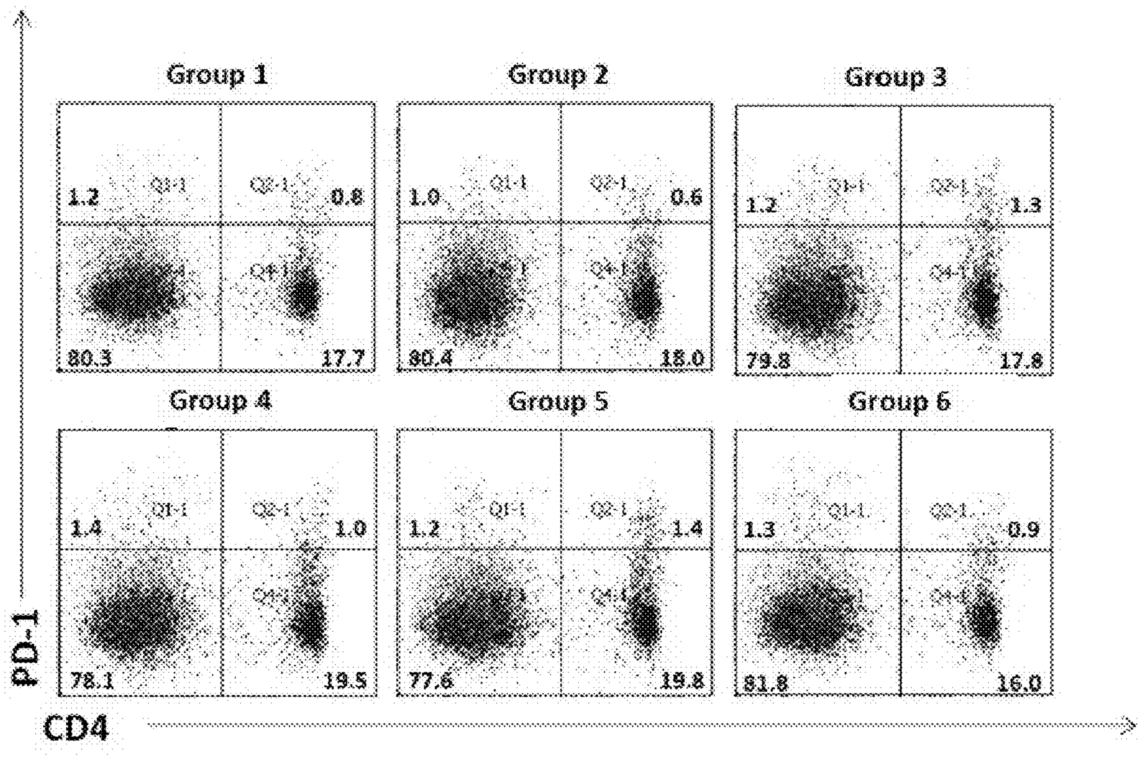
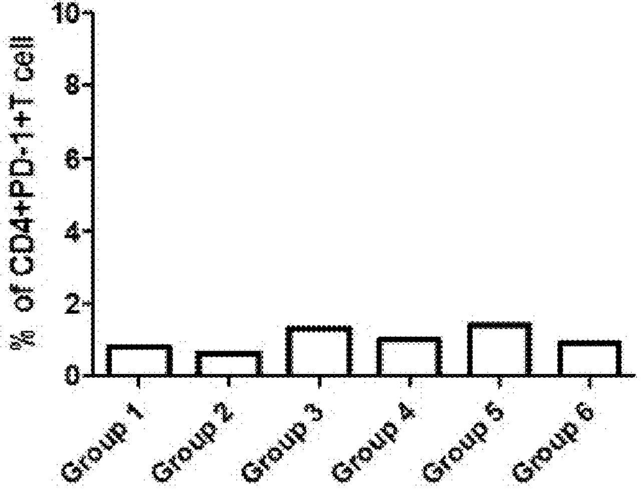
Figure 18

Figure 18C
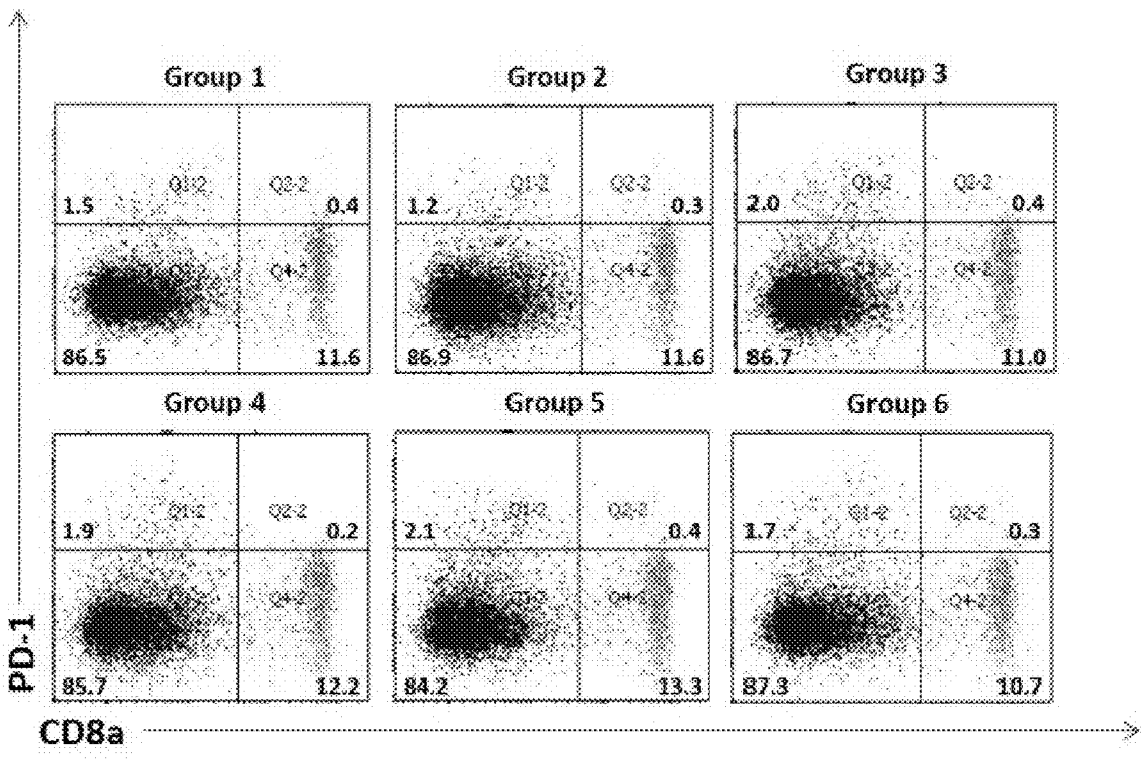
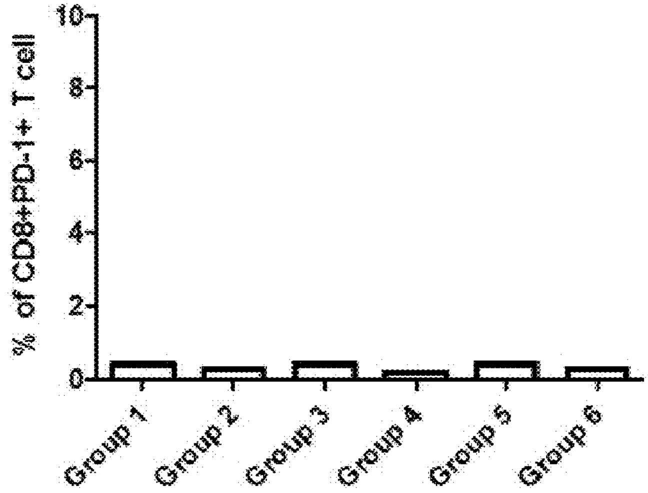
Figure 18 Cont.

Figure 18D
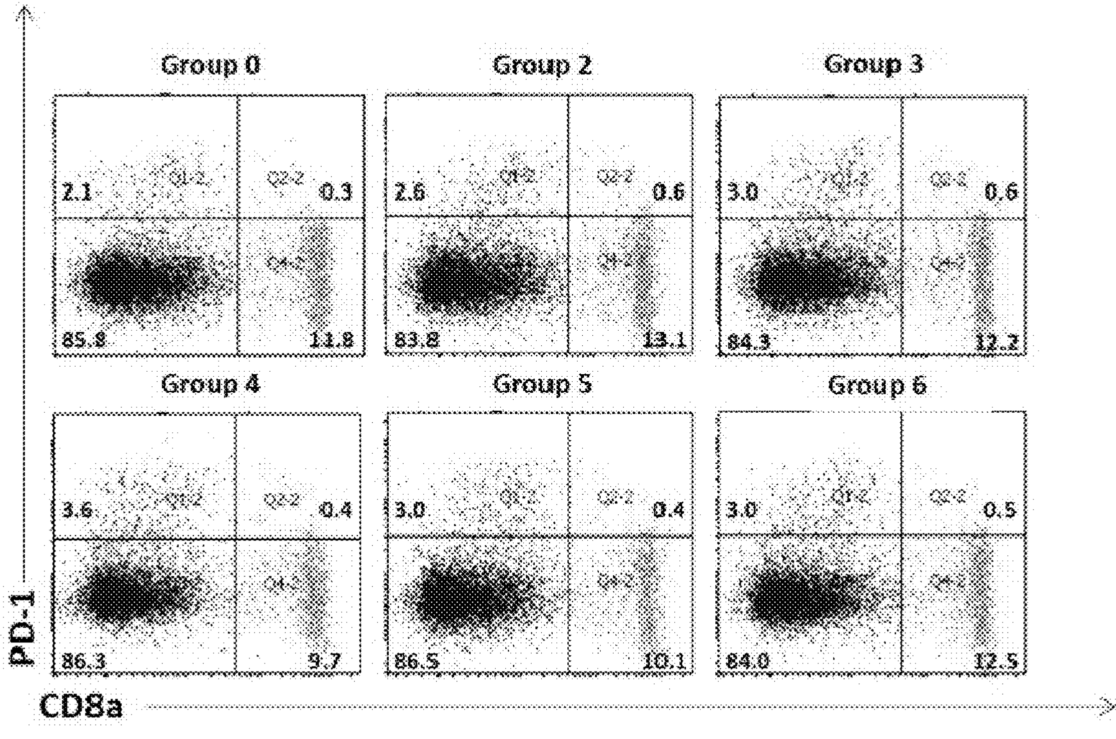
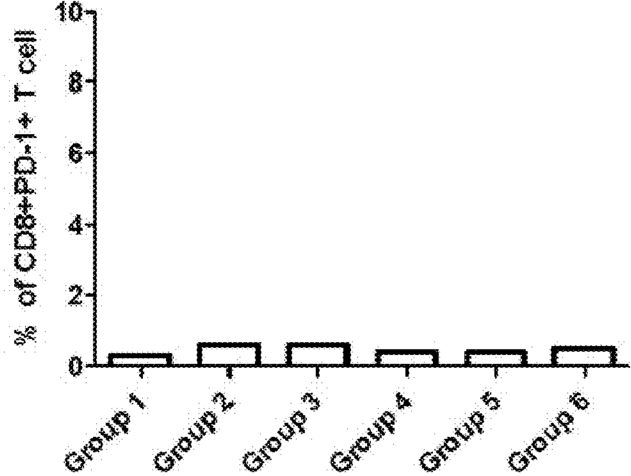
Figure 18 Cont.

Figure 19A
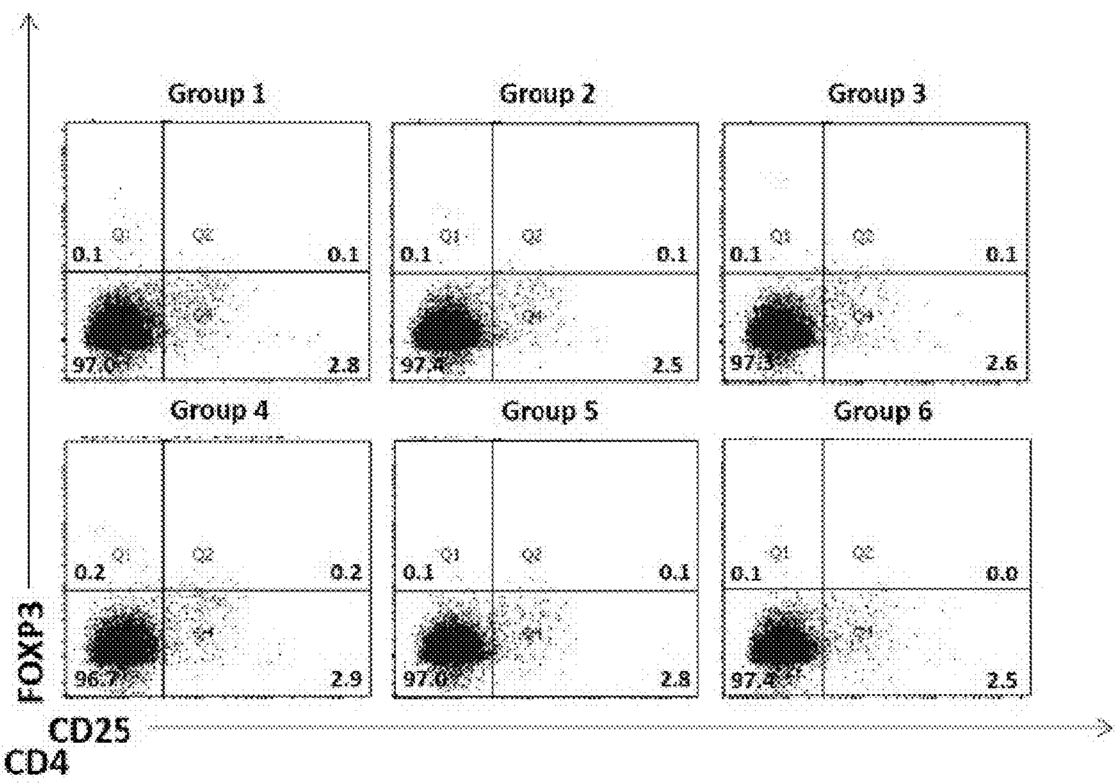
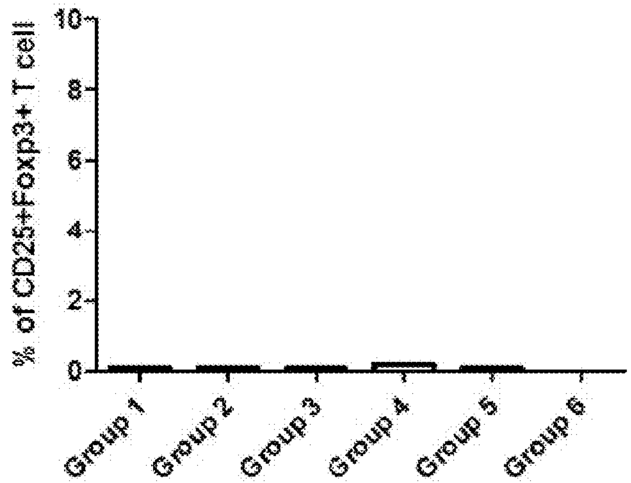
Figure 19

Figure 20B
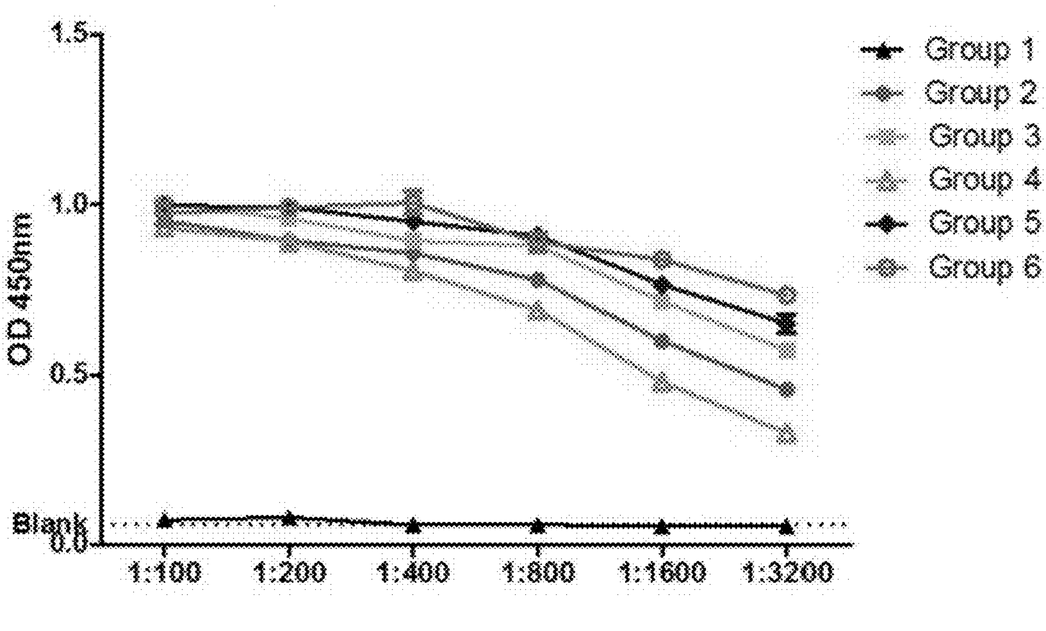
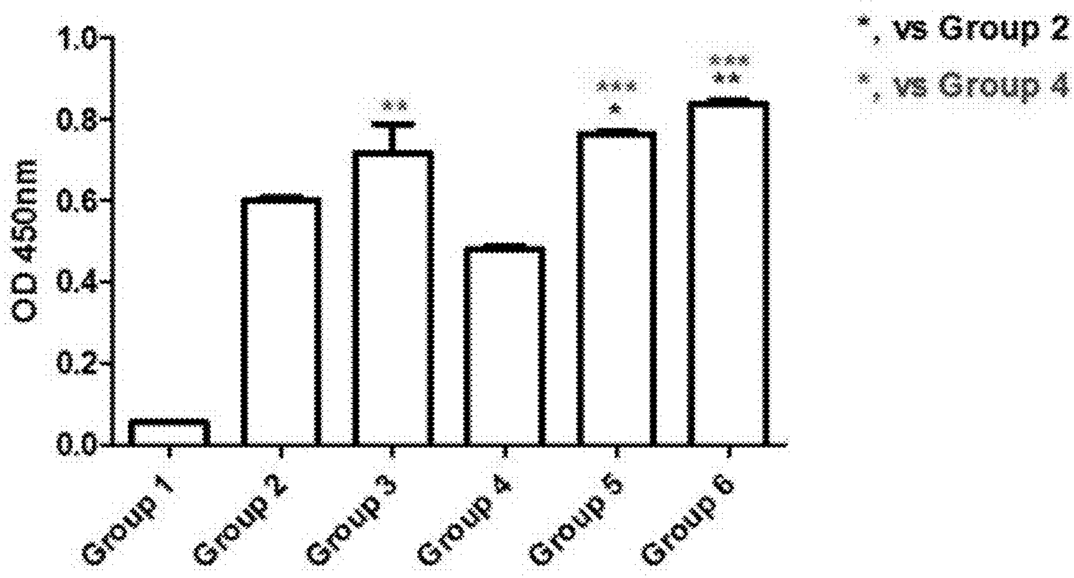
Figure 20 Cont.

A

B

C

Figure 24A
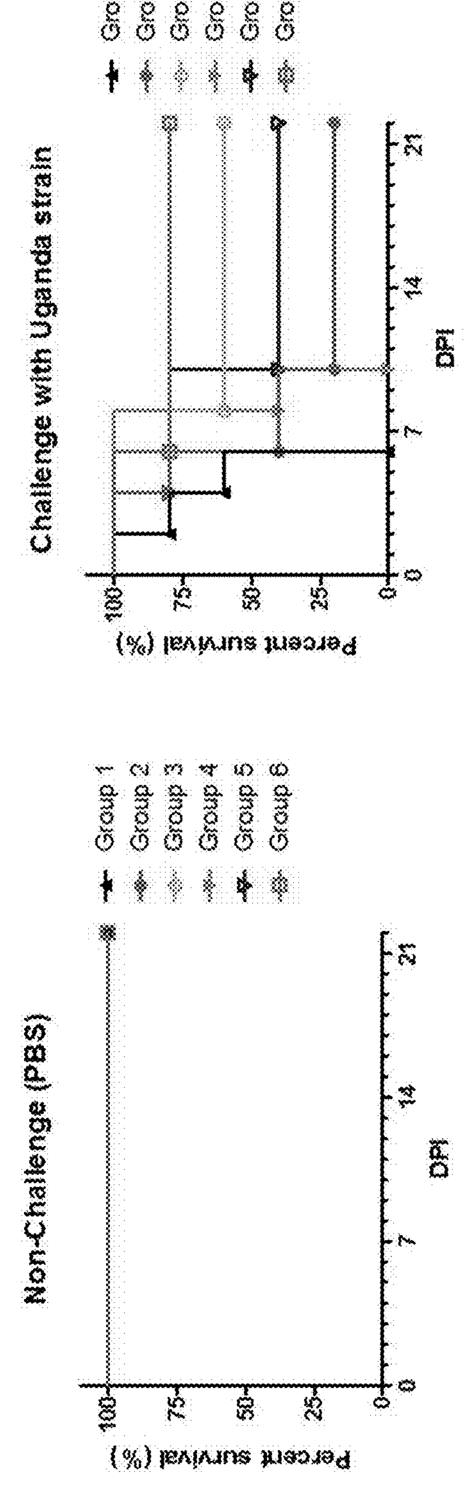
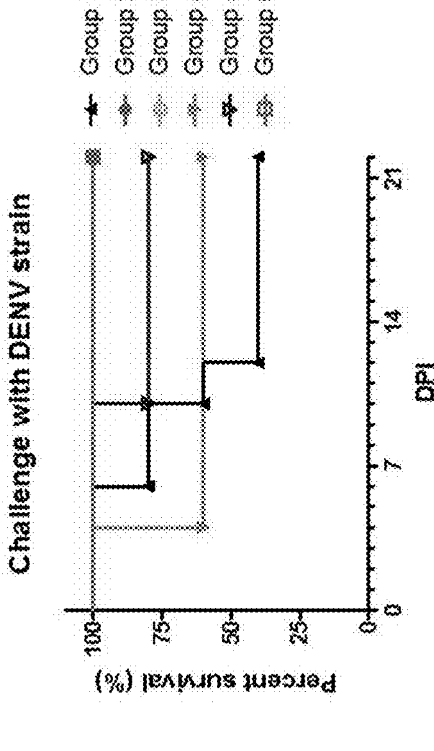
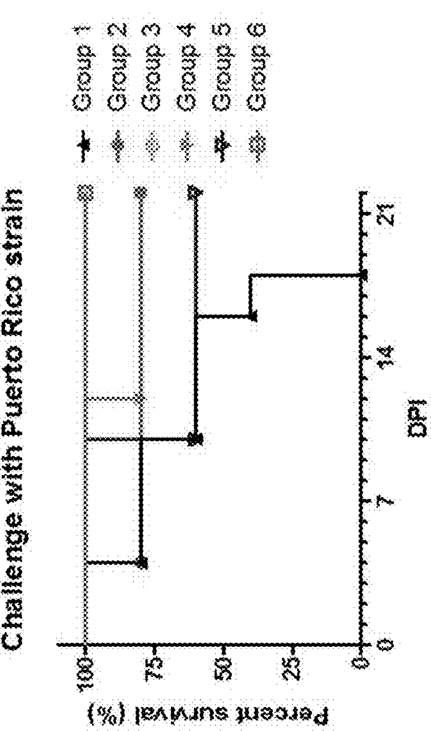
Figure 24

SEQUENCE LISTING

```
<160> NUMBER OF SEQ ID NOS: 13

<210> SEQ ID NO 1
<211> LENGTH: 454
<212> TYPE: PRT
<213> ORGANISM: Artificial Sequence
<220> FEATURE:
<223> OTHER INFORMATION: Amino acid sequence of Zika Env (Zika envelope
      protein ectodomain)

<400> SEQUENCE: 1

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60
```

```
Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Arg Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys
    450
```

<210> SEQ ID NO 2
<211> LENGTH: 1362

<212> TYPE: DNA
<213> ORGANISM: Artificial Sequence
<220> FEATURE:
<223> OTHER INFORMATION: DNA sequence of Zika Env (Zika envelope protein ectodomain)

<400> SEQUENCE: 2

```
atacgatgta ttggtgtttc aaatagggat tttgttgaag gcatgagtgg agggacatgg     60

gtggacgttg tattggagca cggcggttgc gtaaccgtga tggcccaaga taagccaact    120

gttgacattg aactggtcac gactactgtg tcaaatatgg ctgaagtgcg gagctattgt    180

tatgaagcat ctattagtga tatggctagt gattcaagat gtcctacaca gggagaagca    240

tatctggata agcagtccga tacacaatat gtatgcaaac gtactcttgt tgataggggt    300

tggggtaacg gttgcggatt attcggcaag ggttccttgg ttacttgtgc taaattcgcg    360

tgtagcaaaa agatgacagg taagtcgata cagcctgaga atcttgagta ccgcatcatg    420

ttgtctgttc atggtagtca acattctggg atgatcgtca atgacactgg gcatgagact    480

gatgaaaaca gagcaaaggt tgagattact cccaattcac caagggctga agctactctc    540

ggaggatttg gttctttagg attggattgc gagccgagaa ctggactaga tttttctgat    600

ctttactacc ttactatgaa taacaaacat tggctcgttc acaaagaatg gtttcacgac    660

attccacttc cttggcatgc cggagcagac actggtactc ctcattggaa taacaaagag    720

gctctggtcg aatttaagga cgctcacgca aaaagacaaa cagttgtggt tttaggtagc    780

caggaggggg cagttcatac ggctttggca ggtgccttgg aagctgaaat ggatggtgcc    840

aagggtcgat tgtccagtgg tcacttgaag tgtagattga agatggataa acttcgtctt    900

aagggggtgt catattctct gtgcactgct gcttttactt tcacaaaaat accggcagaa    960

acgttacatg gtaccgtgac agtcgaggtt caatatgctg gaactgatgg gccttgtaag   1020

gtaccagccc agatggctgt cgatatgcaa accttaacac cagttggaag acttataact   1080

gctaatcccg ttattacaga gtctactgaa aattctaaaa tgatgctaga gcttgatcct   1140

ccatttggag actcttacat tgtgattgga gttggtgaaa aaaagattac tcatcattgg   1200

cataggtctg gtagtacaat cggtaaagca tttgaagcta ccgtaagggg cgcgagaaga   1260

atggctgttc ttggagatac agcttgggat tttggatcag taggtggagc cctcaactca   1320

ctcggaaaag gtattcacca gatcttcggt gcagcattca ag                      1362
```

<210> SEQ ID NO 3
<211> LENGTH: 251
<212> TYPE: DNA
<213> ORGANISM: Artificial Sequence
<220> FEATURE:
<223> OTHER INFORMATION: DNA sequence of NB (new chaperone binding protein)

<400> SEQUENCE: 3

```
atggctcgct cgtttggagc taacagtacc gttgtgttgg cgatcatctt cttcggtgag     60

tgattttccg atcttcttct ccgatttaga tctcctctac attgttgctt aatctcagaa    120

cctttttttcg ttgttcctgg atctgaatgt gtttgtttgc aatttcacga tcttaaaagg    180

ttagatctcg attggtattg acgattggaa tctttacgat ttcaggatgt ttatttgcgt    240

tgtcctctgc a                                                         251
```

<210> SEQ ID NO 4
<211> LENGTH: 9
<212> TYPE: PRT

```
<213> ORGANISM: Artificial Sequence
<220> FEATURE:
<223> OTHER INFORMATION: Amino acid sequence of H-HDEL

<400> SEQUENCE: 4

His His His His His His Asp Glu Leu
1               5


<210> SEQ ID NO 5
<211> LENGTH: 27
<212> TYPE: DNA
<213> ORGANISM: Artificial Sequence
<220> FEATURE:
<223> OTHER INFORMATION: DNA sequence of H-HDEL

<400> SEQUENCE: 5

caccaccatc accaccatga tgagctc                                          27


<210> SEQ ID NO 6
<211> LENGTH: 231
<212> TYPE: PRT
<213> ORGANISM: Artificial Sequence
<220> FEATURE:
<223> OTHER INFORMATION: Amino acid sequence of hFc (Fc fragment of
      human immunoglobulin heavy chain)

<400> SEQUENCE: 6

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230


<210> SEQ ID NO 7
```

<211> LENGTH: 693
<212> TYPE: DNA
<213> ORGANISM: Artificial Sequence
<220> FEATURE:
<223> OTHER INFORMATION: DNA sequence of hFc (Fc fragment of human immunoglobulin heavy chain)

<400> SEQUENCE: 7

```
cccaaatctt gtgacaaaac tcacacatgc ccaccgtgcc cagcacctga actcctgggg      60

ggaccgtcag tcttcctctt ccccccaaaa cccaaggaca ccctcatgat ctcccggacc     120

cctgaggtca catgcgtggt ggtggacgtg agccacgaag accctgaggt caagttcaac     180

tggtacgtgg acggcgtgga ggtgcataat gccaagacaa agccgcggga ggagcagtac     240

aacagcacgt accgtgtggt cagcgtcctc accgtcctgc accaggactg gctgaatggc     300

aaggagtaca agtgcaaggt ctccaacaaa gccctcccag cccccatcga gaaaaccatc     360

tccaaagcca aagggcagcc ccgagaacca caggtgtaca ccctgccccc atcccgtgag     420

gagatgacca agaaccaggt cagcctgacc tgcctggtca aaggcttcta tcccagcgac     480

atcgccgtgg agtgggagag caatgggcag ccggagaaca actacaagac cacgcctccc     540

gtgctggact ccgacggctc cttcttcctc tatagcaagc tcaccgtgga caagagcagg     600

tggcagcagg ggaacgtctt ctcatgctcc gtgatgcatg aggctctgca caaccactac     660

acgcagaaga gcctctccct gtcccctggt aaa                                  693
```

<210> SEQ ID NO 8
<211> LENGTH: 4
<212> TYPE: PRT
<213> ORGANISM: Artificial Sequence
<220> FEATURE:
<223> OTHER INFORMATION: Amino acid sequence of HDEL (histidine-aspartic acid-glutamic acid-leucine tag)

<400> SEQUENCE: 8

```
His Asp Glu Leu
1
```

<210> SEQ ID NO 9
<211> LENGTH: 12
<212> TYPE: DNA
<213> ORGANISM: Artificial Sequence
<220> FEATURE:
<223> OTHER INFORMATION: DNA sequence of HDEL (histidine-aspartic acid-glutamic acid-leucine tag)

<400> SEQUENCE: 9

```
cacgatgagc tc                                                          12
```

<210> SEQ ID NO 10
<211> LENGTH: 465
<212> TYPE: PRT
<213> ORGANISM: Artificial Sequence
<220> FEATURE:
<223> OTHER INFORMATION: Amino acid sequence of Zika:Env1 antigen (zika envelope protein ectodomain-H-HDEL)

<400> SEQUENCE: 10

```
Gly Ser Ile Arg Cys Ile Gly Val Ser Asn Arg Asp Phe Val Glu Gly
1               5                   10                  15

Met Ser Gly Gly Thr Trp Val Asp Val Val Leu Glu His Gly Gly Cys
            20                  25                  30

Val Thr Val Met Ala Gln Asp Lys Pro Thr Val Asp Ile Glu Leu Val
        35                  40                  45
```

```
Thr Thr Thr Val Ser Asn Met Ala Glu Val Arg Ser Tyr Cys Tyr Glu
    50                  55                  60

Ala Ser Ile Ser Asp Met Ala Ser Asp Ser Arg Cys Pro Thr Gln Gly
65                  70                  75                  80

Glu Ala Tyr Leu Asp Lys Gln Ser Asp Thr Gln Tyr Val Cys Lys Arg
                85                  90                  95

Thr Leu Val Asp Arg Gly Trp Gly Asn Gly Cys Gly Leu Phe Gly Lys
            100                 105                 110

Gly Ser Leu Val Thr Cys Ala Lys Phe Ala Cys Ser Lys Lys Met Thr
        115                 120                 125

Gly Lys Ser Ile Gln Pro Glu Asn Leu Glu Tyr Arg Ile Met Leu Ser
    130                 135                 140

Val His Gly Ser Gln His Ser Gly Met Ile Val Asn Asp Thr Gly His
145                 150                 155                 160

Glu Thr Asp Glu Asn Arg Ala Lys Val Glu Ile Thr Pro Asn Ser Pro
                165                 170                 175

Arg Ala Glu Ala Thr Leu Gly Gly Phe Gly Ser Leu Gly Leu Asp Cys
            180                 185                 190

Glu Pro Arg Thr Gly Leu Asp Phe Ser Asp Leu Tyr Tyr Leu Thr Met
        195                 200                 205

Asn Asn Lys His Trp Leu Val His Lys Glu Trp Phe His Asp Ile Pro
    210                 215                 220

Leu Pro Trp His Ala Gly Ala Asp Thr Gly Thr Pro His Trp Asn Asn
225                 230                 235                 240

Lys Glu Ala Leu Val Glu Phe Lys Asp Ala His Ala Lys Arg Gln Thr
                245                 250                 255

Val Val Val Leu Gly Ser Gln Glu Gly Ala Val His Thr Ala Leu Ala
            260                 265                 270

Gly Ala Leu Glu Ala Glu Met Asp Gly Ala Lys Gly Arg Leu Ser Ser
        275                 280                 285

Gly His Leu Lys Cys Arg Leu Lys Met Asp Lys Leu Arg Leu Lys Gly
    290                 295                 300

Val Ser Tyr Ser Leu Cys Thr Ala Ala Phe Thr Phe Thr Lys Ile Pro
305                 310                 315                 320

Ala Glu Thr Leu His Gly Thr Val Thr Val Glu Val Gln Tyr Ala Gly
                325                 330                 335

Thr Asp Gly Pro Cys Lys Val Pro Ala Gln Met Ala Val Asp Met Gln
            340                 345                 350

Thr Leu Thr Pro Val Gly Arg Leu Ile Thr Ala Asn Pro Val Ile Thr
        355                 360                 365

Glu Ser Thr Glu Asn Ser Lys Met Met Leu Glu Leu Asp Pro Pro Phe
    370                 375                 380

Gly Asp Ser Tyr Ile Val Ile Gly Val Gly Glu Lys Lys Ile Thr His
385                 390                 395                 400

His Trp His Arg Ser Gly Ser Thr Ile Gly Lys Ala Phe Glu Ala Thr
                405                 410                 415

Val Arg Gly Ala Arg Arg Met Ala Val Leu Gly Asp Thr Ala Trp Asp
            420                 425                 430

Phe Gly Ser Val Gly Gly Ala Leu Asn Ser Leu Gly Lys Gly Ile His
        435                 440                 445

Gln Ile Phe Gly Ala Ala Phe Lys His His His His His His Asp Glu
    450                 455                 460
```

Leu
465

<210> SEQ ID NO 11
<211> LENGTH: 1682
<212> TYPE: DNA
<213> ORGANISM: Artificial Sequence
<220> FEATURE:
<223> OTHER INFORMATION: DNA sequence of Zika:Env1 expression cassette (NB-zika envelope protein ectodomain-H-HDEL)

<400> SEQUENCE: 11

```
tctagaatta ttacatcaaa acaaaaaatg gctcgctcgt ttggagctaa cagtaccgtt     60
gtgttggcga tcatcttctt cggtgagtga ttttccgatc ttcttctccg atttagatct    120
cctctacatt gttgcttaat ctcagaacct tttttcgttg ttcctggatc tgaatgtgtt    180
tgtttgcaat ttcacgatct taaaaggtta gatctcgatt ggtattgacg attggaatct    240
ttacgatttc aggatgttta tttgcgttgt cctctgcagg atccatacga tgtattggtg    300
tttcaaatag ggattttgtt gaaggcatga gtggagggac atgggtggac gttgtattgg    360
agcacggcgg ttgcgtaacc gtgatggccc aagataagcc aactgttgac attgaactgg    420
tcacgactac tgtgtcaaat atggctgaag tgcggagcta ttgttatgaa gcatctatta    480
gtgatatggc tagtgattca agatgtccta cacagggaga agcatatctg gataagcagt    540
ccgatacaca atatgtatgc aaacgtactc ttgttgatag ggttggggt aacggttgcg    600
gattattcgg caagggttcc ttggttactt gtgctaaatt cgcgtgtagc aaaaagatga    660
caggtaagtc gatacagcct gagaatcttg agtaccgcat catgttgtct gttcatggta    720
gtcaacattc tgggatgatc gtcaatgaca ctgggcatga gactgatgaa aacagagcaa    780
aggttgagat tactcccaat tcaccaaggg ctgaagctac tctcggagga tttggttctt    840
taggattgga ttgcgagccg agaactggac tagatttttc tgatctttac taccttacta    900
tgaataacaa acattggctc gttcacaaag aatggtttca cgacattcca cttccttggc    960
atgccggagc agacactggt actcctcatt ggaataacaa agaggctctg gtcgaattta   1020
aggacgctca cgcaaaaaga caaacagttg tggttttagg tagccaggag ggggcagttc   1080
atacggcttt ggcaggtgcc ttggaagctg aaatggatgg tgccaagggt cgattgtcca   1140
gtggtcactt gaagtgtaga ttgaagatgg ataaacttcg tcttaagggg gtgtcatatt   1200
ctctgtgcac tgctgctttt actttcacaa aaataccggc agaaacgtta catggtaccg   1260
tgacagtcga ggttcaatat gctggaactg atgggccttg taaggtacca gcccagatgg   1320
ctgtcgatat gcaaacctta acaccagttg gaagacttat aactgctaat cccgttatta   1380
cagagtctac tgaaaattct aaaatgatgc tagagcttga tcctccattt ggagactctt   1440
acattgtgat tggagttggt gaaaaaaaga ttactcatca ttggcatagg tctggtagta   1500
caatcggtaa agcatttgaa gctaccgtaa ggggcgcgag aagaatggct gttcttggag   1560
atacagcttg ggattttgga tcagtaggtg gagccctcaa ctcactcgga aaaggtattc   1620
accagatctt cggtgcagca ttcaagcacc accatcacca ccatgatgag ctctagctcg   1680
ag                                                                  1682
```

<210> SEQ ID NO 12
<211> LENGTH: 694
<212> TYPE: PRT
<213> ORGANISM: Artificial Sequence
<220> FEATURE:
<223> OTHER INFORMATION: Amino acid sequence of Zika:Env antigen (zika -continued envelope protein ectodomain-human Fc-HDEL)

<400> SEQUENCE: 12

```
Gly Ser Ile Arg Cys Ile Gly Val Ser Asn Arg Asp Phe Val Glu Gly
1               5                   10                  15

Met Ser Gly Gly Thr Trp Val Asp Val Val Leu Glu His Gly Gly Cys
            20                  25                  30

Val Thr Val Met Ala Gln Asp Lys Pro Thr Val Asp Ile Glu Leu Val
        35                  40                  45

Thr Thr Thr Val Ser Asn Met Ala Glu Val Arg Ser Tyr Cys Tyr Glu
    50                  55                  60

Ala Ser Ile Ser Asp Met Ala Ser Asp Ser Arg Cys Pro Thr Gln Gly
65                  70                  75                  80

Glu Ala Tyr Leu Asp Lys Gln Ser Asp Thr Gln Tyr Val Cys Lys Arg
                85                  90                  95

Thr Leu Val Asp Arg Gly Trp Gly Asn Gly Cys Gly Leu Phe Gly Lys
            100                 105                 110

Gly Ser Leu Val Thr Cys Ala Lys Phe Ala Cys Ser Lys Lys Met Thr
        115                 120                 125

Gly Lys Ser Ile Gln Pro Glu Asn Leu Glu Tyr Arg Ile Met Leu Ser
    130                 135                 140

Val His Gly Ser Gln His Ser Gly Met Ile Val Asn Asp Thr Gly His
145                 150                 155                 160

Glu Thr Asp Glu Asn Arg Ala Lys Val Glu Ile Thr Pro Asn Ser Pro
                165                 170                 175

Arg Ala Glu Ala Thr Leu Gly Gly Phe Gly Ser Leu Gly Leu Asp Cys
            180                 185                 190

Glu Pro Arg Thr Gly Leu Asp Phe Ser Asp Leu Tyr Tyr Leu Thr Met
        195                 200                 205

Asn Asn Lys His Trp Leu Val His Lys Glu Trp Phe His Asp Ile Pro
    210                 215                 220

Leu Pro Trp His Ala Gly Ala Asp Thr Gly Thr Pro His Trp Asn Asn
225                 230                 235                 240

Lys Glu Ala Leu Val Glu Phe Lys Asp Ala His Ala Lys Arg Gln Thr
                245                 250                 255

Val Val Val Leu Gly Ser Gln Glu Gly Ala Val His Thr Ala Leu Ala
            260                 265                 270

Gly Ala Leu Glu Ala Glu Met Asp Gly Ala Lys Gly Arg Leu Ser Ser
        275                 280                 285

Gly His Leu Lys Cys Arg Leu Lys Met Asp Lys Leu Arg Leu Lys Gly
    290                 295                 300

Val Ser Tyr Ser Leu Cys Thr Ala Ala Phe Thr Phe Thr Lys Ile Pro
305                 310                 315                 320

Ala Glu Thr Leu His Gly Thr Val Thr Val Glu Val Gln Tyr Ala Gly
                325                 330                 335

Thr Asp Gly Pro Cys Lys Val Pro Ala Gln Met Ala Val Asp Met Gln
            340                 345                 350

Thr Leu Thr Pro Val Gly Arg Leu Ile Thr Ala Asn Pro Val Ile Thr
        355                 360                 365

Glu Ser Thr Glu Asn Ser Lys Met Met Leu Glu Leu Asp Pro Pro Phe
    370                 375                 380

Gly Asp Ser Tyr Ile Val Ile Gly Val Gly Glu Lys Lys Ile Thr His
385                 390                 395                 400
```

```
His Trp His Arg Ser Gly Ser Thr Ile Gly Lys Ala Phe Glu Ala Thr
                405                 410                 415

Val Arg Gly Ala Arg Arg Met Ala Val Leu Gly Asp Thr Ala Trp Asp
            420                 425                 430

Phe Gly Ser Val Gly Gly Ala Leu Asn Ser Leu Gly Lys Gly Ile His
        435                 440                 445

Gln Ile Phe Gly Ala Ala Phe Lys Ala Arg Glu Pro Lys Ser Cys Asp
    450                 455                 460

Lys Thr His Thr Cys Pro Pro Cys Pro Ala Pro Glu Leu Leu Gly Gly
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
            500                 505                 510

Asp Pro Glu Val Lys Phe Asn Trp Tyr Val Asp Gly Val Glu Val His
        515                 520                 525

Asn Ala Lys Thr Lys Pro Arg Glu Glu Gln Tyr Asn Ser Thr Tyr Arg
    530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Pro Ala Pro Ile Glu
                565                 570                 575

Lys Thr Ile Ser Lys Ala Lys Gly Gln Pro Arg Glu Pro Gln Val Tyr
            580                 585                 590

Thr Leu Pro Pro Ser Arg Glu Glu Met Thr Lys Asn Gln Val Ser Leu
        595                 600                 605

Thr Cys Leu Val Lys Gly Phe Tyr Pro Ser Asp Ile Ala Val Glu Trp
    610                 615                 620

Glu Ser Asn Gly Gln Pro Glu Asn Asn Tyr Lys Thr Thr Pro Pro Val
625                 630                 635                 640

Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
            660                 665                 670

Glu Ala Leu His Asn His Tyr Thr Gln Lys Ser Leu Ser Leu Ser Pro
        675                 680                 685

Gly Lys His Asp Glu Leu
    690


<210> SEQ ID NO 13
<211> LENGTH: 2369
<212> TYPE: DNA
<213> ORGANISM: Artificial Sequence
<220> FEATURE:
<223> OTHER INFORMATION: DNA sequence of Zika:Env expression cassette
      (NB-zika envelope protein ectodomain-human Fc-HDEL)

<400> SEQUENCE: 13

tctagaatta ttacatcaaa acaaaaaatg gctcgctcgt ttggagctaa cagtaccgtt      60

gtgttggcga tcatcttctt cggtgagtga ttttccgatc ttcttctccg atttagatct     120

cctctacatt gttgcttaat ctcagaacct tttttcgttg ttcctggatc tgaatgtgtt     180

tgtttgcaat ttcacgatct taaaaggtta gatctcgatt ggtattgacg attggaatct     240

ttacgatttc aggatgttta tttgcgttgt cctctgcagg atccatacga tgtattggtg     300

tttcaaatag ggattttgtt gaaggcatga gtggagggac atgggtggac gttgtattgg     360
```

```
agcacggcgg ttgcgtaacc gtgatggccc aagataagcc aactgttgac attgaactgg    420
tcacgactac tgtgtcaaat atggctgaag tgcggagcta ttgttatgaa gcatctatta    480
gtgatatggc tagtgattca agatgtccta cacagggaga agcatatctg gataagcagt    540
ccgatacaca atatgtatgc aaacgtactc ttgttgatag gggttggggt aacggttgcg    600
gattattcgg caagggttcc ttggttactt gtgctaaatt cgcgtgtagc aaaaagatga    660
caggtaagtc gatacagcct gagaatcttg agtaccgcat catgttgtct gttcatggta    720
gtcaacattc tgggatgatc gtcaatgaca ctgggcatga gactgatgaa aacagagcaa    780
aggttgagat tactcccaat tcaccaaggg ctgaagctac tctcggagga tttggttctt    840
taggattgga ttgcgagccg agaactggac tagatttttc tgatctttac taccttacta    900
tgaataacaa acattggctc gttcacaaag aatggtttca cgacattcca cttccttggc    960
atgccggagc agacactggt actcctcatt ggaataacaa agaggctctg gtcgaattta   1020
aggacgctca cgcaaaaaga caaacagttg tggttttagg tagccaggag ggggcagttc   1080
atacggcttt ggcaggtgcc ttggaagctg aaatggatgg tgccaagggt cgattgtcca   1140
gtggtcactt gaagtgtaga ttgaagatgg ataaacttcg tcttaagggg gtgtcatatt   1200
ctctgtgcac tgctgctttt actttcacaa aaataccggc agaaacgtta catggtaccg   1260
tgacagtcga ggttcaatat gctggaactg atgggccttg taaggtacca gcccagatgg   1320
ctgtcgatat gcaaacctta acaccagttg gaagacttat aactgctaat cccgttatta   1380
cagagtctac tgaaaattct aaaatgatgc tagagcttga tcctccattt ggagactctt   1440
acattgtgat tggagttggt gaaaaaaaga ttactcatca ttggcatagg tctggtagta   1500
caatcggtaa agcatttgaa gctaccgtaa ggggcgcgag aagaatggct gttcttggag   1560
atacagcttg ggattttgga tcagtaggtg gagccctcaa ctcactcgga aaaggtattc   1620
accagatctt cggtgcagca ttcaaggccc gggagcccaa atcttgtgac aaaactcaca   1680
catgcccacc gtgcccagca cctgaactcc tggggggacc gtcagtcttc ctcttccccc   1740
caaaacccaa ggacaccctc atgatctccc ggacccctga ggtcacatgc gtggtggtgg   1800
acgtgagcca cgaagaccct gaggtcaagt tcaactggta cgtggacggc gtggaggtgc   1860
ataatgccaa gacaaagccg cgggaggagc agtacaacag cacgtaccgt gtggtcagcg   1920
tcctcaccgt cctgcaccag gactggctga atggcaagga gtacaagtgc aaggtctcca   1980
acaaagccct cccagccccc atcgagaaaa ccatctccaa agccaaaggg cagccccgag   2040
aaccacaggt gtacaccctg cccccatccc gtgaggagat gaccaagaac caggtcagcc   2100
tgacctgcct ggtcaaaggc ttctatccca gcgacatcgc cgtggagtgg gagagcaatg   2160
ggcagccgga gaacaactac aagaccacgc ctcccgtgct ggactccgac ggctccttct   2220
tcctctatag caagctcacc gtggacaaga gcaggtggca gcaggggaac gtcttctcat   2280
gctccgtgat gcatgaggct ctgcacaacc actacacgca gaagagcctc tccctgtccc   2340
ctggtaaaca cgatgagctc tagctcgag                                     2369
```

VACCINE COMPOSITION COMPRISING PLANT-EXPRESSED RECOMBINANT ZIKA VIRUS ENVELOPE PROTEIN AND PREPARATION METHOD THEREFOR

CROSS-REFERENCE TO RELATED APPLICATIONS

This application is a national phase application filed under 35 U.S.C. § 371 claiming benefit to International Patent Application No. PCT/KR2021/010650, filed Aug. 11, 2021, which claims the benefit of priority from Korean Patent Application No. 10-2020-0103211, filed Aug. 18, 2020, each of which is hereby incorporated by reference in its entirety.

REFERENCE TO A "SEQUENCE LISTING", A TABLE, OR A COMPUTER PROGRAM LISTING APPENDIX SUBMITTED AS AN ASCII TEXT FILE

The present application hereby incorporates by reference the entire contents of the text file named "206132-0144-00US_SequenceListing.txt" in ASCII format, which was created on Feb. 13, 2023, and is 25,876 bytes in size.

TECHNICAL FIELD

The present invention relates to a vaccine composition including a recombinant Zika virus envelope protein and an adjuvant as active ingredients, a preparation method therefor, a plant-expressing recombinant vector for producing the recombinant Zika virus envelope protein, and the like.

The present invention claims priority to and the benefit of Korean Patent Application No. 10-2020-0103211 filed in the Korean Intellectual Property Office on Aug. 18, 2020, and all the contents disclosed in the specification and drawings of the application are incorporated in this application.

BACKGROUND ART

Currently, there is no clinically approved vaccine for the prevention or treatment of Zika virus infections worldwide. Accordingly, there is no conventional art for the present invention disclosed in the present application. However, in order to provide a general understanding of the background and objects of the present invention, the following description is presented.

Zika virus is a mosquito-borne flavivirus of the Flaviviridae family, and is an infectious disease which induces Guillain-Barre syndrome and congenital malformations in fetuses and neonates. Since its outbreak in French Polynesia in 2013, Zika virus has increased infectivity and pathogenicity to increase risks, and after the outbreak was first reported in Brazil in May 2015, the virus spread rapidly in Latin America, and as of Jun. 1, 2016, 53 countries have had recent outbreaks (since 2015), 440,000 to 1.3 million people were estimated to be infected in Brazil alone in 2015, about 240 were confirmed to have cases of microcephaly as of May 26, and the number of suspected cases and diagnosed cases has reached about 5,000, indicating that the infection continues to spread, so that in consideration of the possibility of an epidemic of the disease, the market size is expected to be very large, but there is no specific preventive method other than aerosol insecticides for the control of disease vectors for the method of preventing Zika virus infection. Recently, as the development of vaccines against Zika virus, vaccine development through killed vaccines and recombinant protein expression using an *E. coli* expression system is underway. Existing vaccines typified by live vaccines or killed vaccines have a disadvantage in that they can exhibit toxicity, and in particular, there is a concern about live vaccines having side effects due to mutations. Although the *E. coli* recombinant expression system has advantages such as low strain maintenance costs, simple medium compositions and culture conditions, and simplification of the production process, the system has a risk of causing side effects such as immune responses to heterologous proteins. Therefore, there is a need for a Zika virus vaccine that minimizes the side effects described above and has excellent immunogenicity and protective efficacy.

DISCLOSURE

Technical Problem

The present invention has been devised to solve the above-described need for development of Zika virus vaccines and the problems in the related art, and a recombinant Zika virus envelope protein that can be efficiently produced using plants and exhibits high immunogenicity and virus neutralization ability, and a vaccine composition including the same as an active ingredient was developed, thereby completing the present invention.

Thus, an object of the present invention is to provide a vaccine composition including, as active ingredients, a recombinant Zika virus envelope protein including an amino acid sequence of SEQ ID NO: 1; and an adjuvant selected from alum, monophosphoryl lipid A (MPL), or a combination thereof.

Another object of the present invention is to provide a recombinant vector for expressing a Zika virus envelope protein, including a gene sequence of a Zika virus envelope protein consisting of a base sequence of SEQ ID NO: 2.

Still another object of the present invention is to provide a transformant transformed with the recombinant vector according to the present invention.

Yet another object of the present invention is to provide a recombinant Zika virus envelope protein prepared using the recombinant vector according to the present invention.

Yet another object of the present invention is to provide a method for producing a recombinant Zika virus envelope protein.

However, the technical objects which the present invention intends to achieve are not limited to the technical objects which have been mentioned above, and other technical objects which have not been mentioned will be clearly understood by a person with ordinary skill in the art to which the present invention pertains from the following description.

Technical Solution

To achieve the aforementioned objects of the present invention, the present invention provides a vaccine composition including, as active ingredients, a recombinant Zika virus envelope protein including an amino acid sequence of SEQ ID NO: 1; and an adjuvant selected from alum, monophosphoryl lipid A (MPL), or a combination thereof.

Further, the present invention provides a method for preventing or treating Zika virus infection, the method including: administering a vaccine composition including, as active ingredients, a recombinant Zika virus envelope protein including an amino acid sequence of SEQ ID NO: 1;

and an adjuvant selected from alum, monophosphoryl lipid A (MPL), or a combination thereof to a subject in need thereof.

Furthermore, the present invention provides a use of a composition including, as active ingredients, a recombinant Zika virus envelope protein including an amino acid sequence of SEQ ID NO: 1; and an adjuvant selected from alum, monophosphoryl lipid A (MPL), or a combination thereof for preventing or treating Zika virus infection.

In addition, the present invention provides a use of a recombinant Zika virus envelope protein including an amino acid sequence of SEQ ID NO: 1; and an adjuvant selected from alum, monophosphoryl lipid A (MPL), or a combination thereof for producing a vaccine used for Zika virus infection.

In an exemplary embodiment of the present invention, the recombinant Zika virus envelope protein may be one in which a polypeptide consisting of an amino acid sequence of SEQ ID NO: 4 is fused.

In another exemplary embodiment of the present invention, the recombinant Zika virus envelope protein may be one in which a polypeptide consisting of an amino acid sequence of SEQ ID NO: 6 is fused.

In still another exemplary embodiment of the present invention, the recombinant Zika virus envelope protein may be one in which a polypeptide consisting of an amino acid sequence of SEQ ID NO: 8 is further fused.

In yet another exemplary embodiment of the present invention, the recombinant Zika virus envelope protein may include an amino acid sequence of SEQ ID NO: 10 or 12.

In yet another exemplary embodiment of the present invention, the alum may be included at a ratio of 1:1 to 50 (envelope protein:alum) relative to the weight of the recombinant Zika virus envelope protein, but is not limited thereto.

In yet another exemplary embodiment of the present invention, the MPL may be included at a ratio of 1:0.4 to 2 (envelope protein:MPL) relative to the weight of the recombinant Zika virus envelope protein, but is not limited thereto.

In yet another exemplary embodiment of the present invention, the combination of the alum and the MPL may be included at a ratio of 1:1 to 50:0.4 to 2 (envelope protein: alum:MPL) relative to the weight of the recombinant Zika virus envelope protein, but is not limited thereto.

In yet another exemplary embodiment of the present invention, the vaccine composition may be inoculated one to three times, but is not limited thereto.

In yet another exemplary embodiment of the present invention, the inoculation may be performed at an interval of 14 to 28 days, but is not limited thereto.

In yet another exemplary embodiment of the present invention, the vaccine composition may have protective ability against one or more selected from the group consisting of a Zika virus PRVABC59 strain, a Zika virus MR766 strain and dengue virus type-2, but is not limited thereto.

In yet another exemplary embodiment of the present invention, the vaccine composition may promote the secretion of any one or more selected from the group consisting of interferon-gamma (IFN-γ), interleukin-12 (IL-12) and tumor necrosis factor-alpha (TNF-α).

In yet another exemplary embodiment of the present invention, the vaccine composition may induce the formation of a maternal antibody.

Further, the present invention provides a recombinant vector for expressing a Zika virus envelope protein, including a gene sequence of a Zika virus envelope protein consisting of a base sequence of SEQ ID NO: 2.

In an exemplary embodiment of the present invention, the vector may further include a base sequence of SEQ ID NO: 3, but is not limited thereto.

In another exemplary embodiment of the present invention, the vector may further include: a polynucleotide encoding an amino acid sequence of SEQ ID NO: 4; or a base sequence of SEQ ID NO: 5, but is not limited thereto.

In still another exemplary embodiment of the present invention, the vector may further include: a polynucleotide encoding an amino acid sequence of SEQ ID NO: 6; or a base sequence of SEQ ID NO: 7, but is not limited thereto.

In yet another exemplary embodiment of the present invention, the vector may further include: a polynucleotide encoding an amino acid sequence of SEQ ID NO: 8; or a base sequence of SEQ ID NO: 9, but is not limited thereto.

In yet another exemplary embodiment of the present invention, the vector may include a base sequence of SEQ ID NO: 11 or 13, but is not limited thereto.

In yet another exemplary embodiment of the present invention, the recombinant vector may be expressed in a plant.

Further, the present invention provides a transformant transformed with the recombinant vector according to the present invention.

In an exemplary embodiment of the present invention, the transformant may be a plant.

In addition, the present invention provides a recombinant Zika virus envelope protein prepared using the recombinant vector according to the present invention.

In an exemplary embodiment of the present invention, the recombinant Zika envelope protein may consist of an amino acid sequence of SEQ ID NO: 10 or 12, but is not limited thereto.

Furthermore, the present invention provides a method for producing a recombinant Zika virus envelope protein, the method including: (a) culturing a transformant according to the present invention; and (b) isolating and purifying a recombinant Zika virus envelope protein from the transformant or culture solution.

In an exemplary embodiment of the present invention, the purification in Step (b) may be performed using a water-soluble fraction, but is not limited thereto.

Advantageous Effects

Since the recombinant Zika virus envelope protein of the present invention can not only be effectively expressed even in plants, but also has high water solubility, and thus is easily isolated and purified, and also acts as an antigen in vivo to exhibit high immunogenicity and virus neutralizing ability, the recombinant Zika virus envelope protein of the present invention can be used as a novel Zika virus vaccine.

Further, since immune cells of mice inoculated with a vaccine composition containing the recombinant Zika virus envelope protein according to the present invention exhibit a specific increase in production of interferon-gamma (IFN-γ), interleukin-12 (IL-12) and tumor necrosis factor-alpha (TNF-α), which are cytokines specific for external stimulating antigens, it was found that the immunoprotective/preventive efficacy against Zika virus infection was enhanced. Therefore, the vaccine composition of the present invention can be usefully used for the prevention of Zika virus infection.

Furthermore, the present invention can verify an expression system with better immune efficacy by referring to the results of directly applying a recombinant Zika virus vaccine composition developed using a plant cell-derived expression system to an animal model, and this facilitates the development of a recombinant Zika virus vaccine applicable to humans, and can simultaneously be used to develop vaccines against other mosquito-borne diseases similar to Zika virus.

DESCRIPTION OF DRAWINGS

FIGS. 6A to 6C are views illustrating the results of inoculating mice with the vaccine composition according to the present invention one to three times, and measuring the antibody titer of the serum isolated by retro-orbital sinus/plexus sampling 7 to 14 days later using indirect ELISA, FIG. 6A is a flow chart showing the inoculation and blood sampling schedule, and FIGS. 6B and 6C are graphs comparing the levels of antibodies recognizing Zika:Envl and Zika:Env in the sera of immunized mice according to inoculation time and group (one-way ANOVA; *, $p<0.05$; , $p<0.01$; *, $p<0.001$).

FIG. 7A shows the results of using a plate coated with Zika:Envl, and FIG. 7B shows the results of using a plate coated with Zika-Env.

FIGS. 17A and 17B are views illustrating the results of measuring the ratios of CD4 and CD8 T cells ($CD3^+$, $CD4^+$, $CD8^+$) through flow cytometry by inoculating each vaccine candidate once or three times and pooling spleen immune cells derived from the same group 7 days later (day-7) or 3 days later (day-45), respectively.

FIGS. 18A to 18D are views illustrating the results of measuring the proportions of exhausted T cells ($CD4^+PD\text{-}1^+$ or $CD8^+PD\text{-}1^+$) through flow cytometry by inoculating each vaccine candidate once or three times and pooling spleen immune cells derived from the same group 7 days later (day-7) or 3 days later (day-45), respectively.

FIGS. 24A and 24B are views illustrating the results of observing survival rates (24A) and body weight changes (24B) by challenging offspring mice obtained by inoculating vaccine candidates (Zika:Envl, Zika:Env) three times and mating 7 days later with two types of Zika virus or dengue virus type 2.

MODES OF THE INVENTION

Figure 1:
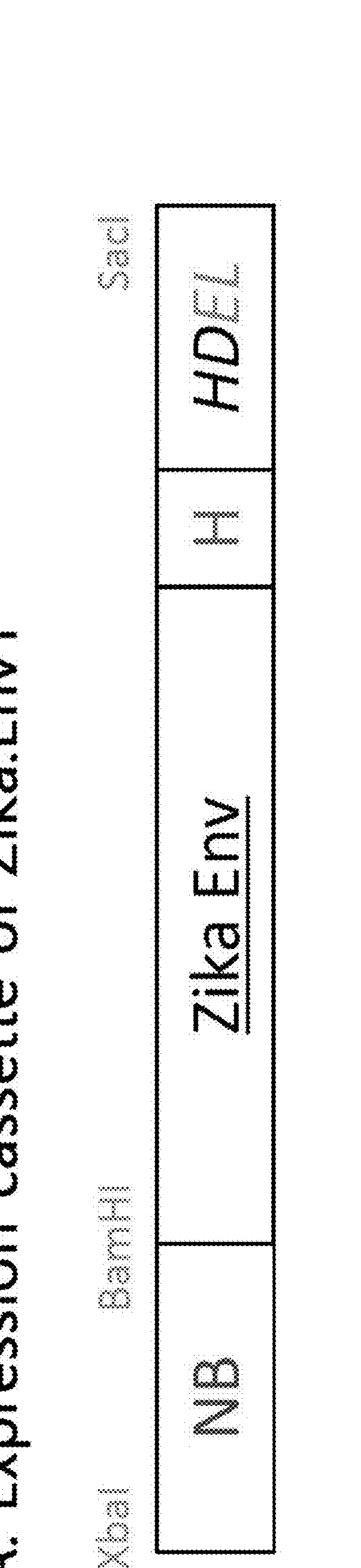
FIG. 1 is a set of structure maps illustrating the gene arrays of the expression cassettes for the expression of two recombinant Zika virus envelope proteins in a plant (abbreviation, hereinafter, the same: NB, new chaperone binding protein; Zika Env, Zika envelope protein ectodomain; H, polyhistidine tag; hFc, Fc fragment of human immunoglobulin heavy chain; HDEL, histidine-aspartic acid-glutamic acid-leucine tag; Zika:Envl, NB-Zika envelope protein ectodomain-H-HDEL; Zika:Env, NB-Zika envelope protein ectodomain-human Fc-HDEL).
Figure 1:
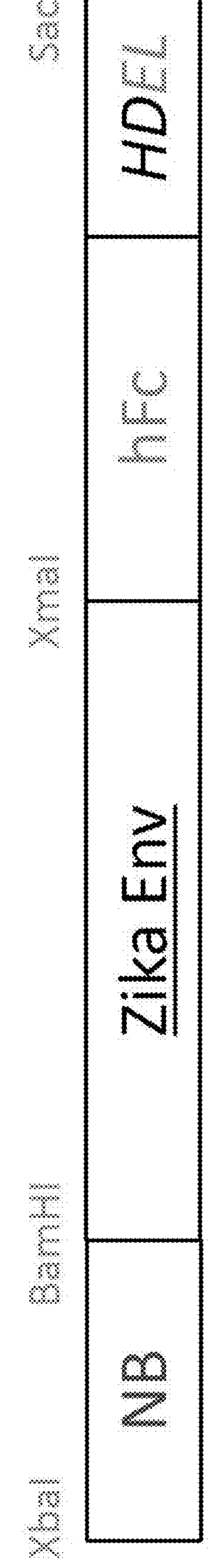

The present inventors developed two recombinant Zika virus vaccines (referred to as Zika:Envl and Zika:Env, respectively) in which the Zika virus envelope protein was expressed in a plant in order to develop a vaccine capable of minimizing in vivo side effects and reducing production costs, and confirmed whether the inoculation of the composition according to the present invention induces an immune response such as activation of various immune molecules capable of directly killing pathogens along with an antibody response against antigens similar to in vivo virus penetration.

Hereinafter, the present invention will be specifically described. Unless otherwise defined, all technical and scientific terms used herein have the same meaning as commonly understood by a person with ordinary skill in the art to which the present invention pertains. In general, the nomenclature used herein is well known and commonly used in the art.

The present invention may provide a vaccine composition including, as active ingredients, a recombinant Zika virus envelope protein including an amino acid sequence of SEQ ID NO: 1; and an adjuvant selected from alum, monophosphoryl lipid A (MPL), or a combination thereof.

The present invention relates to a vaccine composition containing a recombinant Zika virus envelope protein including an amino acid sequence of SEQ ID NO: 1, and in an exemplary embodiment, a plant expression vector recombined so as to express the Zika virus envelope protein, which is a major immunogenicity-inducing antigenic site of Zika virus, was constructed and cloned, and then introduced into *Agrobacterium* strain LBA4404, and the vector-introduced *Agrobacterium* was allowed to infiltrate *Nicotiana benthamiana* to produce a recombinant antigen protein from the *Nicotiana benthamiana*. The recombinant antigen protein provides a preventive strategy against Zika virus by inducing an antibody response against antigens similar to those during in vivo virus penetration and an immune response such as activation of various immune molecules capable of directly destroying pathogens.

In an exemplary embodiment of the present invention, the recombinant Zika virus envelope protein may be one in which a polypeptide consisting of an amino acid sequence of SEQ ID NO: 4, that is, polyhistidine and histidine-aspartic acid-glutamic acid-leucine (hereinafter referred to as 'HDEL') tag (H-HDEL), is fused.

In another exemplary embodiment of the present invention, the recombinant Zika virus envelope protein may be one in which a polypeptide consisting of an amino acid sequence of SEQ ID NO: 6, that is, an Fc fragment of a human immunoglobulin heavy chain (hereinafter referred to as 'hFc'), is fused. The hFc binding site may be directly linked to the C-terminus of the peptide or protein for the purpose of being expressed or synthesized in plant cells, or added (or linked) indirectly, that is, via another peptide or protein.

In still another exemplary embodiment of the present invention, the recombinant Zika virus envelope protein may be one in which a polypeptide consisting of an amino acid sequence of SEQ ID NO: 8, that is, the HDEL tag, is further fused. The HDEL binding site may be directly linked to the C-terminus of the peptide or protein for the purpose of being expressed or synthesized in plant cells, or added (or linked) indirectly, that is, via another peptide or protein.

In yet another exemplary embodiment of the present invention, the recombinant Zika virus envelope protein may include an amino acid sequence of SEQ ID NO: 10 or 12. For example, the recombinant Zika virus envelope protein may be a sequential fusion of a Zika virus envelope protein, a polyhistidine tag and an HDEL tag, or a sequential fusion of a Zika virus envelope protein, hFc and an HDEL tag.

As used herein, the term "Zika virus" refers to a virus belonging to the Flaviviridae family and having a single-stranded, approximately 10-kilobase long, positive-sense RNA as a genome, and the RNA genome encodes seven nonstructural and three structural proteins. The three major viral structural proteins include capsid (C), pre-membrane (prM) and envelope (E), and the seven nonstructural proteins include one long open reading frame (ORF) encoding NS1, NS1, NS2A, NS2B, NS3, NS4A, NS4B, and NS5.

The "envelope protein (E)" included in the structural proteins in the present invention is responsible for the entry of Zika virus and becomes a main target of neutralizing antibodies. To date, monoclonal antibodies that neutralize a plurality of potent flavivirus types have been shown to target domain-III of the envelope protein. Therefore, the Zika virus envelope protein including domain-III exhibits immunogenicity when administered to a subject in need, and may significantly contribute to the formation of antibodies capable of fighting Zika virus infection.

The Zika virus envelope protein also includes functional equivalents of the amino acid sequence represented by SEQ ID NO: 1 within the scope of the present invention, the function equivalent has, as a result of addition, substitution, or deletion of an amino acid, a sequence homology of at least 60% or more, preferably 70% or more, more preferably 80% or more, and most preferably 90% or more with the amino acid sequence represented by SEQ ID NO: 1, and refers to a polypeptide showing substantially the same activity as that of the amino acid sequence represented by SEQ ID NO: 1, and is not limited thereto as long as the amino acid sequence is an amino acid sequence of a Zika virus envelope protein which can be stably produced using plants.

As used herein, the term "antigen" generally refers to all materials that cause an immune response in the body, and is preferably a virus, a chemical, a bacterium, pollen, a cancer cell, and the like or a partial peptide or protein thereof, but is not limited thereto as long as it is a material that may cause an immune response in the body.

As used herein, the term "vaccine" is a biological preparation containing an antigen that causes an immune response in an organism, and refers to an immunogen that induces immunity in an organism by injection or oral administration into a human or animal for prevention of an infectious disease. The animal is a human or non-human animal, and the non-human animal refers to a pig, a cow, a horse, a dog, a goat, sheep, and the like, but is not limited thereto.

As used herein, the term "adjuvant" refers to a material or composition which may be added to a vaccine or pharmaceutically active components to increase or affect the immune response. Representatively, the adjuvant typically refers to a carrier or auxiliary material for an immunogen and/or another pharmaceutically active material or composition. Typically, the term "adjuvant" should be interpreted as a broad concept, and refers to a material or stratagem in a broad range, which may enhance the immunogenicity of an antigen which is incorporated into the adjuvant or administered with the adjuvant. Further, the adjuvant is not limited thereto, and may be divided into an immune potentiator, an antigen delivery system, or a combination thereof. Examples of a well-known adjuvant may include aluminum hydroxide, Freund's complete or incomplete adjuvant, DEAE dextran, levamisole, PCG, and poly I:C, poly A:U, or the like. In an exemplary embodiment of the present invention, alum and monophosphoryl lipid A (MPL), were used as an adjuvant.

In an exemplary embodiment of the present invention, the alum may be included at a ratio of 1:1 to 50 (envelope protein:alum) relative to the weight of the recombinant Zika virus envelope protein. More specifically, the ratio of the weight of the recombinant Zika virus envelope protein to the weight of the alum may be 1:1, 1:5, 1:10, 1:15, 1:20, 1:25, 1:30, 1:35, 1:40, 1:45 or 1:50, but is not limited thereto.

In another exemplary embodiment of the present invention, the MPL may be included at a ratio of 1:0.4 to 2 (envelope protein:MPL) relative to the weight of the recombination Zika virus envelope protein. More specifically, the ratio of the weight of the recombinant Zika virus envelope protein to the weight of MPL may be 1:0.4, 1:0.5, 1:0.6, 1:0.7, 1:0.8, 1:0.9, 1:1, 1:1.2, 1:1.4, 1:1.6, 1:1.8 or 1:2, but is not limited thereto.

In still another exemplary embodiment of the present invention, the combination of the alum and the MPL may be included at a ratio of 1:1 to 50:0.4 to 2 (envelope protein: alum:MPL) relative to the weight of the recombinant Zika virus envelope protein. More specifically, the ratio of the weight of the recombinant Zika virus envelope protein to the weight of the alum to the weight of the MPL may be 1:1:0.4, 1:5:0.4, 1:10:0.4, 1:20:0.4, 1:30:0.4, 1:40:0.4, 1:50:0.4, 1:1:0.6, 1:5:0.6, 1:10:0.6, 1:20:0.6, 1:30:0.6, 1:40:0.6, 1:50:0.6, 1:1:1, 1:5:1, 1:10:1, 1:20:1, 1:30:1, 1:40:1, 1:50:1, 1:1:1.4, 1:5:1.4, 1:10:1.4, 1:20:1.4, 1:30:1.4, 1:40:1.4, 1:50:1.4, 1:1:2, 1:5:2, 1:10:2, 1:20:2, 1:30:2, 1:40:2, 1:50:2, or the like, but is not limited thereto. For example, when 50 μg of a recombinant Zika virus envelope protein is included in the vaccine composition according to the invention, 50 to 2500 μg of the alarm may be included and 20 to 100 μg of the MPL may be included. As another example, when 10 μg of a recombinant Zika virus envelope protein is included in the vaccine composition according to the invention, 10 to 500 μg of the alarm may be included and 4 to 20 μg of the MPL may be included.

In an exemplary embodiment of the present invention, when the vaccine composition is inoculated 1 to 3 times at an interval of 14 to 28 days, the highest levels of neutralizing antibodies, cellular immune response, maternal antibody formation ability and protective efficacy are shown.

In another exemplary embodiment of the present invention, the vaccine composition may have a protective ability against an Asian-lineage Zika virus strain or an African-lineage Zika virus strain. Examples of suitable Zika viruses of the present invention include, without limitation, viruses from African and/or Asian lineages. Several lineages within the African and Asian lineages of Zika virus have already been identified. For example, against one or more suitable series of Zika viruses known in the art, including the series Mr 766, ArD 41519, IbH 30656, P6-740, EC Yap, FSS13025, ArD 7117, ArD 9957, ArD 30101, ArD 30156, ArD 30332, HD 78788, ArD 127707, ArD 127710, ArD 127984, ArD 127988, ArD 127994, ArD 128000, ArD 132912, 132915, ArD 141170, ArD 142623, ArD 149917, ArD 149810, ArD 149938, ArD 157995, ArD 158084, ArD 165522, ArD 165531, ArA 1465, ArA 27101, ArA 27290, ArA 27106, ArA 27096, ArA 27407, ArA 27433, ArA 506/96, ArA 975-99, Ara 982-99, ArA 986-99, ArA 2718, ArB 1362, Nigeria68, Malaysia66, Kedougou84, Suriname, MR1429, PRVABC59, ECMN2007, DakAr41524, H/PF/2013, R103451, 103344, 8375, JMB-185, ZIKV/H, sapiens/Brazil/Natal/2015, SPH2015, ZIKV/Hu/Chiba/S36/2016 and/or Cuba2017, the vaccine composition of the present invention may have protective ability. In some exemplary embodiments, it was confirmed that the vaccine composition of the present invention has protective ability against a Zika virus PRVABC59 strain and a Zika virus MR766 strain.

In another exemplary embodiment of the present invention, the vaccine composition may have protective ability against dengue virus type-2.

In still another exemplary embodiment of the present invention, the vaccine composition may promote the secretion of any one or more cytokines selected from the group consisting of interferon-gamma (IFN-γ), interleukin-12 (IL-12) and tumor necrosis factor-alpha (TNF-α).

In yet another exemplary embodiment of the present invention, the vaccine composition may induce the formation of a maternal antibody, and may induce maternal cellular immunity.

Meanwhile, the "vaccine composition" of the present invention may be used by being formulated in the form of an oral formulation such as a powder, a granule, a tablet, a capsule, a suspension, an emulsion, a syrup, and an aerosol, and a sterile injection solution, according to a typical method. When the composition is prepared, the composition may be prepared using a commonly used diluent or excipient, such as a filler, an extender, a binder, a wetting agent, a disintegrant, and a surfactant. A solid formulation for oral formulation includes a tablet, a pill, a powder, a granule, and the like, and the solid formulation may be prepared by mixing at least one excipient, for example, starch, calcium carbonate, sucrose or lactose, gelatin, and the like with a lecithin-like emulsifier. Further, in addition to simple excipients, lubricants such as magnesium stearate and talc may also be used. As a liquid formulation for oral administration, a suspension, a liquid for internal use, an emulsion, a syrup, and the like may be used, and in addition to water and liquid paraffin which are simple commonly used diluents, various excipients, for example, a wetting agent, a sweetener, an aromatic, a preservative, and the like, may be included. Examples of a formulation for parenteral administration include an aqueous sterile solution, a non-aqueous solvent, a suspension, an emulsion, and a freeze-dried preparation. As the non-aqueous solvent and the suspension, it is possible to use propylene glycol, polyethylene glycol, a vegetable oil such as olive oil, an injectable ester such as ethyl oleate, and the like.

The route of administration of the vaccine composition according to the present invention includes, but is not limited to, oral, intravenous, intramuscular, intraarterial, intramedullary, intrathecal, intracardiac, transdermal, subcutaneous, intraperitoneal, intranasal, intestinal, topical, sublingual or rectal routes. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The vaccine composition of the present invention may also be administered in the form of a suppository for rectal administration.

The dose of the vaccine composition or pharmaceutical composition according to the present invention is selected in consideration of the age, body weight, sex, physical condition and the like of the individual. The amount required to induce an immunoprotective response in an individual without particular side effects may vary depending on the recombinant protein used as an immunogen and the presence of a random excipient.

As another aspect of the present invention, the present invention may provide a recombinant vector for expressing a Zika virus envelope protein, including a gene sequence of a Zika virus envelope protein consisting of a base sequence of SEQ ID NO: 2.

Vaccines for preventing viral diseases including Zika virus infection are mainly produced using animal cells without using bacteria due to problems such as protein folding and glycosylation. However, regarding a vaccine production method using animal cells, the vaccine is not easy to produce because it costs a lot to expand the equipment for mass production, and in most cases, the vaccine price is high. Further, inactivated virus vaccines prepared using animal cells have disadvantages of not only being difficult to store, but also are highly likely to be contaminated with viruses that can infect animals. However, the present invention has compensated for these disadvantages by using plants. That is, unlike animal cells, plants are very unlikely to be contaminated with viruses that can infect animals, and a vaccine can be mass-produced at any time as long as a cultivation area is secured and can be stored for a long period of time through a plant, so that an inexpensive vaccine can be stably produced.

Therefore, the recombinant vector for expressing a Zika virus envelope protein according to the present invention is a recombinant vector for plant expression.

In an exemplary embodiment of the present invention, the recombinant vector may additionally include a polynucleotide encoding a new chaperone binding protein (NB), a polynucleotide encoding an Fc fragment of a human immunoglobulin heavy chain (hFc), a polynucleotide encoding a polyhistidine tag or His-Asp-Glu-Leu (HDEL) tag, and the like.

The polynucleotide encoding the NB is a gene including a base sequence of SEQ ID NO: 3, and is preferably a gene represented by SEQ ID NO: 3, but may include a base sequence having a sequence homology of 80% or more, more preferably 90% or more, and even more preferably 95% or more with the base sequence of SEQ ID NO: 3, and may be located towards the 5' end of the polynucleotide sequence encoding the recombinant Zika virus envelope protein. In the NB, when the recombinant protein is expressed, all or part of the amino acid sequence is cut, so that the entire amino acid sequence may be removed from the recombinant Zika virus envelope protein of the present invention or only a part of the amino acid may remain.

Further, the polynucleotide encoding the hFc is a gene including a base sequence of SEQ ID NO: 7, and is preferably a gene represented by SEQ ID NO: 7, but may include a base sequence having a sequence homology of 80% or more, more preferably 90% or more, and even more preferably 95% or more with the base sequence of SEQ ID NO: 7, and may be located towards the 3' end of the polynucleotide sequence encoding the recombinant Zika virus envelope protein.

In addition, the polynucleotide encoding the HDEL tag is a gene including a base sequence of SEQ ID NO: 9, and is preferably a gene represented by SEQ ID NO: 9, but may include a base sequence having a sequence homology of 75% or more, more preferably 80% or more, and even more preferably 90% or more with the base sequence of SEQ ID NO: 9, and may be located towards the 3' end of the polynucleotide sequence encoding the recombinant Zika virus envelope protein.

Meanwhile, the polyhistidine tag may be fused with an HDEL tag, and a polynucleotide encoding the same is a gene including a base sequence of SEQ ID NO: 5, and is preferably a gene represented by SEQ ID NO: 5, but may include a base sequence having a sequence homology of 80% or more, more preferably 90% or more, and even more preferably 95% or more with the base sequence of SEQ ID NO: 5, and may be located towards the 3' end of the polynucleotide sequence encoding the recombinant Zika virus envelope protein.

In another exemplary embodiment of the present invention, the recombinant vector according to the present invention may be a recombinant vector in which the base sequence of SEQ ID NO: 3; the base sequence of SEQ ID NO: 2; and a polynucleotide encoding the amino acid sequence of SEQ ID NO: 4 or the base sequence of SEQ ID NO: 5 are sequentially linked. When linked in the order as described above, that is, when the expression cassette of Zika:Envl shown in the structure map (A) at the top of FIG. 1 is included, the recombinant vector according to the present invention includes a base sequence of SEQ ID NO: 11, and most preferably includes the base sequence of SEQ ID NO: 11, but may include a base sequence having a sequence homology of 80% or more, more preferably 90% or more, and even more preferably 95% or more with the base sequence of SEQ ID NO: 11.

In still another exemplary embodiment of the present invention, the recombinant vector according to the present invention may be a recombinant vector in which the base sequence of SEQ ID NO: 3; the base sequence of SEQ ID NO: 2; a polynucleotide encoding the amino acid sequence of SEQ ID NO: 6 or the base sequence of SEQ ID NO: 7; and a polynucleotide encoding the amino acid sequence of SEQ ID NO: 8 or the base sequence of SEQ ID NO: 9 are sequentially linked. When linked in the order as described above, that is, when the expression cassette of Zika:Env shown in the cleavage map (B) at the bottom of FIG. 1 is included, the recombinant vector according to the present invention includes a base sequence of SEQ ID NO: 13, and most preferably includes the base sequence of SEQ ID NO: 13, but may include a base sequence having a sequence homology of 80% or more, more preferably 90% or more, and even more preferably 95% or more with the base sequence of SEQ ID NO: 13.

As used herein, the "recombinant vector" refers to a vector capable of expressing a peptide or protein encoded by a foreign nucleic acid inserted into the vector, preferably a vector prepared so as to express a target antigen (in the present invention, the Zika virus envelope protein). The vector refers to any medium for the introduction and/or delivery of a base into a host cell in vitro, ex vivo, or in vivo, and may be a replicon to which another DNA fragment may be bound to bring about the replication of the bound fragment, and the replicon refers to any genetic unit (for example, a plasmid, a phage, a cosmid, a chromosome, a virus, and the like) that functions as an autonomous unit of DNA replication in vivo, that is, one which is capable of replication under its own control.

The recombinant vector of the present invention may preferably include a promoter, which is a transcription initiation factor to which RNA polymerase binds, any operator sequence for regulating transcription, a sequence encoding a suitable mRNA ribosome binding site and a sequence that regulates the termination of transcription and translation, a terminator, and the like, and may additionally include an NB gene, a polyhistidine-tag (an amino acid motif including at least 5 histidine residues), an endoplasmic reticulum signal peptide (meaning the same as an endoplasmic reticulum targeting sequence) gene, a cloning site, and the like. Further, the recombinant vector of the present invention may additionally include an Fc fragment of human immunoglobulin, a selection marker gene such as an antibiotic resistance gene for selecting a transformant, and the like.

As used herein, the "Fc fragment of a human immunoglobulin heavy chain (hFc)" refers to a portion which is linked only to a heavy chain (H chain) portion by an S—S bond and does not have any antigen binding site when immunoglobulin is digested by papain, and the Fc fragment of the present invention is preferably a human Fc fragment, and more preferably a human Fc fragment including the amino acid sequence of SEQ ID NO: 6 or a human Fc fragment encoded by the base sequence of SEQ ID NO: 7, but is not limited thereto. In addition, the Fc fragment of the present invention includes a variant of the base sequence represented by SEQ ID NO: 7 within the scope of the present invention. Specifically, the gene may include a base sequence having a sequence homology of 90% or more, more preferably 95% or more, and most preferably 98% or more to the base sequence of SEQ ID No. 7.

The "cloning site" is a general term for those inserted for the purpose of linking/separating each gene in a vector.

The "endoplasmic reticulum signal peptide (ER signal sequence)" is not limited in type and amino acid sequence as long as it is a plant endoplasmic reticulum signal peptide known to those skilled in the art, and for example, references such as US 20130295065 and WO2009158716 may be referred to. In an exemplary embodiment of the present invention, the endoplasmic reticulum signal peptide may be encoded by the base sequence (NB; new chaperone binding protein) of SEQ ID NO: 3, and the corresponding sequence after being translated into a protein may be partially or wholly removed.

The selection marker gene may include, for example, herbicide resistance genes such as glyphosate or phosphinothricin, antibiotic resistance genes such as kanamycin, G418, bleomycin, hygromycin, and chloramphenicol, aadA genes, and the like, the promoter may include, for example, a pEMU promoter, a MAS promoter, a histone promoter, a Clp promoter, a cauliflower-mosaic-virus-derived 35S promoter, a cauliflower-mosaic-virus-derived 19S RNA promoter, an actin protein promoter of a plant, a ubiquitin protein promoter, a cytomegalovirus (CMV) promoter, a simian virus 40 (SV40) promoter, a respiratory syncytial virus (RSV) promoter, an elongation factor-1 alpha (EF-1a) promoter, and the like, representative examples of the terminator include a nopaline synthase (NOS) terminator, a rice amylase RAmy 1 A terminator, a phaseolin terminator, a terminator of an octopine gene of *Agrobacterium tumefaciens*, a rrnB1/B2 terminator of *E. coli*, and the like, but the examples are only illustrative and are not limited thereto.

As still another aspect of the present invention, the present invention provides a transformant transformed with the aforementioned recombinant vector.

In an exemplary embodiment of the present invention, the transformant may be a microorganism such as *Escherichia coli, Bacillus, Salmonella*, and yeast, an animal cell including an insect cell and a human cell, an animal such as a mouse, a rat, a dog, a monkey, a pig, a horse, and a cow, *Agrobacterium tumefaciens*, a plant, and the like, the plant may be food crops including rice, wheat, barley, corn, soybean, potato, red bean, oats, and sorghum; vegetable crops including thale-cress, Chinese cabbage, white radish, peppers, strawberry, tomatoes, watermelon, cucumber, cabbage, oriental melon, pumpkin, spring onion, onion, and carrot; specialty crops including ginseng, tobacco, cotton, sesame, sugarcane, sugar beet, perilla, peanut, and rapeseed; fruits including apples, pears, jujubes, peaches, grapes, tangerines, persimmons, plums, apricots, and bananas; flowering plants including roses, carnations, chrysanthemums, lilies, and tulips, and the like, but is not limited thereto as long as it may be an organism which may be transformed with the vector of the present invention.

As used herein, "transformation" collectively refers to changes in the genetic properties of a living organism by injected DNA, the "transgenic organism" is an organism prepared by injecting an external gene by a molecular genetic method, preferably, an organism transformed by a recombinant expression vector of the present invention, and the organism is not limited as long as it is a living organism such as a microorganism, a eukaryotic cell, an insect, an animal, and a plant, and is preferably *Escherichia coli, Salmonella, Bacillus*, yeast, an animal cell, a mouse, a rat, a dog, a monkey, a pig, a horse, a cow, *Agrobacterium tumefaciens*, a plant, and the like, but is not limited thereto.

In the present specification, any plant can be used without limitation as long as it is a plant capable of mass-producing a protein including the recombinant Zika virus envelope protein of the present invention, may be more specifically selected from the group consisting of tobacco, thale-cress, corn, rice, soybean, canola, alfalfa, sunflower, sorghum, wheat, cotton, peanut, tomatoes, potato, lettuce and peppers, and may be preferably tobacco. The tobacco in the present invention is not particularly limited in type as long as it is a plant of the *Nicotiana* genus and can overexpress a protein, and the present invention can be carried out by selecting an appropriate variety according to the transformation method and the purpose of mass production of the protein. For example, a variety such as *Nicotiana benthamiana* L. or *Nicotiana tabacum* cv. *Xanthi* may be used.

The transformant may be prepared by a method such as transformation, transfection, *Agrobacterium*-mediated transformation, particle gun bombardment, sonication, electroporation, and polyethylene glycol (PEG)-mediated transformation, but there is no limitation as long as it is a method capable of injecting the vector of the present invention.

As yet another aspect of the present invention, the present invention may provide a recombinant Zika virus envelope protein prepared using the recombinant vector according to the present invention.

In an exemplary embodiment of the present invention, the recombinant Zika envelope protein may consist of the amino acid sequence of SEQ ID NO: 10 or 12, but is not limited thereto.

As yet another aspect of the present invention, the present invention may provide a method for producing a recombinant Zika virus envelope protein, the method including: (a) culturing the transformant; and (b) isolating and purifying a recombinant Zika virus envelope protein from the transformant or culture solution.

In an exemplary embodiment of the present invention, the purification in Step (b) may be performed using a water-soluble fraction, but is not limited thereto.

Mode for Invention

Hereinafter, preferred examples for helping with understanding of the present invention will be suggested. However, the following examples are provided only so that the present invention may be more easily understood, and the content of the present invention is not limited by the following examples.

EXAMPLES

Experimental Materials and Methods

1. Combination of Antigen and Adjuvant and Small Animal Immunity Test

Since recombinant subunit vaccines are easily degraded in the body and antigen-presenting is not continuously performed, therefore, because a potency persistence problem is likely to occur, it is essential to use an immune enhancer. Therefore, alum and TLR4-series monophosphoryl-lipid A (MPL) approved for use in human vaccines were selected as immune enhancer candidate materials, and tests were conducted to select the most effective antigen and adjuvant combination and concentration.

In 8-week-old C57BL/6 female mice, 10 to 50 μg/mouse of each recombinant vaccine candidate material, 50 to 500 μg/mouse of the immune enhancer alum, and 20 μg/mouse of MPL were mixed in PBS such that the total volume per mouse was 140 μl and the mixture was intramuscularly injected 1 to 3 times (Day 0, 14, and 42). The vaccine candidate materials (Zika virus recombinant antigen) are as follows: a Zika virus envelope protein fused with polyhistidine and HDEL (hereinafter, referred to as 'Zika:Envl') and a Zika virus envelope protein fused with hFc and HDEL (hereinafter, referred to as 'Zika:Env').

2. Humoral Immunoassay Test 2.1. Comparison of Antibody Production According to Vaccination Antibodies recognizing the vaccine candidates Zika:Envl and Zika:Env were measured using an indirect ELISA method developed in-house to evaluate the production of the target level of antibody during vaccine administration. After inoculation by intramuscular injection of PBS or vaccine candidate materials into mice (C57BL/6, female, 8 weeks old), blood was collected from the mice 7 to 14 days later (Day-1, 7, 28, and 49), and serum was separated. Each of the vaccine candidates (Zika:Envl, Zika:Env) was aliquoted into plates (Nunc-Immuno Plates; Thermo Scientific, UK) at 0.1 μg/well, and reacted at 4° C. for at least 16 hours, and then washed with a wash buffer (0.05% Tween20 in PBS), and then a blocking buffer (1% BSA in PBS) was aliquoted at 200 μl per well and reacted at 37° C. for 2 hours to alleviate non-specific binding. Subsequently, the vaccine candidate was washed with a wash buffer, and serum obtained from the mouse was binary diluted from 1:100 in a dilution buffer (0.1% BSA in PBS) and aliquoted into wells. After reaction at 37° C. for 2 hours, the serum was washed with a wash buffer to remove the serum sample, and then 100 μl of goat anti-mouse IgG-heavy and light chain antibody HRP conjugated (Bethyl Laboratories, USA) diluted 1:10,000 was aliquoted and reacted at 37° C. for 1 hour. After washing with a wash buffer, color was developed with a TMB (Surmodics, USA) solution, and absorbance was measured at 450 nm.

2.2. Comparison of Subtype IgG1 and IgG2c Production According to Vaccination

In order to compare the subtypes of antibodies produced during vaccine administration, a subtype IgG1 and IgG2c comparison experiment was conducted using the indirect ELISA method developed in-house. Mice (C57BL/6, female, 8 weeks old) were intramuscularly administered the vaccine candidates 1 to 3 times (Day-0, 14, and 42), and after 7 to 14 days (Day-1, 7, 28, and 49), blood was collected from the mice, and serum was separated. Each of the vaccine candidates (Zika:Envl, Zika:Env) was aliquoted into plates (Nunc-Immuno Plates; Thermo Scientific) at 0.1 μg/well, and reacted at 4° C. for at least 16 hours, and then washed with a wash buffer (0.05% Tween20 in PBS), and then a blocking buffer (1% BSA in PBS) was aliquoted at 200 μl per well and reacted at 37° C. for 2 hours to alleviate non-specific binding. Subsequently, the vaccine candidate was washed with a wash buffer, and serum obtained from the mouse was diluted 1:100 or 1:400 in a dilution buffer (0.1% BSA in PBS) and aliquoted into wells. After reaction at 37° C. for 2 hours, the serum was washed with a wash buffer to remove the serum sample, and then 100 μl of each of goat anti-mouse IgG1 (Bethyl Laboratories, USA) diluted 1:10,000 and goat anti-mouse IgG2c HRP (Southern Biotech, USA) diluted 1:8,000 to detect subtypes IgG1 and IgG2c was aliquoted and reacted at 37° C. for 1 hour. After washing with a wash buffer, color was developed with a TMB (Surmodics, USA) solution, and absorbance was measured at 450 nm.

3. Neutralizing Antibody Evaluation Test—Evaluation of Neutralizing Antibody Inducing Ability According to Vaccination Neutralizing antibodies produced during vaccine administration were measured using a plaque reduction neutralization test (PRNT). Mice (C57BL/6, female, 8 weeks old) were intramuscularly administered the vaccine candidates or PBS 3 times (Day-0, 14, and 42), and after 7 days (Day-49), blood was collected from the mice, and serum was separated. The serum of 5 mice of the same group was pooled and used, and after being non-assimilated at 56° C. for 30 minutes, the control serum and the experimental group serum were diluted at the same dilution rate, respectively. About 50 plaques/well were prepared from the virus control by diluting two Zika viruses (MR766 and PRVABC59 strains) whose titers (PFU/ml) were confirmed, and then mixed with the diluted serum 1:1 and the resulting mixture was reacted at 37° C. for 30 minutes. After virus reaction for 30 minutes, the serum and virus reaction solution were inoculated into Vero cells or Vero 76 cells, and then after adsorption for 2 hours, overlay media (1% sea plaque agar or 1.4% methyl cellulose) was added and incubated in a 37° C. and $CO_2$ incubator for 5 or 14 days, and then stained with 1% crystal violet to confirm the number of plaques. $PRNT_{50}$ was calculated through % inhibition.

4. Cellular Immune Cytokine Measurement Test 4.1 Isolation of Splenocytes

After inoculating mice (C57BL/6, female, 8 weeks old) with PBS or a vaccine candidate once (Day-0), the spleen was removed on the seventh day (Day-7), or after inoculation twice or three times (Day-14, 42), the spleen was removed on the third day (Day-17, 45). The removed spleen was placed in cold RPMI 1640 medium, the spleen was disrupted using a 5 ml syringe, and then flowed into a 40 μm nylon cell strainer (BD Biosciences, USA) to separate splenocytes. After centrifuging the obtained cells at 2,000 rpm for 10 minutes, the centrifuged cells were treated with RBC lysis buffer for 2 minutes to remove red blood cells. After removing the RBC lysis buffer by centrifugation, the cells were suspended in RPMI 1640 (10% FBS, 1% penicillin-streptomycin) and used for ELISPOT, ELISA and flow cytometry experiments.

4.2. Cytokine-Producing Immune Cell Analysis

In order to evaluate the production of representative cytokines required for cell-mediated defense during vaccine administration, ELISPOT was used to evaluate whether immune cells producing IFN-γ and IL-12 was increased. After inoculating mice (C57BL/6, female, 8 weeks old) with PBS or a vaccine candidate once (Day 0), the spleen was removed on the seventh day (Day-7), or after inoculation twice or three times (Day-14, 42), the spleen was removed on the third day (Day-17, 45). Splenocytes were isolated from the spleen, stimulated with 1 μg/ml of an antigen (Zika:Envl or Zika:Env), and cultured on ELISPOT plates for 48 hours. IFN-γ and IL-12 ELISPOT were performed using a BDA™ ELISPOT mouse IFN-γELISPOT set (BD Life Sciences, USA) and mouse IL-12 (p70) ELISpotBASIC (MABTECH, USA), respectively, according to the manufacturer's instructions.

To perform IFN-γ ELISPOT, the IFN-γ capture antibody was diluted 1:200 and added at 100 μl/well, and then reacted at 4° C. for 16 hours. After washing three times with a wash buffer, 200 μl/well of a blocking reagent (RPMI 1640, 10% FBS) was added, and the resulting mixture was reacted at room temperature for 2 hours. After washing again with a wash buffer three times, splenocytes were aliquoted at $5\times10^5$ cells/well, and antigens (vaccine candidate materials Zika: Envl, Zika:Env) were treated at a concentration of 1 μg/ml and incubated in an incubator at 37° C., 5% $CO_2$. After antigen treatment for 48 hours and then washing three times with a wash buffer, a detection antibody was diluted 1:250 with a dilution buffer (10% FBS in PBS), added at 100 μl/well, and then reacted at room temperature for 2 hours. After washing three times with a wash buffer, streptavidin-HRP was diluted 1:100 and added at 100 μl/well, and then reacted at room temperature for 1 hour. Subsequently, after washing three times with a wash buffer, the resulting product was washed twice with PBS, the color reaction was observed using a BD AEC substrate set (BD Life Sciences, USA), and the reaction was stopped by washing the wells with DDW, and then the wells were dried in air, and then the spots of each well were counted and analyzed.

In order to perform IL-12 ELISPOT, the IL-12 capture antibody was diluted to 15 μg/ml and added at 100 μl/well, and then reacted at 4° C. for 16 hours. After washing four times with PBS, 200 μl/well of a blocking reagent (RPMI 1640, 10% FBS) was added and reacted at room temperature for 1 hour. After washing again with PBS four times, splenocytes were aliquoted at $5\times10^5$ cells/well, and antigens (vaccine candidate materials Zika:Envl, Zika:Env) were treated at a concentration of 1 μg/ml and incubated in an incubator at 37° C., 5% $CO_2$. After washing four times with PBS, the detection antibody was diluted to 1 μg/ml and added at 100 μl/well, and then reacted at room temperature for 2 hours. After washing three times with PBS, streptavidin-HRP was diluted 1:100 and added at 100 μl/well, and then reacted at room temperature for 1 hour. Subsequently, after washing five times with PBS, the color reaction was observed using a BD AEC substrate set (BD Life Sciences), and the reaction was stopped by washing the wells with DDW, and then the wells were dried in air, and then the spots of each well were counted and analyzed.

4.3. Evaluation of Production Amount of Cytokine

The production amount of cytokines was evaluated using ELISA kits. After inoculating mice (C57BL/6, female, 8 weeks old) with PBS or a vaccine candidate once (Day-0), the spleen was removed on the seventh day (Day-7), or after inoculation twice or three times (Day 14, 42), the spleen was removed on the third day (Day-17, 45). Splenocytes were isolated from the spleen, aliquoted at $5\times10^5$ cells/well in a 96-well cell culture plate, and restimulated with an antigen (vaccine candidate material Zika:Envl or Zika:Env) corresponding to a concentration of 1 μg/ml, and then the production of cytokines was analyzed by ELISA analysis using a cell culture medium at 48 hours. The measurement of cytokines (IFN-γ, IL-12, IL-4, TNF-α) secreted into the cell culture medium was performed using a mouse IFN-γ ELISA MAX™ standard set, a mouse IL-12 ELISA MAX™ standard set, a mouse IL-4 ELISA MAX™ standard set, a mouse TNF-α ELISA MAX™ standard set (BioLegend, USA) according to the manufacturer's instructions.

The capture antibody corresponding to each cytokine was diluted 1:200 and added to plates (Nunc-Immuno Plates; Thermo Scientific) at 100 μl/well, and then reacted at 4° C. for 16 hours. After washing four times with a wash buffer, the resulting product was reacted with 10% FBS (in PBS), which is a blocking reagent, for 1 hour. After washing four times with a wash buffer, 100 μl of each cell culture solution was added, and the resulting mixture was reacted at room temperature for 2 hours. After washing four times with a wash buffer, 100 μl/well of the detection antibody diluted 1:200 was added, and the resulting mixture was reacted at room temperature for 1 hour. Subsequently, after washing four times with a wash buffer, 100 μl/well of avidin-HRP diluted 1:1,000 was added, and then the resulting mixture was reacted at room temperature for 30 minutes. After washing five times with a wash buffer, 100 μl of TMB solution was added, reacted for 15 minutes while blocking light, and absorbance was measured at 450 nm. A standard curve corresponding to each cytokine was prepared using each purified antigen serially diluted, and the concentration of each cytokine was calculated according to the prepared standard curve.

4.4. Immune Cell Response Analysis

For analysis of immune cells activated at the time of vaccination, effector T cells ($CD3^+$, $CD4^+$, and $CD8^+$), exhausted T cells ($PD\text{-}1^+$) and $T_{reg}$ cells ($CD4^+$, $CD25^+$, and $Foxp3^+$) were analyzed in splenocytes isolated from the mice inoculated with each vaccine candidate using flow cytometry.

After inoculating mice (C57BL/6, female, 8 weeks old) with PBS or a vaccine candidate once (Day-0), the spleen was removed on the seventh day (Day-7), or after inoculation three times (Day-42), the spleen was removed on the third day (Day-45). The removed spleen was placed in cold RPMI 1640 medium, the spleen was disrupted using a 5 ml syringe, and then flowed into a 40 μm nylon cell strainer (BD Biosciences) to separate splenocytes. The obtained spleen immune cells were suspended in MACS buffer (0.5% BSA+2 mM EDTA in PBS) such that the cell concentration was $1\times10^6$ cells/ml.

For effector T cells ($CD3^+$, $CD4^+$, and $CD8^+$) and exhausted T cells (PD-$1^+$), the antibodies shown in the following Table 1 were used, and all antibodies used in the experiment were purchased from BioLegend. After removing the supernatant by centrifuging the cell suspension at 4° C. and 6,000 rpm for 5 minutes, 50 μl of an antibody diluted 1:250 was added to each group, followed by reaction at 4° C. for 20 minutes. After 20 minutes, 500 μl of MACS buffer was added and centrifuged at 4° C. and 6,000 rpm for 5 minutes. The supernatant was removed, fixed with 400 μl of 0.4% PFA (in PBS), and measured by flow cytometry.

For $T_{reg}$ cells ($CD4^+$, $CD25^+$, and $Foxp3^+$), the antibodies shown in the following Table 1 were used, and all antibodies used in the experiment were purchased from BioLegend. After removing the supernatant by centrifuging the cell suspension at 4° C. and 6,000 rpm for 5 minutes, 50 μl of each of $CD4^+$ and $CD25^+$ antibodies diluted 1:250 was added to each group, followed by reaction at 4° C. for 20 minutes. After 20 minutes, 500 μl of MACS buffer was added and centrifuged at 4° C. and 6,000 rpm for 5 minutes. The supernatant was removed and mixed with a Foxp3/transcription factor staining buffer set at a 3:1 ratio (diluent: concentrate), and then 200 μl of each sample was added to suspend the cells, and reaction was performed at 4° C. for 1 hour. 800 μl of MACS buffer was added and centrifuged at 4° C. and 6,000 rpm for 5 minutes. The supernatant was removed, the Foxp3/transcription factor staining buffer set and a 10× permeabilization buffer were diluted to 1× in distilled water, and then 200 μl of the diluted solution was added to each sample to suspend cells, and then centrifugation was performed at 4° C. and 6,000 rpm for 5 minutes. After removing the supernatant, 50 μl of 1× permeabilization buffer in which a Foxp3 antibody was diluted 1:500 was added to each sample, and the resulting mixture was reacted at 4° C. for 20 minutes. After washing with 800 μl of 1× permeabilization buffer, centrifugation was performed at 4° C. and 6,000 rpm for 5 minutes. The supernatant was removed, fixed with 400 μl of 0.4% PFA (in PBS), and measured by flow cytometry. As a flow cytometer, a FACS Calibur (BD Biosciences, USA) was used, and 10,000 cells per sample were analyzed.

TABLE 1

Flow cytometry antibody dilution ratio

| Target | Dye | Dilution ratio |
|---|---|---|
| CD3 | FITC | 1:250 |
| CD4 | PE | 1:250 |
| CD8 | PE/cy7 | 1:250 |
| CD279 (PD-1) | APC/cy7 | 1:250 |
| CD25 | APC | 1:250 |
| Foxp3 | PE/cy7 | 1:500 |

5. Protective Efficacy Evaluation Test 5.1. Maternal Antibody Evaluation

Mice (C57BL/6, female, 8 weeks old) were inoculated three times (Day-0, 14, and 42) with a vaccine candidate by intramuscular injection and mated, and then blood was collected from two-day-old offspring mice, which were born to mothers inoculated with the vaccine candidate, and serum was separated. Each of the vaccine candidate materials (Zika:Envl, or Zika:Env) was aliquoted into plates (Nunc-Immuno Plates; Thermo Scientific) at 0.1 μg/well, and reacted at 4° C. for at least 12 hours, and then washed with a wash buffer (0.05% Tween20 in PBS), and a blocking buffer (1% BSA in PBS) was aliquoted at 200 μl per each well and reacted at 37° C. for 2 hours to alleviate non-specific binding. Subsequently, the vaccine candidate material was washed with a wash buffer, and serum obtained from the offspring mouse was binary diluted from 1:100 in a dilution buffer (0.1% BSA in PBS) and aliquoted into each well. After reaction at 37° C. for 2 hours, the serum was washed with a wash buffer to remove the serum sample, and then 100 μl of goat anti-mouse IgG-heavy and light chain antibody HRP conjugated (Bethyl Laboratories) diluted 1:10,000 was aliquoted and reacted at 37° C. for 1 hour. After washing with a wash buffer, color was developed with a TMB (Surmodics, USA) solution, and absorbance was measured at 450 nm.

5.2. Analysis of Cytokine-Producing Immune Cells in Offspring Mice

Mice (C57BL/6, female, 8 weeks old) were inoculated with a vaccine candidate material three times (Day-0, 14, and 42) by intramuscular injection and mated, and then the spleens were removed from 30-day-old offspring mice born to mothers inoculated with the vaccine candidate. Splenocytes were isolated from the spleen, stimulated with an antigen (vaccine candidate material Zika:Envl or Zika:Env), and cultured on ELISPOT plates for 48 hours. As a negative control, spleen immune cells obtained by inoculating mice with PBS were used. IFN-γ and IL-12 ELISPOT were performed using a BD™ ELISPOT mouse IFN-γ ELISPOT set (BD Life Sciences) and mouse IL-12 (p70) ELISpotBASIC (MABTECH), respectively, according to the manufacturer's instructions.

To perform IFN-γ ELISPOT, the IFN-γ capture antibody was diluted 1:200 and added at 100 μl/well, and then reacted at 4° C. for 16 hours. After washing three times with a wash buffer, 200 μl/well of a blocking reagent (RPMI 1640, 10% FBS) was added, and the resulting mixture was reacted at room temperature for 2 hours. After washing three times with a wash buffer, splenocytes were aliquoted at $5\times10^5$ cells/well, and antigens (vaccine candidate materials Zika: Envl, Zika:Env) were treated at a concentration of 1 μg/ml and incubated in an incubator at 37° C., 5% $CO_2$ for 48 hours. After antigen treatment for 48 hours and then washing three times with a wash buffer, a detection antibody was diluted 1:25, added at 100 μl/well, and then reacted at room temperature for 2 hours. After washing again with a wash buffer three times, streptavidin-HRP was diluted 1:100 and added at 100 μl/well, and then reacted at room temperature for 1 hour. Subsequently, after washing three times with a wash buffer, the resulting product was washed twice with PBS, the color reaction was observed using a BD AEC substrate set (BD Life Sciences), and the reaction was stopped by washing the wells with DDW, and then the wells were dried in air, and then the spots of each well were counted and analyzed.

In order to perform IL-12 ELISPOT, the IL-12 capture antibody was diluted to 15 μg/ml and added at 100 μl/well, and then reacted at 4° C. for 16 hours. After washing four times with PBS, 200 μl/well of a blocking reagent (RPMI 1640, 10% FBS) was added and reacted at room temperature for 1 hour. After washing four times with a wash buffer, splenocytes were aliquoted at $5\times10^5$ cells/well, and antigens (vaccine candidate materials Zika:Envl, Zika:Env) were treated at a concentration of 1 μg/ml and incubated in an incubator at 37° C., 5% $CO_2$ for 48 hours. After washing again with PBS four times, the detection antibody was diluted to 1 μg/ml and added at 100 μl/well, and then reacted at room temperature for 2 hours. Subsequently, after washing three times with a wash buffer, streptavidin-HRP was diluted 1:100 and added at 100 μl/well, and reacted at room temperature for 1 hour. After washing five times with PBS, the color reaction was observed using a BD AEC substrate set (BD Life Sciences), and the reaction was stopped by washing the wells with DDW, and then the wells were dried in air, and then the spots of each well were counted and analyzed.

5.3. Evaluation of Production Amount of Cytokines in Offspring Mice

Mice (C57BL/6, female, 8 weeks old) were inoculated with a vaccine candidate material three times (Day-0, 14, and 42) by intramuscular injection and mated, and then the spleens were removed from 30-day-old offspring mice born to vaccinated mothers. Splenocytes were isolated from the spleen, aliquoted at $5\times10^5$ cells/well in a 96-well cell culture plate, and restimulated with an antigen (vaccine candidate material Zika:Envl or Zika:Env) corresponding to a concentration of 1 μg/ml, and then 48 hours later, the production of cytokines was analyzed by ELISA analysis. The measurement of cytokines (IFN-γ, IL-12, and TNF-α) secreted into the cell culture medium was performed using a mouse IFN-γ ELISA MAX™ standard set, a mouse IL-12 ELISA MAX™ standard set, and a mouse TNF-α ELISA MAX™ standard set (BioLegend) according to the manufacturer's instructions.

The capture antibody corresponding to each cytokine was diluted 1:200 and added to plates (Nunc-Immuno Plates; Thermo Scientific) at 100 μl/well, and then reacted at 4° C. for 16 hours. After washing four times with a wash buffer, the resulting product was reacted with 10% FBS (in PBS), which is a blocking reagent, for 1 hour. After washing again with a wash buffer four times, 100 μl of each cell culture solution was added, and the resulting mixture was reacted at room temperature for 2 hours. After washing four times with a wash buffer, 100 μl/well of the detection antibody diluted 1:200 was added, and the resulting mixture was reacted at room temperature for 2 hours. Subsequently, after washing four times with a wash buffer, 100 μl/well of avidin-HRP diluted 1:1,000 was added, and then the resulting mixture was reacted at room temperature for 30 minutes. After washing five times with a wash buffer, 100 μl of TMB solution was added, reacted for 15 minutes while blocking light, and absorbance was measured at 450 nm. A standard curve corresponding to each cytokine was prepared using each purified antigen serially diluted, and the concentration of each cytokine was calculated according to the prepared standard curve.

5.4. Protective Efficacy Evaluation

For mice (C57BL/6, female, 8 weeks old), a vaccine candidate material (Zika:Envl, or Zika:Env) at 10 to 50 μg/mouse and the immune enhancer alum 50 to 500 μg/mouse+MPL 20 μg/mouse were mixed in PBS such that the total volume for each mouse was 140 μl, inoculated three times (Day-0, 14, and 42) by intramuscular injection and mated, and then two Zika viruses (Puerto Rico-derived strain PRVABC59, Uganda-derived strain MR766) and dengue virus (type 2) were subcutaneously inoculated into 2-day-old offspring mice, which were born to mothers inoculated with the vaccine candidate material, to evaluate cross-protective efficacy, and clinical symptoms according to each virus were observed. The amount of each inoculated virus is summarized in the following Table 2, and subcutaneous inoculation was performed.

TABLE 2

Amount of virus inoculated.

| Virus name, strain | Distributor | Management No. | Virus titer ($TCID_{50}$/ml) | Inoculum volume ($TCID_{50}$/mouse) |
|---|---|---|---|---|
| Uganda ZIKV strain, MR766 | BEI resource | NR-50065 | $10^{7.8}$ | $10^{6.8}$ |
| Puerto Rico ZIKV strain, PRVABC59 | BEI resource | NR-50240 | $10^{8.3}$ | $10^{6.3}$ |
| Dengue fever virus-type 2 | National Culture Collection for Pathogens | 43253 | $10^8$ | $10^6$ |

Example 1: Preparation of Recombinant Zika Virus Envelope Protein Plant Expression Vector As shown in FIG. 1, a recombinant plant expression vector was constructed such that the Zika virus envelope protein could be expressed in plants. In more detail, the genetic information on the Zika virus envelope protein was obtained, and a gene (SEQ ID NO: 2) was synthesized with a sequence optimized for expression in *Nicotiana benthamiana.*

To obtain a Zika:Envl recombinant antigen, a polynucleotide (SEQ ID NO: 3) encoding a new chaperone binding protein (NB) between the CaMV 35S promoter of the pCAMBIA1300 vector and a heat shock protein (HSP) terminator, a polynucleotide (SEQ ID NO: 2) encoding the Zika virus envelope protein, polyhistidine, and a polynucleotide (SEQ ID NO: 5) encoding His-Asp-Glu-Leu (HDEL) were sequentially ligated to construct a Zika virus envelope protein plant expression vector. The vector thus constructed includes a base sequence of SEQ ID NO: 11.

To obtain a Zika:Env recombinant antigen, a polynucleotide (SEQ ID NO: 3) encoding a new chaperone binding protein (NB) between the CaMV 35S promoter of the pCAMBIA1300 vector and a HSP terminator, a polynucleotide (SEQ ID NO: 2) encoding the Zika virus envelope protein, a polynucleotide (SEQ ID NO: 7) encoding an Fc fragment of a human immunoglobulin heavy chain and a polynucleotide (SEQ ID NO: 9) encoding a His-Asp-Glu-Leu (HDEL) peptide were sequentially ligated to construct a Zika virus envelope protein plant expression vector. The vector thus constructed includes a base sequence of SEQ ID NO: 13.

Example 2: Confirmation of Expression of Recombinant Zika Virus Envelope Protein 2.1. Transient Expression of Plant Expression Vector An *Agrobacterium* LBA4404 strain was transformed with each of the two plant expression vectors prepared in Example 1 using an electric shock method (electroporation). After the transformed agrobacteria were shaken and cultured in 5 mL of a yeast extract peptone (YEP) liquid medium (10 g of yeast extract, 10 g of peptone, 5 g of NaCl, 50 mg/L canamycin, and 25 mg/L rifampicin) under the condition of 28° C. for 16 hours, 1 ml of a primary culture medium was inoculated into 50 ml of a fresh YEP medium and shaken and cultured under the condition of 28° C. for 6 hours. The agrobacteria cultured as described above were collected by centrifugation (7,000 rpm, 4° C., 5 minutes), and then suspended again in an infiltration buffer [10 mM MMES (pH 5.7), 10 mM $MgCl_2$, and 200 μM acetosyringone] at a concentration of O.D. 1.0 at a wavelength of 600 nm. Agro-infiltration was performed by a method of injecting the agrobacterial suspension into the backside of *Nicotiana benthamiana* leaves using a syringe from which the injection needle had been removed.

2.2. Confirmation of Expression of Recombinant Zika Virus Envelope Protein in Plants After extracting proteins from the plant leaf prepared in Example 2.1 and centrifuging the same, the proteins in the aqueous fraction (S) and the proteins in the pellet (P) fraction included in the solution were confirmed by western blotting with the whole extract before centrifugation (total; T). More specifically, 30 μl of each fraction was mixed with SDS sample buffer and then heated. Then, proteins were separated by size by performing electrophoresis on a 10% SDS-PAGE gel, the separated proteins were transferred to a PVDF membrane, and then subjected to a blocking step using 5% skim milk, and then bound to secondary antibodies bound to hFc, and treated with an ECL solution by the method provided by the manufacturer, thereby confirming a recombinant Zika:Env protein. The results are shown in FIG. 2.

Figure 2:
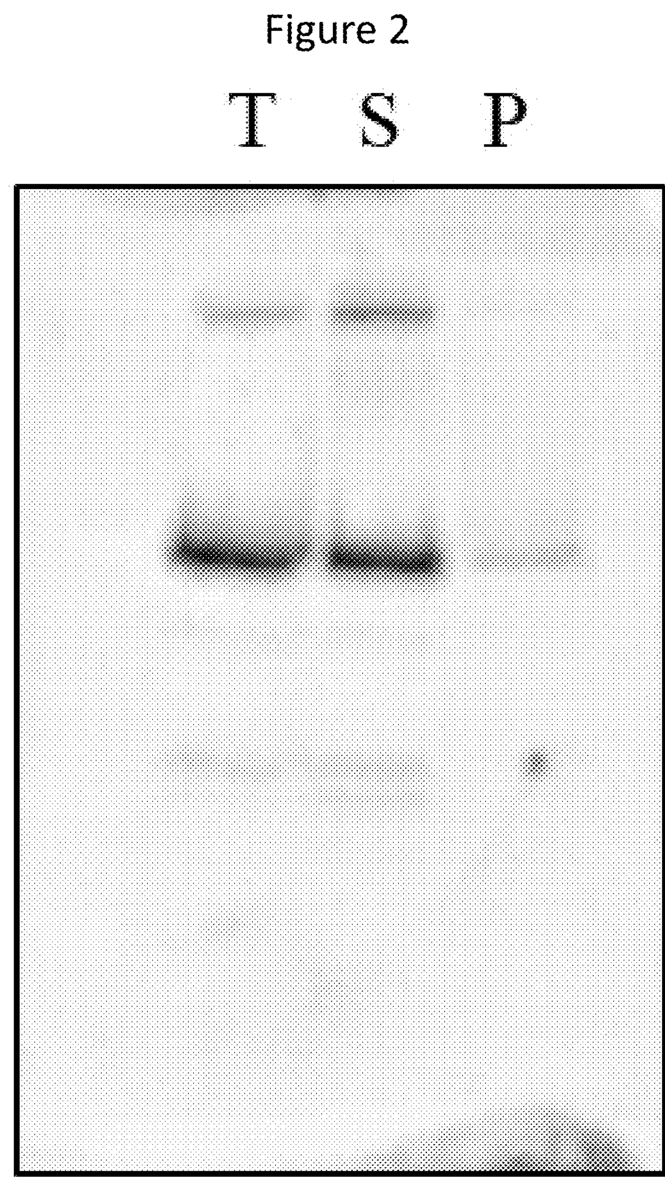
FIG. 2 is a view illustrating the results of expressing the Zika virus envelope protein in a plant and confirming the same by western blotting (T, total fraction; S, water-soluble fraction; P, pellet fraction).

As shown in FIG. 2, most of the expressed recombinant Zika:Env protein was confirmed in the aqueous fraction, and a small amount of recombinant Zika virus envelope protein was observed in the pellet fraction. These results were shown to be the same for the recombinant Zika:Envl protein.

Through the results, it could be confirmed that a vector for expressing a recombinant Zika virus envelope protein of the present invention could effectively express a recombinant Zika virus envelope protein in plants, a recombinant Zika virus envelope protein prepared using the vector has high water solubility, and thus is easy to isolate and purify, and the aggregation of the recombinant protein was suppressed, thereby being effective for maintaining the physiological activity or pharmacological activity of the recombinant protein.

Figure 3:
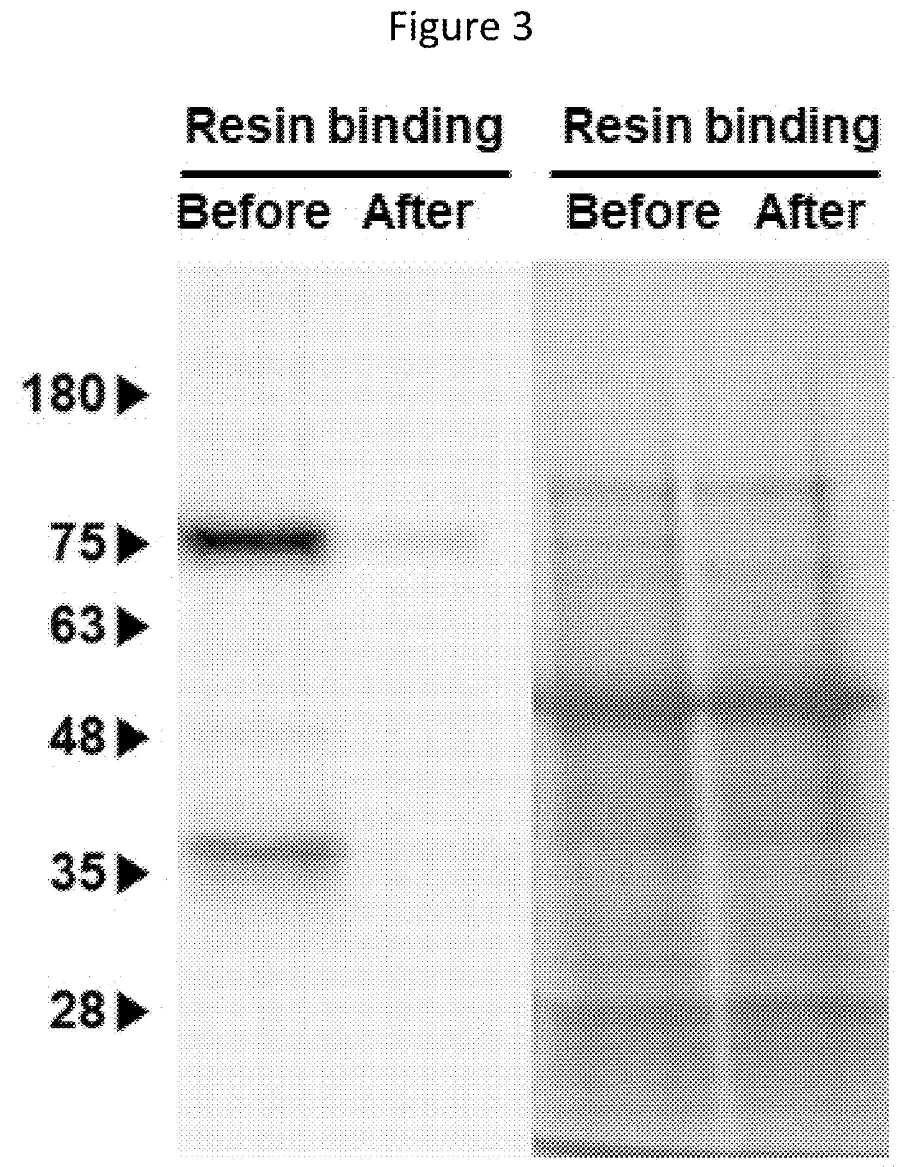
FIG. 3 is a view illustrating the results of confirming the presence or absence of binding to a resin during the process of isolating and purifying the recombinant Zika virus envelope protein from a plant by western blotting.

Example 3: Isolation and Purification of Recombinant Zika Virus Envelope Protein 1 L of a protein extraction solution [50 mM sodium phosphate (pH 8.0), 300 mM NaCl, 100 mM sodium sulfite, 0.5% Triton X-100, 1.5% PVPP] was added to 500 g of *Nicotiana benthamiana* leaves expressing the recombinant Zika virus envelope protein prepared in Example 2, and tissue was disrupted with a blender, followed by centrifugation at 10,000 rpm at 4° C. for 40 minutes to recover a protein extract solution. Affinity chromatography was performed with a column packed with a Protein A agarose resin for the isolation and purification of the recombinant Zika virus envelope protein from the protein extract solution. For resin equilibration, the column was filled with 50 mL of resin and then equilibrated with 500 mL of wash solution 2 [50 mM sodium phosphate (pH 8.0), 300 mM NaCl]. After combining the recovered protein extract solution with the equilibrated resin, the resin was washed with 250 mL of wash solution 1 [50 mM sodium phosphate (pH8.0), 300 mM NaCl, 0.5% Triton X-100], and washed with 250 mL of wash solution 2 [50 mM sodium phosphate (pH 8.0), 300 mM NaCl]. After washing was completed, the recombinant Zika:Env protein was eluted with an elution solution [100 mM sodium citrate (pH 3.0), 300 mM NaCl]. To the elution solution including the recombinant Zika:Env protein, a neutralizing solution [1.5 M Tris-Cl (pH 8.8)] was added until the pH became 7.4 for protein stabilization. The elution solution including the recombinant Zika:Env protein was buffer-exchanged and concentrated with a storage solution [50 mM Tris-Cl (pH 7.4), 300 mM NaCl] using a ultrafiltration (UF) system using a 50 kDa membrane filter. The binding of the recombinant Zika virus envelope protein to the resin was confirmed by western blotting (see FIG. 3), and successful isolation and purification of the isolated and purified recombinant Zika virus envelope protein was confirmed by Coomassie staining after electrophoresis (SDS-PAGE) (see FIG. 4).

Through the above results, it could be confirmed that the recombinant Zika virus envelope protein of the present invention can be used as a novel Zika virus vaccine composition because the recombinant Zika virus envelope protein of the present invention can not only be effectively expressed even in plants, but also has high water solubility, and thus is easily isolated and purified, and also acts as an antigen in vivo to exhibit high immunogenicity and virus neutralizing ability. Hereinafter, the effect of combining two types of the Zika virus envelope proteins and an adjuvant (immune enhancer) was evaluated with various items to search for the most effective vaccine composition.

Example 4: Candidate Selection of Vaccines Containing Recombinant Zika Virus Envelope Protein and Adjuvants By selecting Zika virus vaccine candidates (Zika:Envl and Zika:Env) expressed in a plant (*Nicotiana benthamiana*), alum, which induces a Th2-type immune response and enhances antigen presentation as an adjuvant candidate, and monophosphoryl-lipid A (MPL), which is known to induce a Th1-type immune response as a toll-like receptor (TLR) 4 agonist), experiments were performed with the combinations shown in the following Table 3 (Groups 1 to 6 are classified according to each combination).

Figures 4, 5:
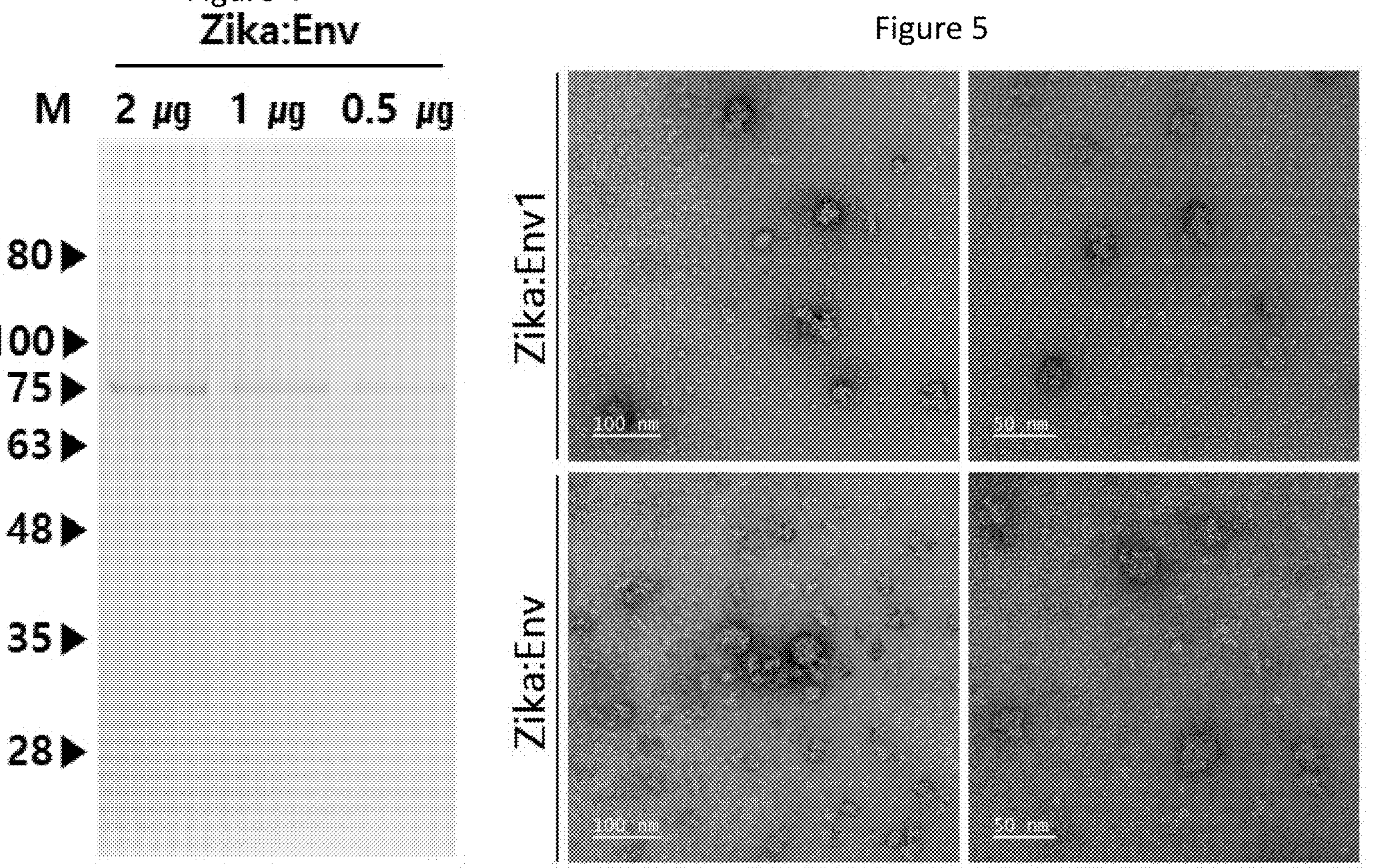
FIG. 4 is a view of confirming a recombinant Zika virus envelope protein isolated and purified from a plant by Coomassie staining after electrophoresis (SDS-PAGE).
FIG. 5 is a set of transmission electron micrographs of two recombinant Zika virus envelope proteins (top, Zika: Envl; bottom, Zika:Env).

Although it was confirmed using transmission electron microscopy (TEM) whether vaccine candidates (Zika:Envl, Zika:Env) showed a virus like particle (VLP) morphology, neither of the two recombinant envelope proteins showed the VLP morphology as can be seen in FIG. 5.

TABLE 3

Zika virus vaccine candidates.

| Group | Vaccine (μg/mouse) | Adjuvant |
|---|---|---|
| 1 | PBS | — |
| 2 | Zika:Env1 (50 μg) | Alum (50 μg) |
| 3 | Zika:Env (50 μg) | Alum (50 μg) |
| 4 | Zika:Env1 (50 μg) | Alum (50 μg) + MPL (20 μg) |
| 5 | Zika:Env (50 μg) | Alum (50 μg) + MPL (20 μg) |
| 6 | Zika:Env (10 μg) | Alum (500 μg) + MPL (20 μg) |

Comparative Example 1: Humoral Immunity Evaluation 1.1. Comparison of Antibody Production According to Vaccination Antibodies recognizing the vaccine candidates Zika:Envl and Zika:Env were measured using the indirect ELISA method developed in-house to evaluate whether a target level of antibody is produced during vaccine administration. Zika virus antibodies in serum isolated from mice 7 to 14 days (Day-1, 7, 28, and 49) after intramuscular injection of PBS or vaccine candidates 1 to 3 times (Day-0, 14, and 42) into mice were measured (see the flowchart of FIG. 6A).

Figures 6, 6C:
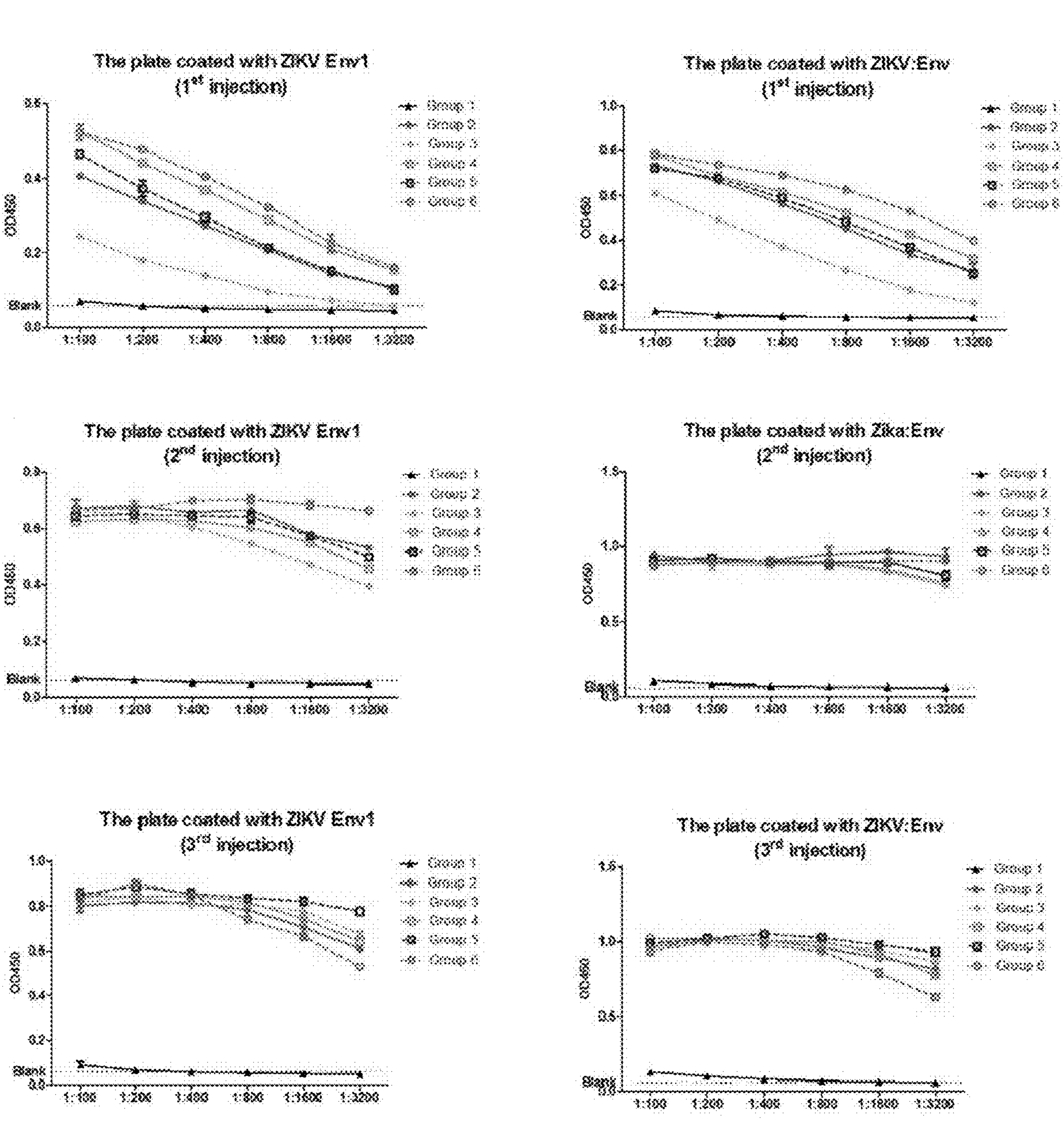

As a result of antibody titer measurement, as shown in FIGS. 6B and 6C, when the vaccine candidate was repeatedly inoculated 2 to 3 times, the antibody titers of all groups except for the negative control (PBS; Group 1) were similarly measured, but at the time of one inoculation, the antibody titer of the MPL-mixed group (Groups 4 to 6) was even higher. Based on this, it was confirmed that a faster immune response was induced in humoral immunity when MPL was mixed.

1.2. Comparison of Subtype IgG1 and IgG2c Production According to Vaccination

The induction of Th1 and Th2 cell-mediated immune responses was confirmed by inoculating vaccine candidates 1 to 3 times (Day-0, 14, and 42) and diluting sera obtained 7 to 14 days later (Day-1, 7, 28, and 49) at a ratio of 1:100 or 1:400 to perform comparative analysis of the IgG1 and IgG2c subtypes of the antibody through the indirect ELISA method developed in-house.

Figure 7:
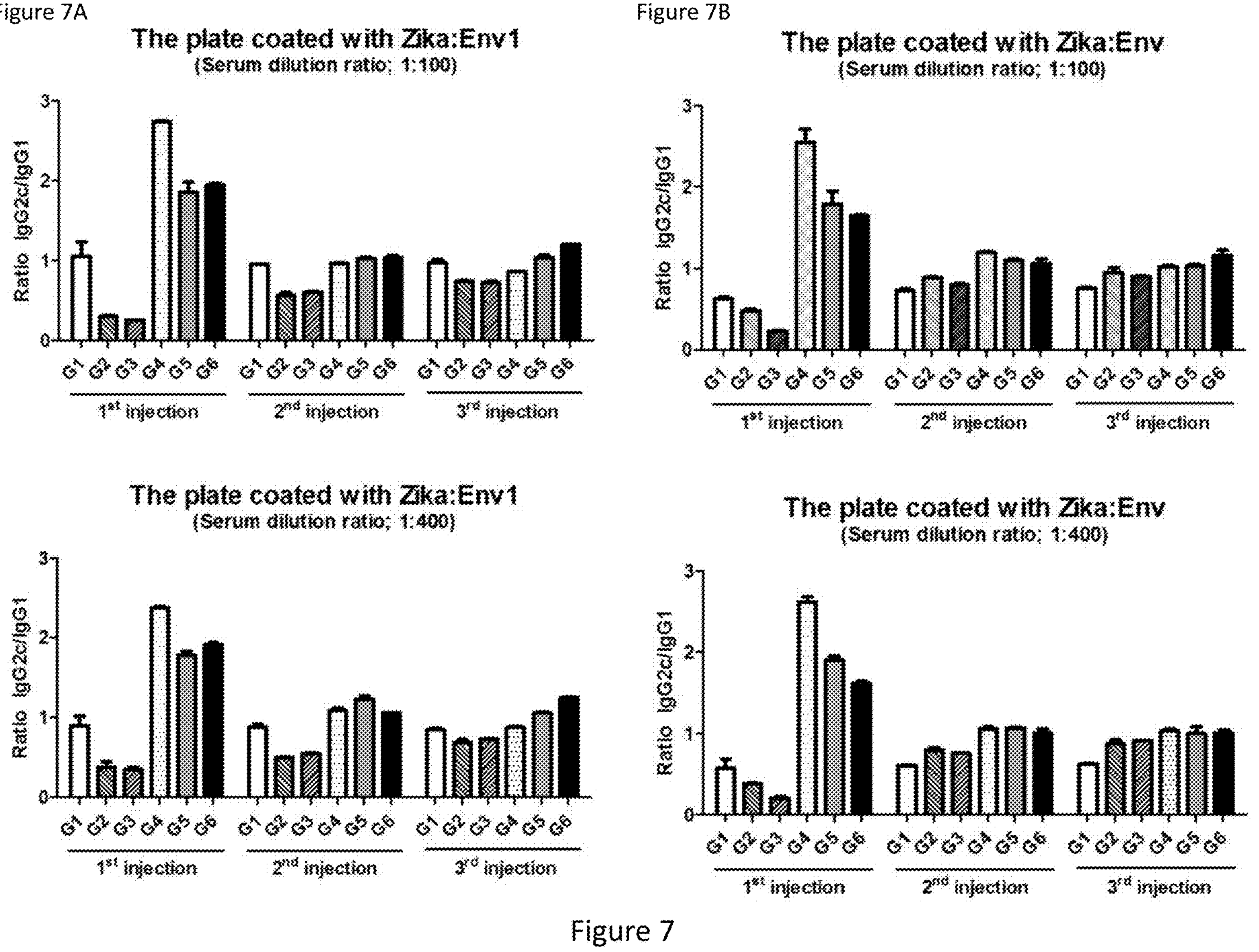
FIGS. 7A and 7B are views illustrating the results of measuring the Th1/Th2 IgG isotype ratios through indirect ELISA by inoculating mice with the vaccine composition according to the present invention one to three times, and pooling the isolated sera of 5 mice in the same group 7 to 14 days later.

As a result, as shown in FIGS. 7A and 7B, it could be confirmed that when the vaccine candidate was inoculated once, the IgG2c ratio was about 1.6 to 2.5-fold in the group in which MPL was mixed (Groups 4 to 6), showing a high Th1-cell-mediated immune response, and when the vaccine candidate was repeatedly inoculated two and three times, the IgG2c/IgG1 ratio was close to 1 similar to that of other vaccine candidates, and thus T cell response switching occurred. In addition, the ability to induce immunity by each adjuvant was confirmed by confirming that the other vaccine candidates with which MPL was not mixed (Group 2, Group 3) showed conversely a high Th2-cell-mediated immune response with an IgG2c/IgG1 ratio of 0.2 to 0.4 at one inoculation, and then when the vaccine mixture was inoculated repeatedly 2 to 3 times, the ratio of IgG2c/IgG1 was close to 1 similar to those of other vaccine mixture-inoculated groups.

Comparative Example 2: Comparison of Neutralizing Antibody Induction Ability According to Vaccination Neutralizing antibodies produced during vaccine administration were measured using a plaque reduction neutralization test (PRNT) (see Table 2). 7 days after inoculation (Day-49) by intramuscular injection of PBS or vaccine candidates into mice 1 to 3 times (Day-0, 14, and 42), blood was collected from the mice, and serum was separated. The serum of 5 mice of the same group was pooled and used, and after being non-assimilated at 56° C. for 30 minutes, the control serum and the experimental group serum were diluted at the same dilution rate, respectively. About 50 plaques/well were prepared from the virus control by diluting two Zika viruses (MR766 and PRVABC59 strains) whose titers (PFU/ml) were confirmed, and then mixed with the diluted serum 1:1 and the resulting mixture was reacted at 37° C. for 30 minutes. After virus reaction for 30 minutes, the serum and virus reaction solution were inoculated into Vero cells or Vero 76 cells, and then after adsorption for 2 hours, overlay media (1% sea plaque agar or 1.4% methyl cellulose) was added and incubated in a 37° C. and 5% $CO_2$ incubator for 5 or 14 days, and then stained with 1% crystal violet to confirm the number of formed plaques. $PRNT_{50}$ was calculated through % inhibition.

As a result, neutralizing antibody induction levels against the MR766 Zika virus strain were evaluated as 200 and 100 in Group 2 and Group 4, respectively, which are Zika:Envl-inoculated groups, and as 400, 1600, and 3200 in Zika:Env-inoculated groups, Group 3, Group 5, and Group 6, respectively. Similarly, neutralizing antibody induction levels against the PRVABC59 Zika virus strain were evaluated as 100 and less than 100 in Group 2 and Group 4, respectively, which are Zika:Envl-inoculated groups, and as 400, 800, and 3200 in Zika:Env-inoculated groups, Group 3, Group 5, and Group 6, respectively, confirming that more neutralizing antibodies were induced. In particular, it was confirmed that the neutralizing antibody induction level against the MR766 strain and PRVABC59 strain was 3200 in Group 6, which was a mixed inoculation of Zika:Env 10 μg and Alum 500 μg+MPL 20 μg, which was significantly higher than that of other groups.

Comparative Example 3: Cellular Immunity Evaluation 3.1. Comparison of IFN-γ and IL-12 Producing Immune Cell Assay (ELISPOT)

In order to evaluate the immune ability according to the cell-mediated immune response assay, lymphocytes expressing IFN-γ or IL-12 were measured by ELISPOT assay. IFN-γ and IL-12 ELISPOT were performed using a BD™ ELISPOT mouse IFN-γ ELISPOT set (BD Life Sciences) and mouse IL-12 (p70) ELISpotBASIC (MABTECH), respectively, according to the manufacturer's instructions.

Figure 8:
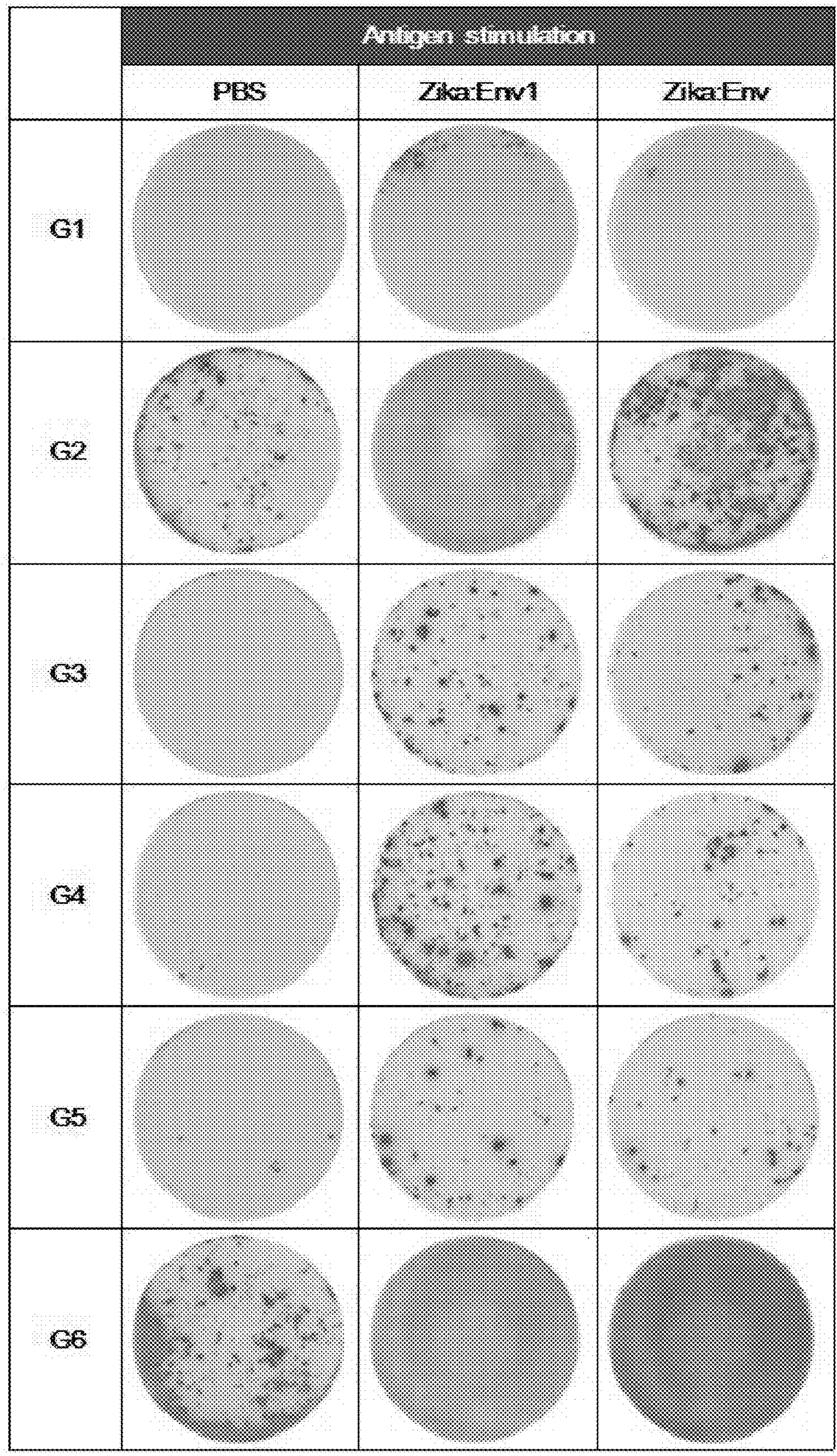
FIG. 8 is a view illustrating the results of measuring IFN-γ producing cells through ELISPOT analysis by inoculating each vaccine candidate once and pooling spleen immune cells derived from the same group 7 days later to stimulate the spleen immune cells with each Zika virus envelope protein antigen for 48 hours.

First, contrary to the expectation that the highest number of IFN-γ-secreting cells will be observed in Groups 4, 5, and 6, which are groups in which MPL was mixed, when the vaccine candidate is inoculated once, Group 2 (Zika:Envl 50 μg+Alum 50 μg) and Group 6 (Zika:Env 10 μg+Alum 500 μg+MPL 20 μg) showed the highest values (see FIG. 8).

Figure 10:
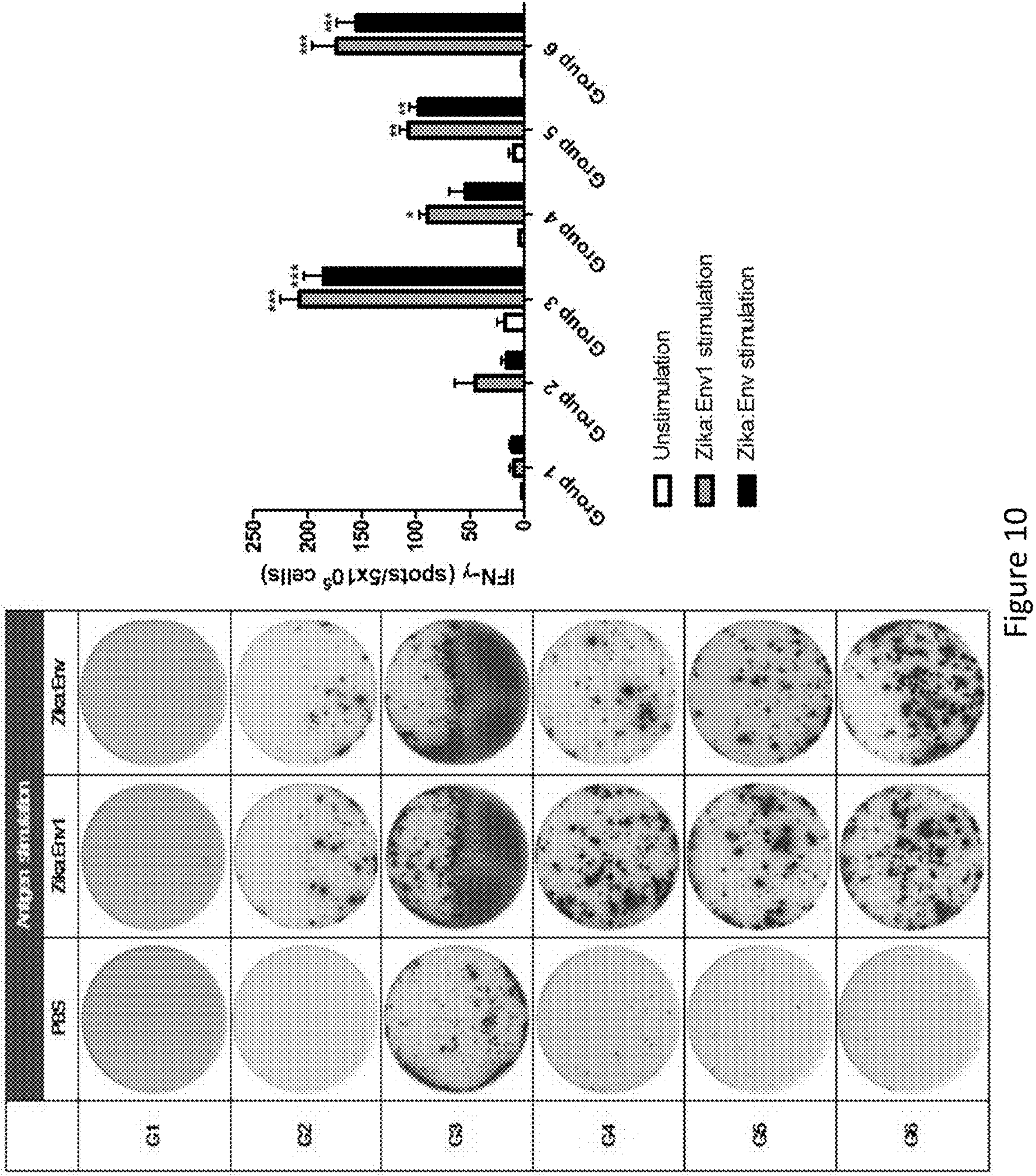
FIG. 10 is a view illustrating the results of measuring IFN-γ producing cells through ELISPOT analysis by inoculating each vaccine candidate twice and pooling spleen immune cells derived from the same group 3 days later to stimulate the spleen immune cells with each Zika virus envelope protein antigen for 48 hours (one-way ANOVA; *, $p<0.05$; , $p<0.01$; *, $p<0.001$).
Figure 12:
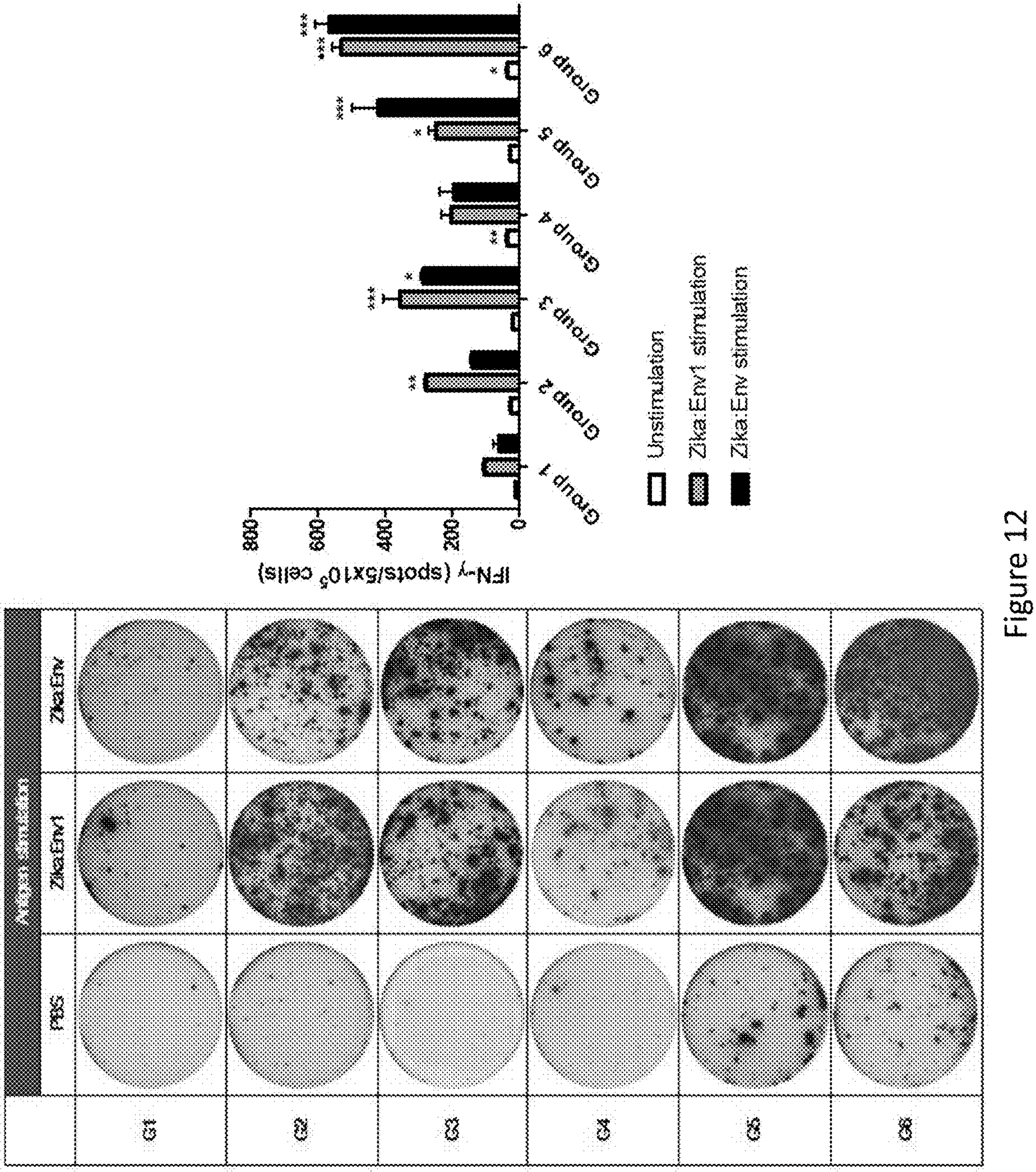
FIG. 12 is a view illustrating the results of measuring IFN-γ producing cells through ELISPOT analysis by inoculating each vaccine candidate three times and pooling spleen immune cells derived from the same group 3 days later to stimulate the spleen immune cells with each Zika virus envelope protein antigen for 48 hours (one-way ANOVA; *, $p<0.05$; , $p<0.01$; *, $p<0.001$).
Figure 13:
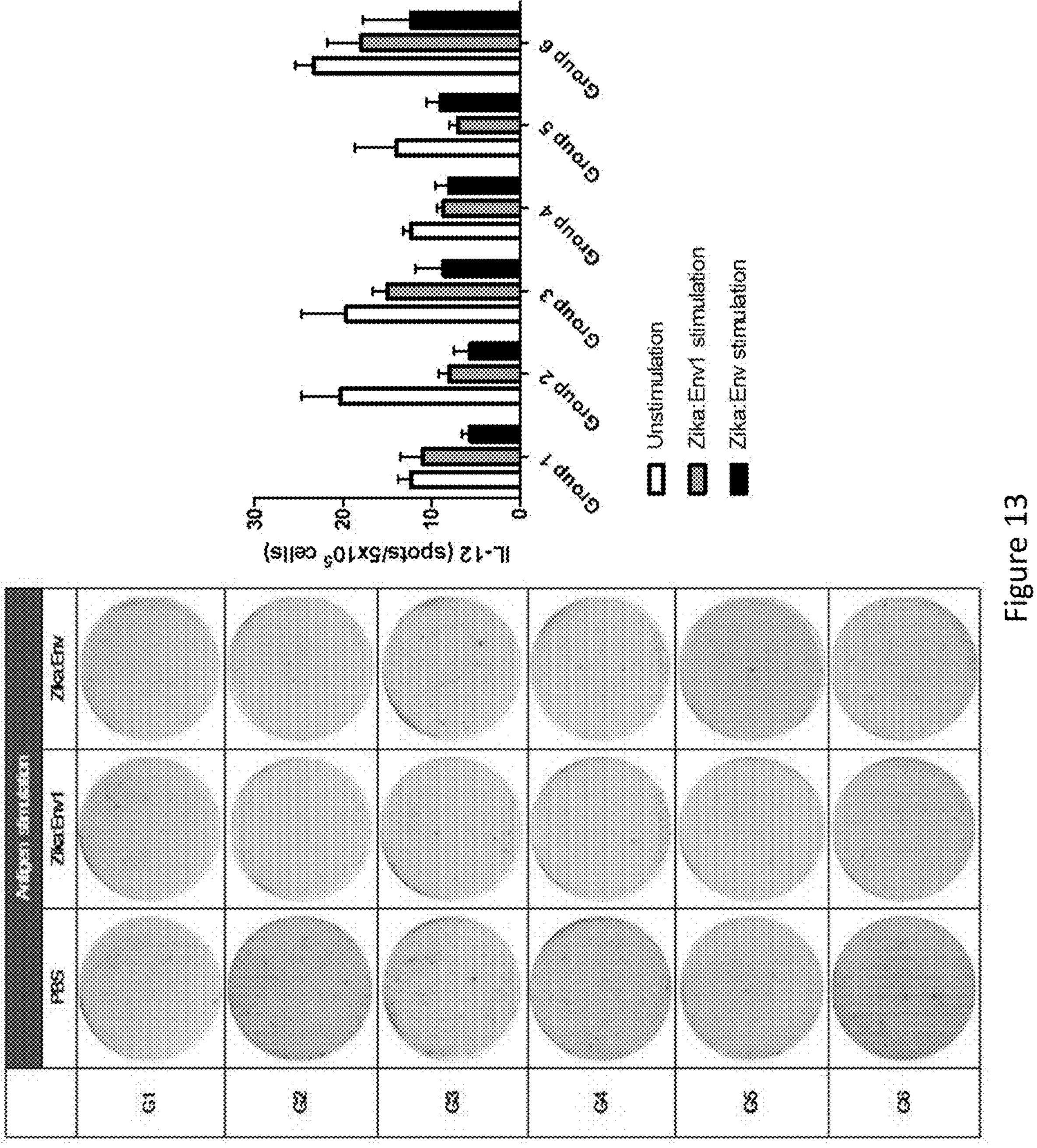
FIG. 13 is a view illustrating the results of measuring IL-12 producing cells through ELISPOT analysis by inoculating each vaccine candidate three times and pooling spleen immune cells derived from the same group 3 days later to stimulate the spleen immune cells with each Zika virus envelope protein antigen for 48 hours (one-way ANOVA; *, $p<0.05$; , $p<0.01$; *, $p<0.001$).

When the vaccine candidate was inoculated twice, the number of IFN-γ-secreting cells was observed to be around 45 and 90, respectively, in Group 2 and Group 4 which are Zika:Envl-inoculated groups, whereas in Groups 3, 5 and 6, which are Zika:Env-inoculated groups, 200, 100 and 170 IFN-γ secreting cells were observed, respectively (see FIG. 10). Similarly, even when the vaccine candidate was inoculated three times, IFN-γ-secreting cells were observed to be around 280 and 200 in Group 2 and Group 4 which are Zika:Envl-inoculated groups, respectively, whereas in Groups 3, 5, and 6 which are Zika:Env-inoculated groups, more IFN-γ-secreting cells were observed to be around 350, 420, and 560, respectively, and in particular, Groups 5 and 6 were observed to continuously express a high number of IFN-γ-secreting cells (see FIG. 12).

Figure 9:
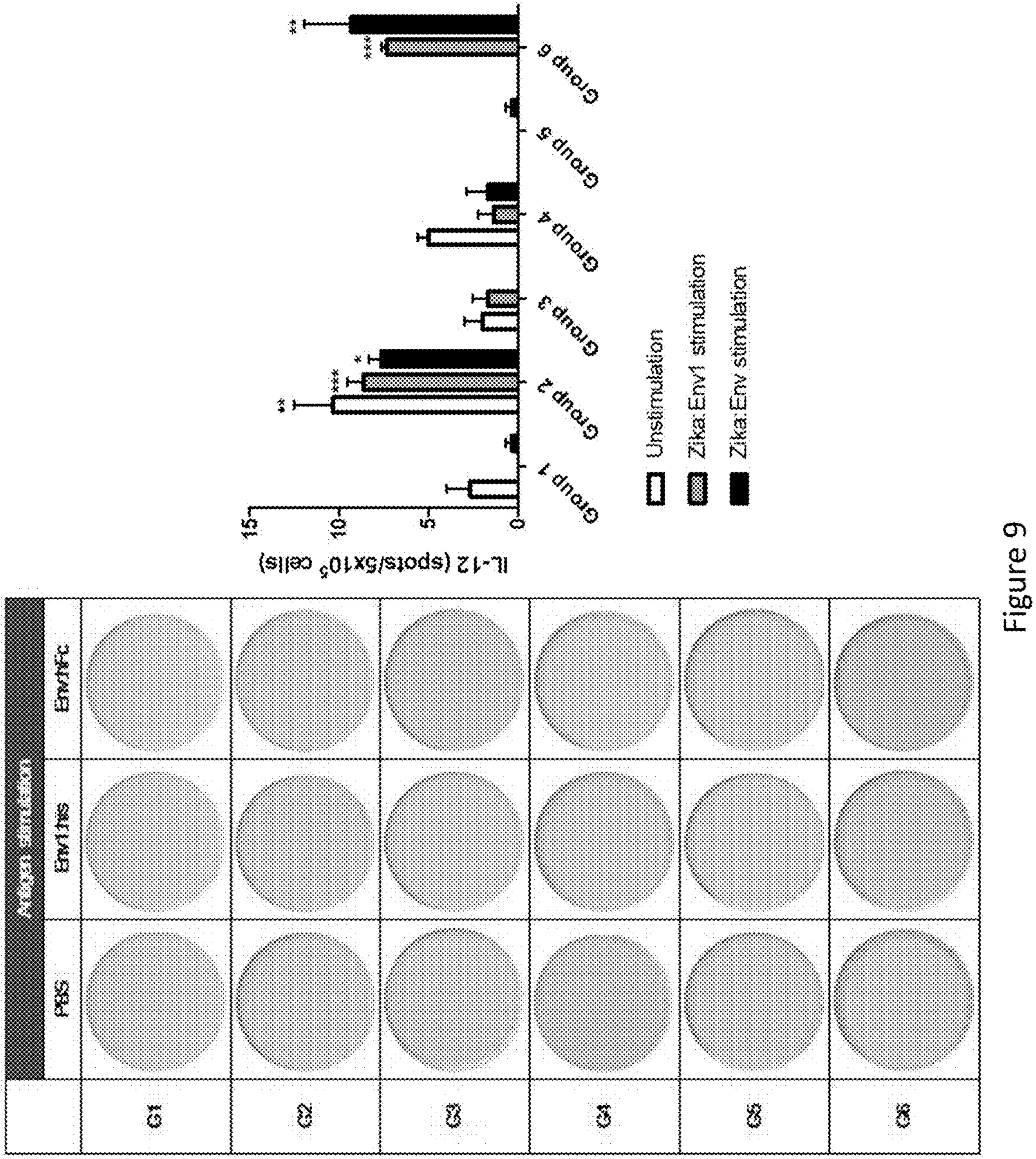
FIG. 9 is a view illustrating the results of measuring IL-12 producing cells through ELISPOT analysis by inoculating each vaccine candidate once and pooling spleen immune cells derived from the same group 7 days later to stimulate the spleen immune cells with each Zika virus envelope protein antigen for 48 hours (one-way ANOVA; *, $p<0.05$; , $p<0.01$; *, $p<0.001$).
Figure 11:
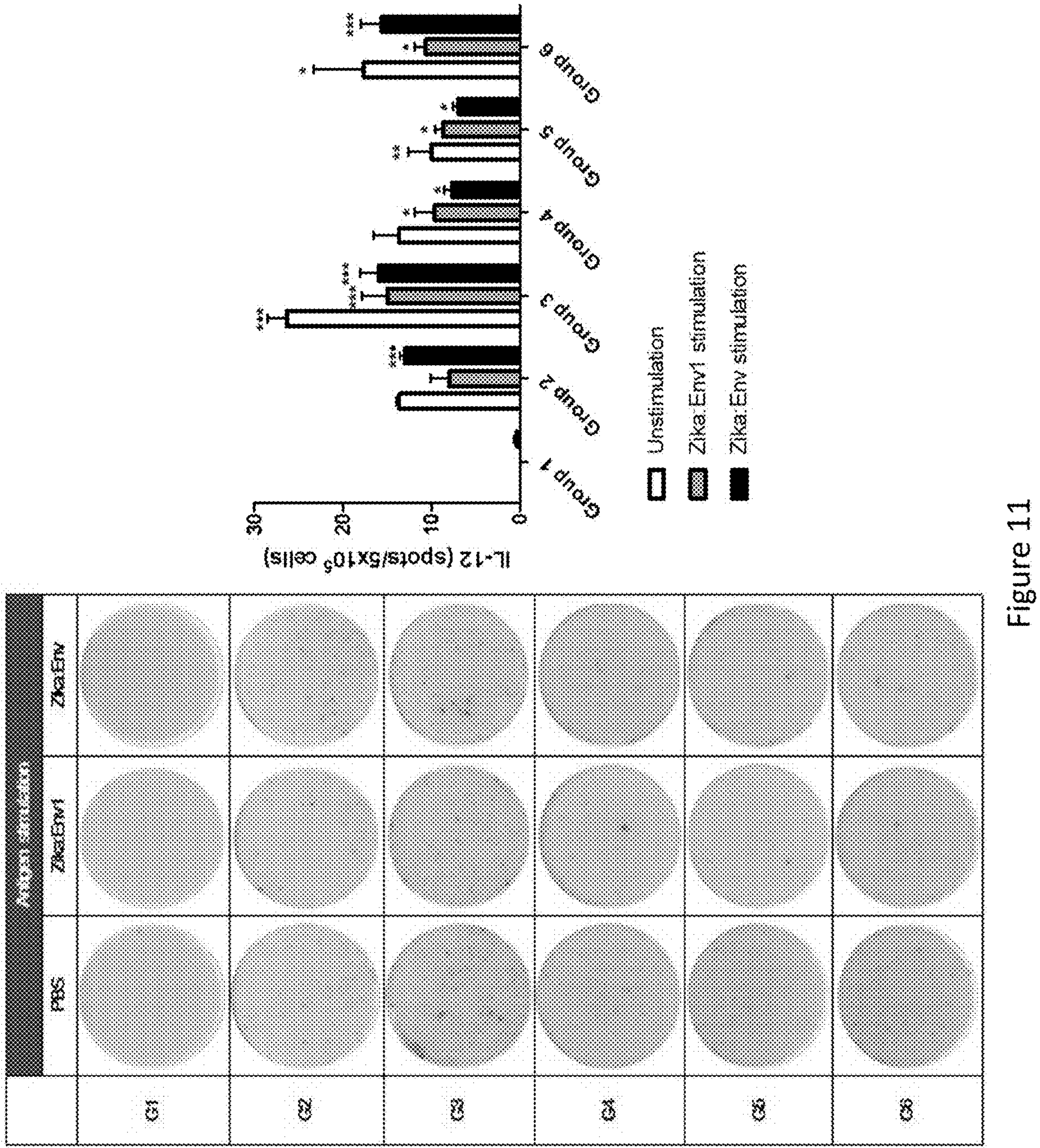
FIG. 11 is a view illustrating the results of measuring IL-12 producing cells through ELISPOT analysis by inoculating each vaccine candidate twice and pooling spleen immune cells derived from the same group 3 days later to stimulate the spleen immune cells with each Zika virus envelope protein antigen for 48 hours (one-way ANOVA; *, $p<0.05$; , $p<0.01$; *, $p<0.001$).

For the IL-12-secreting cells, similar to the IFN-γ secreting cell test results, the highest number of IL-12-secreting cells were observed in Group 2 and Group 6 when the vaccine candidate was inoculated once (see FIG. 9), and in Group 3 and Group 6 when the vaccine candidate was inoculated twice (see FIG. 11). However, when the vaccine candidate was inoculated three times, all experimental groups (Groups 2 to 6) did not show a significant difference compared to Group 1, which is the control.

3.2. Comparison of Cytokine Production Amounts

To analyze the effect of vaccine candidate (Zika:Envl, Zika:Env) inoculation on cytokine IFN-γ, IL-12, IL-4 and TNF-α secretion amounts, and to perform a more detailed analysis of the ELISPOT test results, the secretion amounts were evaluated using an ELISA kit for each cytokine.

Figure 14:
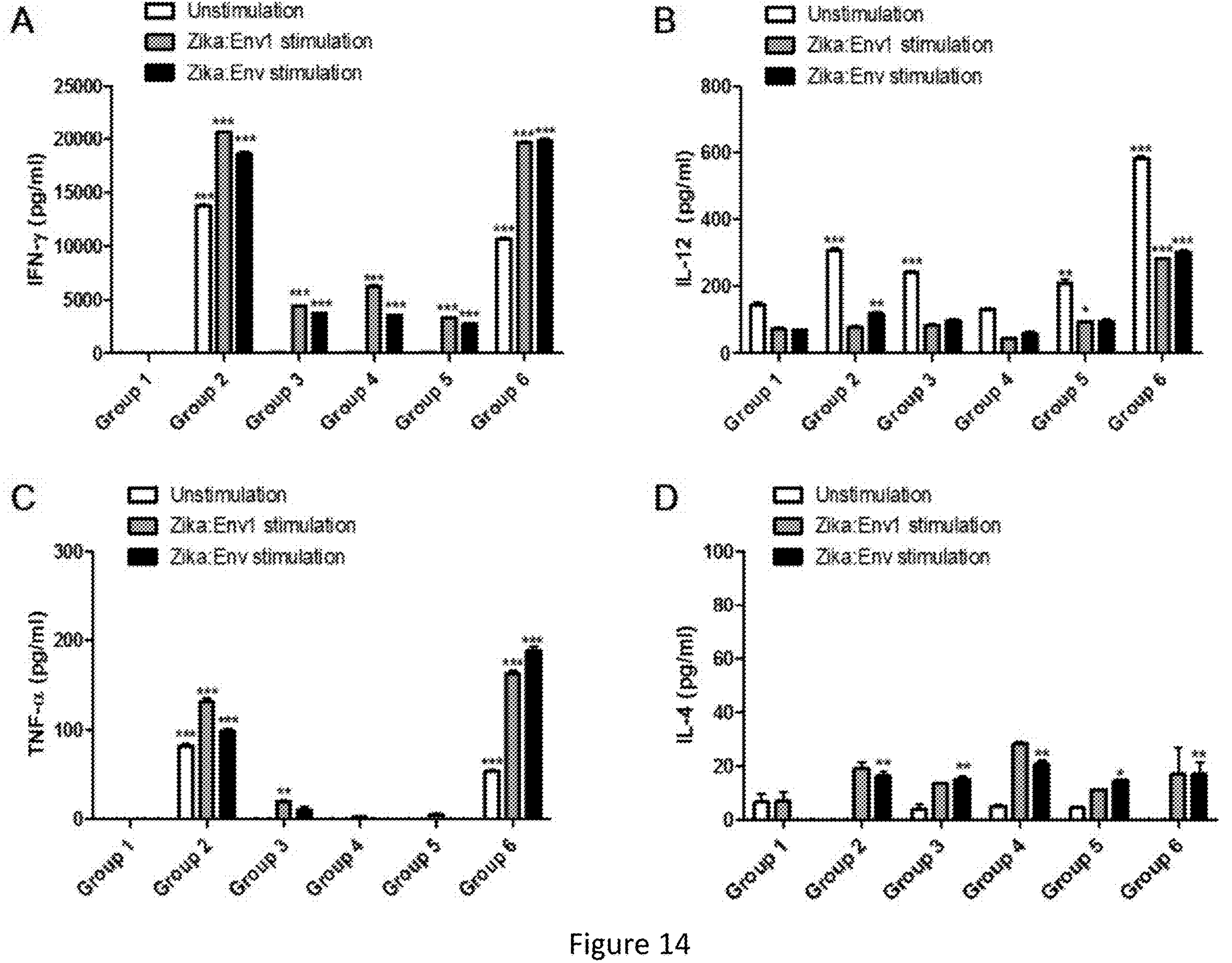
FIG. 14 is a view illustrating the results of measuring the production amounts of IFN-γ (A), IL-12 (B), TNF-α (C), and IL-4 (D) through ELISA analysis by inoculating each vaccine candidate once and pooling spleen immune cells derived from the same group 7 days later to stimulate the spleen immune cells with each Zika virus envelope protein antigen for 48 hours (one-way ANOVA; *, $p<0.05$; , $p<0.01$; *, $p<0.001$).

First, as shown in FIG. 14, the secretion amounts of IFN-γ and TNF-α when the vaccine candidate was inoculated once were shown to be high in Group 2 (Zika:Envl 50 μg+Alum 50 μg) and Group 6 (Zika:Env 10 μg+Alum 500 μg+MPL 20 μg) similar to the ELISPOT test results. There was no significant difference between the groups for IL-4, but when Group 6 was not sensitized, the highest IL-12 secretion was observed, confirming that overall immunogenicity was increased.

Figure 15:
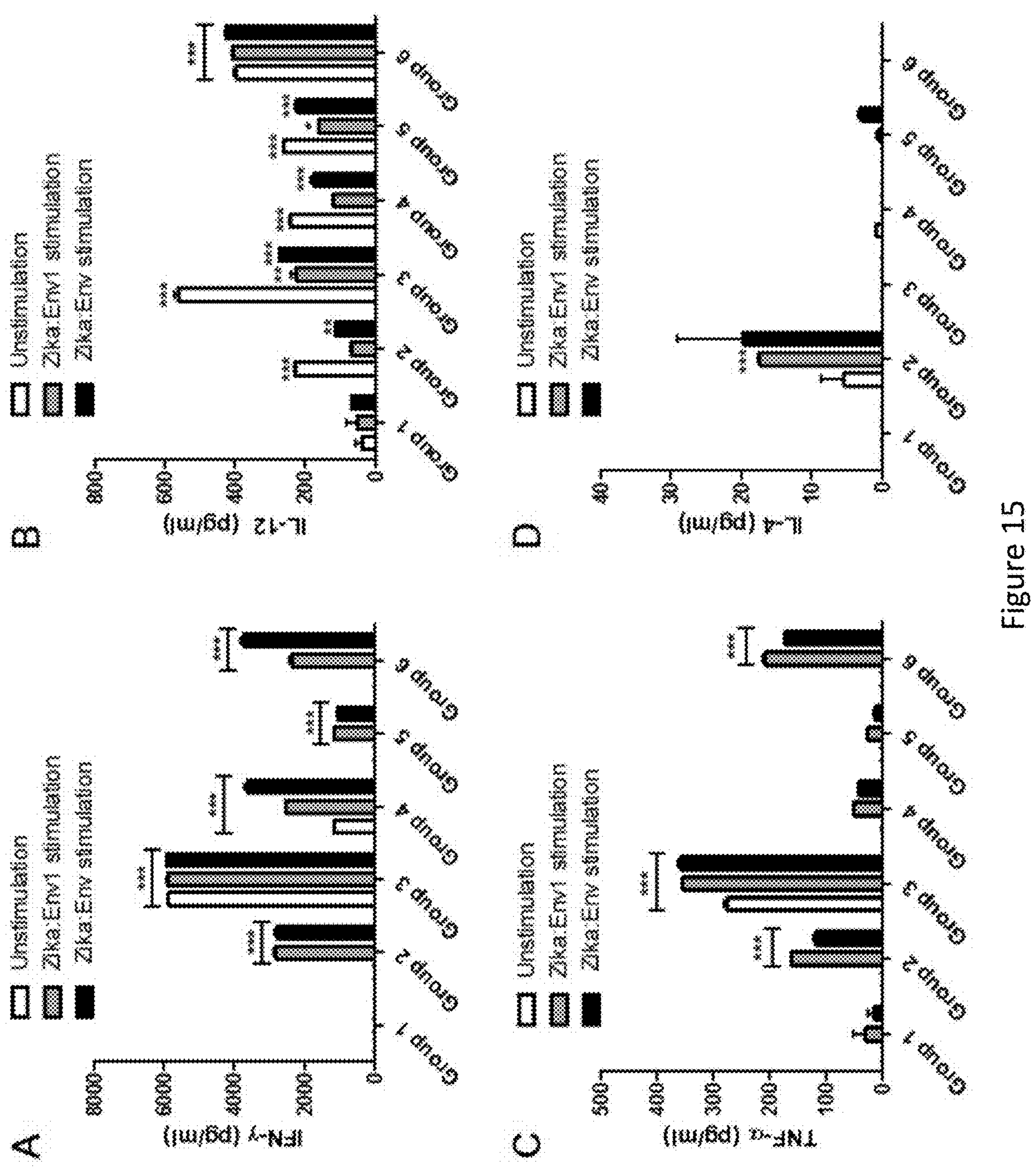
FIG. 15 is a view illustrating the results of measuring the production amounts of IFN-γ (A), IL-12 (B), TNF-α (C), and IL-4 (D) through ELISA analysis by inoculating each vaccine candidate twice and pooling spleen immune cells derived from the same group 3 days later to stimulate the spleen immune cells with each Zika virus envelope protein antigen for 48 hours (one-way ANOVA; *, $p<0.05$; , $p<0.01$; *, $p<0.001$).
Figure 16:
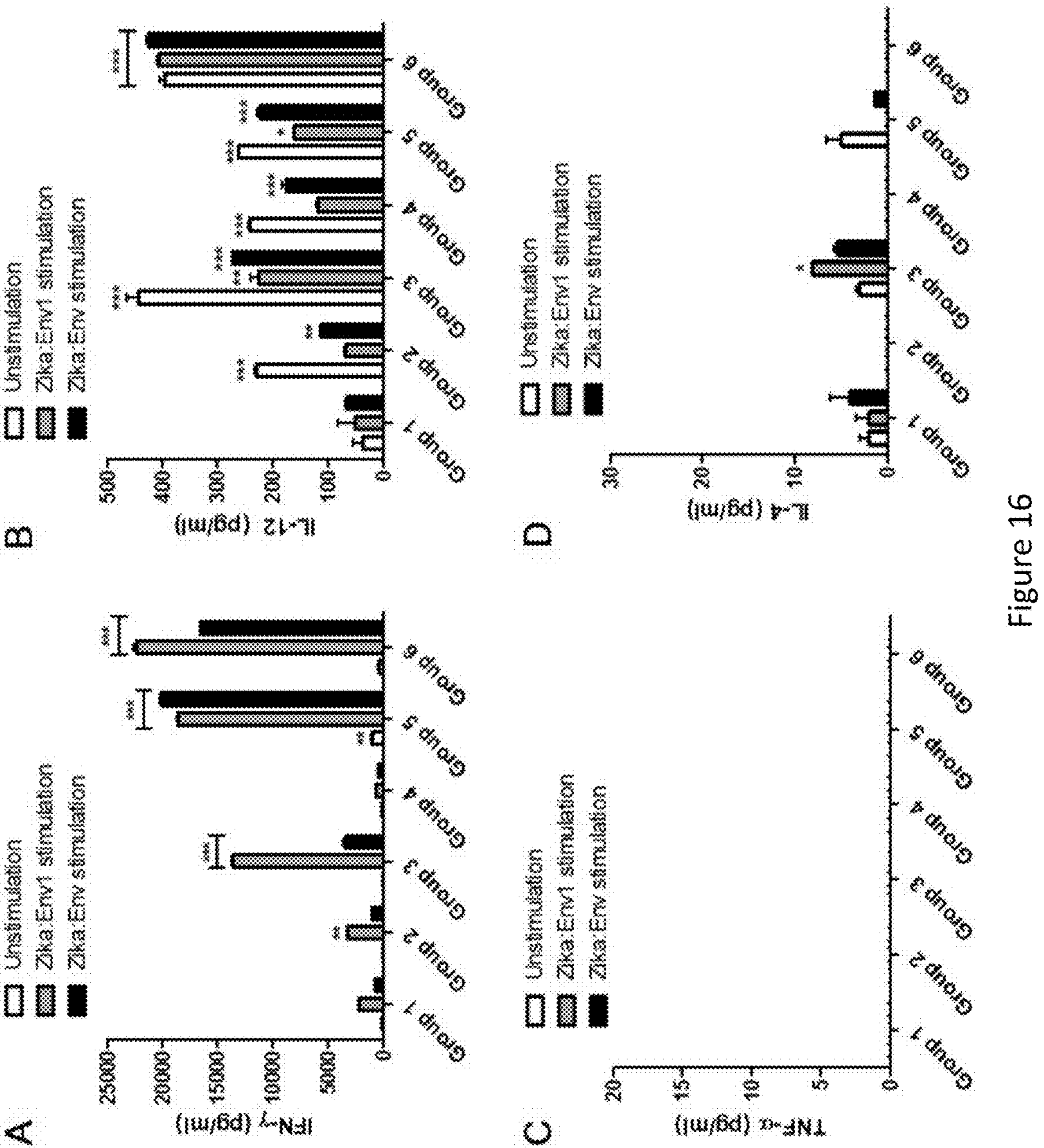
FIG. 16 is a view illustrating the results of measuring the production amounts of IFN-γ (A), IL-12 (B), TNF-α (C), and IL-4 (D) through ELISA analysis by inoculating each vaccine candidate three times and pooling spleen immune cells derived from the same group 3 days later to stimulate the spleen immune cells with each Zika virus envelope protein antigen for 48 hours (one-way ANOVA; *, $p<0.05$; , $p<0.01$; *, $p<0.001$).
Figures 18, 18B:
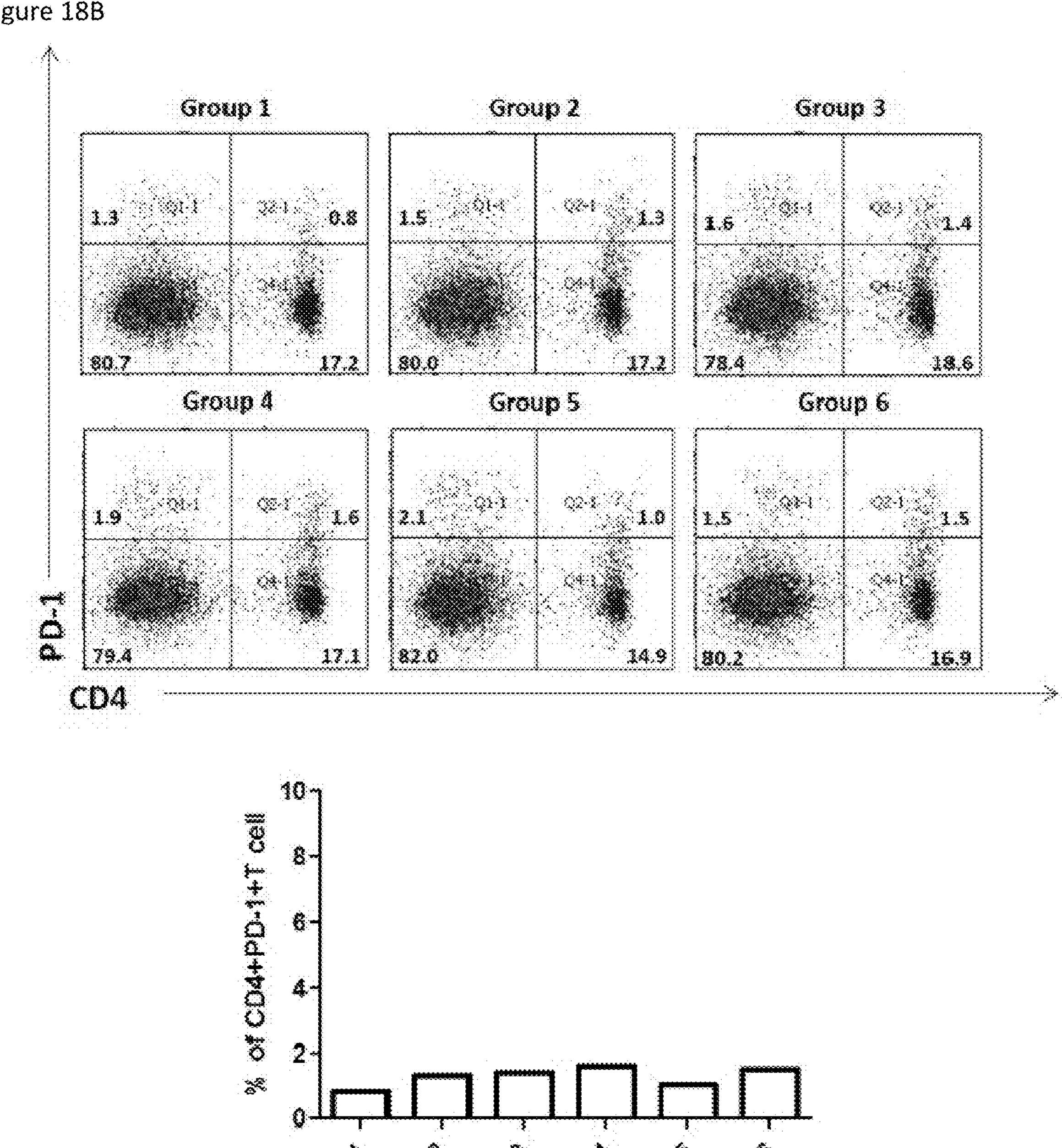

In addition, as can be seen in FIG. 15, when the vaccine candidate was inoculated twice, the secretion amount of IFN-γ was the highest in Group 3, similar to the previous test results. Similarly, even when the vaccine candidate was inoculated three times, it could be confirmed that the secretion amount of IFN-γ was shown to be the highest in Group 3, 5, and 6-inoculated groups, which are Zika:Env-inoculated groups. TNF-α secretion amounts were decreased in the three time-inoculated groups, but in Group 5 (Zika:Env 50 μg+Alum 50 μg+MPL 20 μg), and Group 6 (Zika:Env 10 μg+Alum 500 μg+MPL 20 μg), it was found that the secretion amount of IFN-γ increased about 4-fold to 19-fold compared to the twice-inoculated group (see FIG. 16).

3.3. Immune Cell Response Analysis

In order to analyze immune cells activated during vaccination, $CD4^+$, $CD8^+$ T cells ($CD3^+$, $CD4^+$, $CD8^+$) were measured in splenocytes isolated from mice inoculated with each vaccine candidate using flow cytometry.

When the vaccine candidate was vaccinated 1 and 3 times, the ratio of effector T cells did not show a significant difference between each group compared to the negative control (PBS; Group 1), and the T cell population according to repeated vaccination showed no change (see FIG. 17). These results suggest that when the results of the previous cellular immunity test are also considered, there is no change in the T cell population when the vaccine candidate is inoculated, but the activity of T cells is increased.

In addition, as shown in FIGS. 18A to 18D, it could be confirmed that when the degree of exhaustion of $CD4^+$ T cells and $CD8^+$ T cells was observed using the PD-1 marker, the proportion of PD-$1^+$ T cells in all groups when the vaccine candidate was inoculated once was found to be less than 1%, and exhausted T cells did not increase even during three repeated inoculations. Therefore, it could be seen that the depletion of effector T cells did not occur during repeated inoculation of all vaccine candidates.

Figure 19B:
FIGS. 19A and 19B are views illustrating the results of measuring the proportions of regulatory T cells ($CD4^+$, $CD25^+$, $Foxp3^+$) through flow cytometry by inoculating each vaccine candidate once or three times and pooling spleen immune cells derived from the same group 7 days later (day-7) or 3 days later (day-45), respectively.
Figure 19:
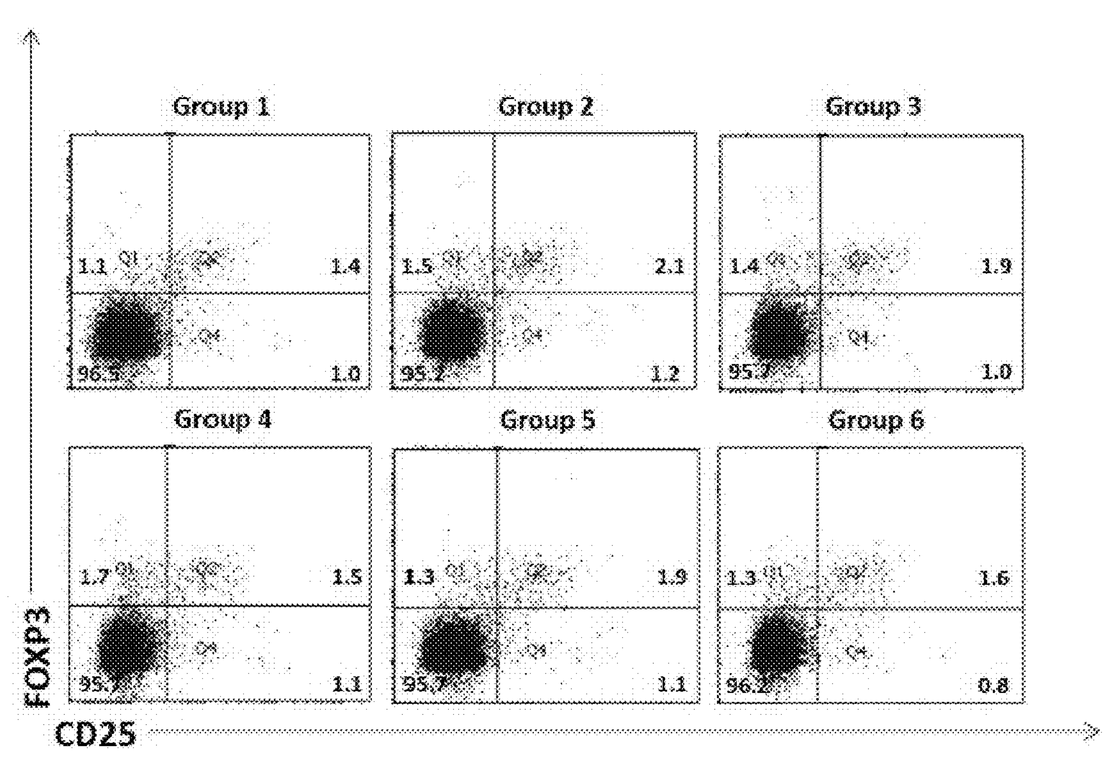
Figure 19:
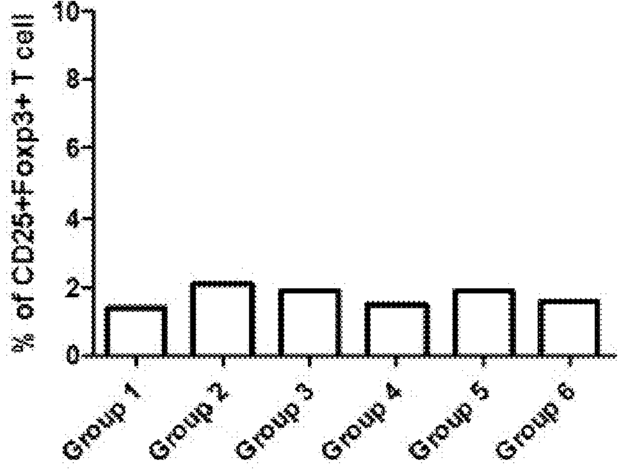

Finally, as a result of observing regulatory T cells ($T_{reg}$ cells), as shown in FIGS. 19A and 19B, it was confirmed that when the vaccine candidate was inoculated three times, the proportion of regulatory T cells was slightly increased in all groups compared to when the vaccine candidate was inoculated once, but all showed a low increase rate of 1-2%, and thus the proportion of regulatory T cells did not increase even during repeated inoculation of the vaccine candidate. These results suggest that the activation of effector T cells is not suppressed.

Comparative Example 4: Protective Efficacy Evaluation 4.1. Maternal Antibody Evaluation Maternal antibodies in serum isolated from blood collected from offspring mice two days after birth, which were born to mothers inoculated with the vaccine candidates, were measured using the indirect ELISA method developed in-house.

Figure 20A:
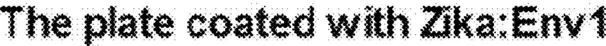
FIGS. 20A and 20B are views illustrating the results of indirect ELISA analysis by pooling the sera of offspring mice, obtained by inoculating vaccine candidates (Zika: Envl, Zika:Env) three times and mating 7 days later, in the same group (one-way ANOVA; *, p<0.05; , p<0.01; *, p<0.001).
Figure 20:
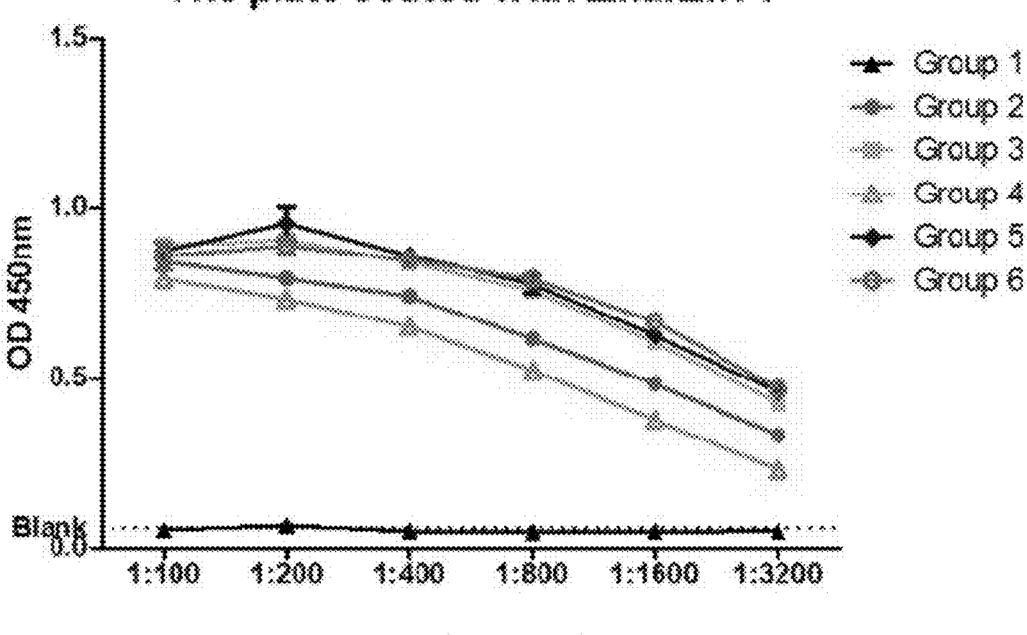
Figure 20:
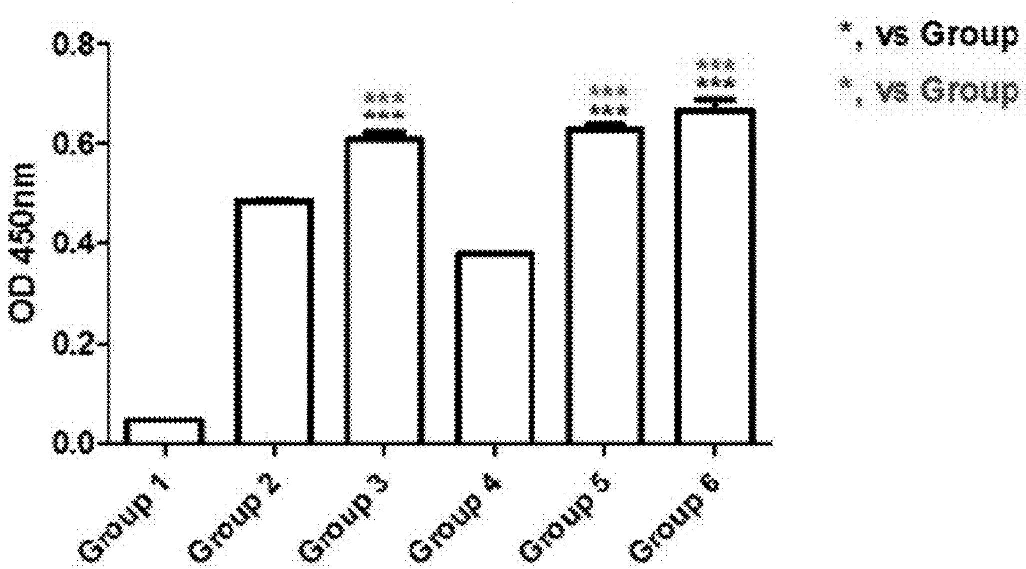

As a result, as shown in FIGS. 20A and 20B, for a maternal antibody, it could be seen that the serum of offspring mice born to mothers inoculated with the vaccine candidates showed a higher level of antibody titer compared to the negative control (PBS; Group 1). Among them, in particular, in the Zika:Env-inoculated groups (Groups 3, 5, and 6), it was confirmed that the maternal antibody significantly increased compared to the Zika:Envl-inoculated groups (Groups 2 and 4).

4.2. Comparative Analysis of Cytokine-Producing Immune Cells in Offspring Mice

Lymphocytes expressing IFN-γ or IL-12 in spleen immune cells isolated by removing the spleens of offspring mice thirty days after birth, which were born to mothers inoculated with the vaccine candidates, were measured by ELISPOT analysis. IFN-γ and IL-12 ELISPOT were performed using a BD™ ELISPOT mouse IFN-γ ELISPOT set (BD Life Sciences, USA) and mouse IL-12 (p70) ELISpot-BASIC (MABTECH, USA), respectively, according to the manufacturer's instructions.

Figure 21:
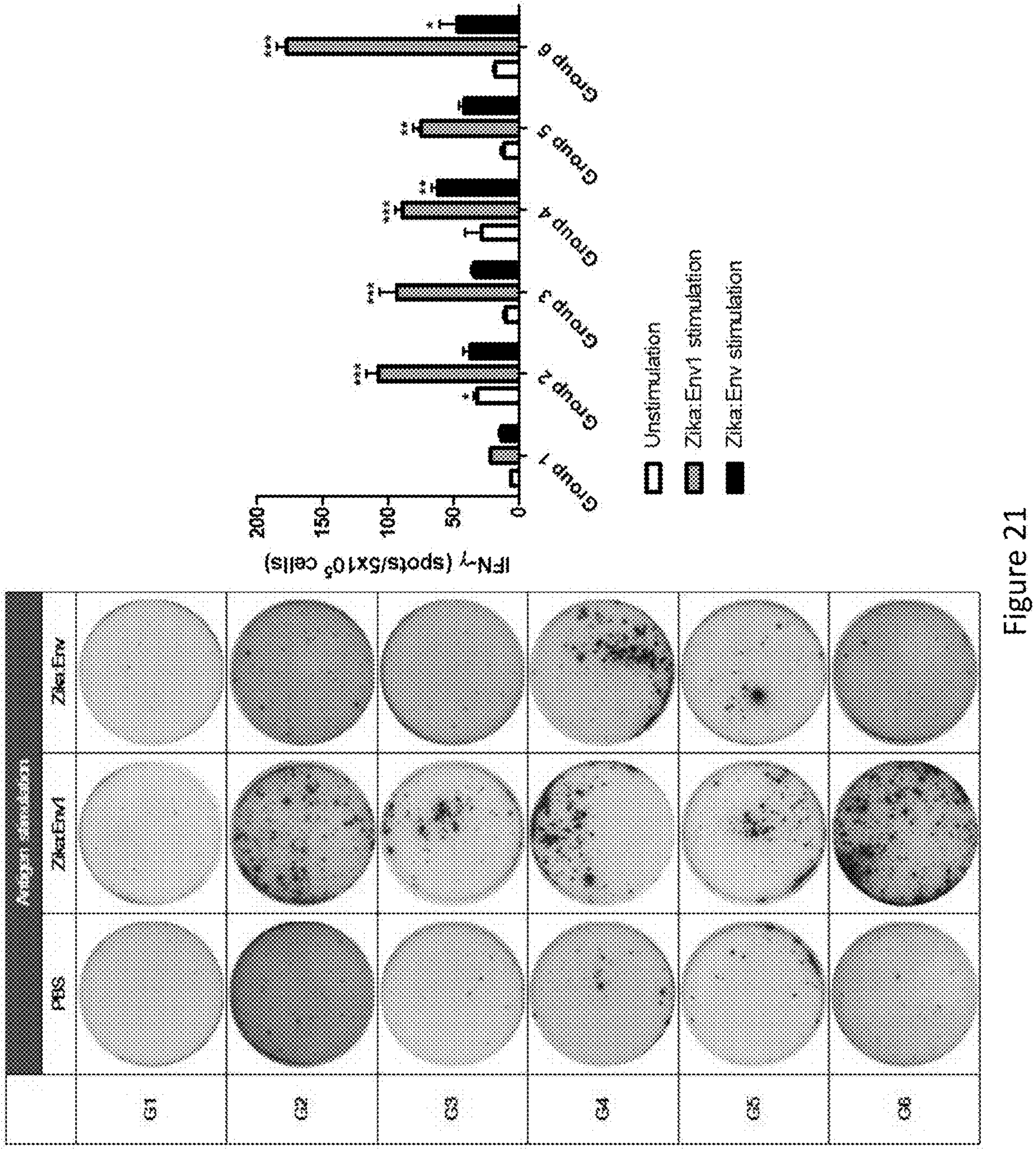
FIG. 21 is a set of views illustrating the results of measuring IFN-γ producing cells through ELISPOT analysis and quantifying the number of spots by removing the spleens from offspring mice obtained by inoculating vaccine candidates (Zika:Envl, Zika:Env) three times and mating 7 days later, and stimulating spleen immune cells with each antigen for 48 hours (one-way ANOVA; *, p<0.05; , p<0.01; *, p<0.001).

As a result, as shown in FIG. 21, it was confirmed that IFN-γ-producing immune cells were generally increased in the offspring mice born in the vaccine candidate-inoculated groups compared to the offspring mice born in the negative control group (PBS; Group 1). Among them, in the case of Group 6, it was confirmed that the number of IFN-γ-producing immune cells increased more than 8-fold compared to the PBS-inoculated group during antigen restimulation.

Figure 22:
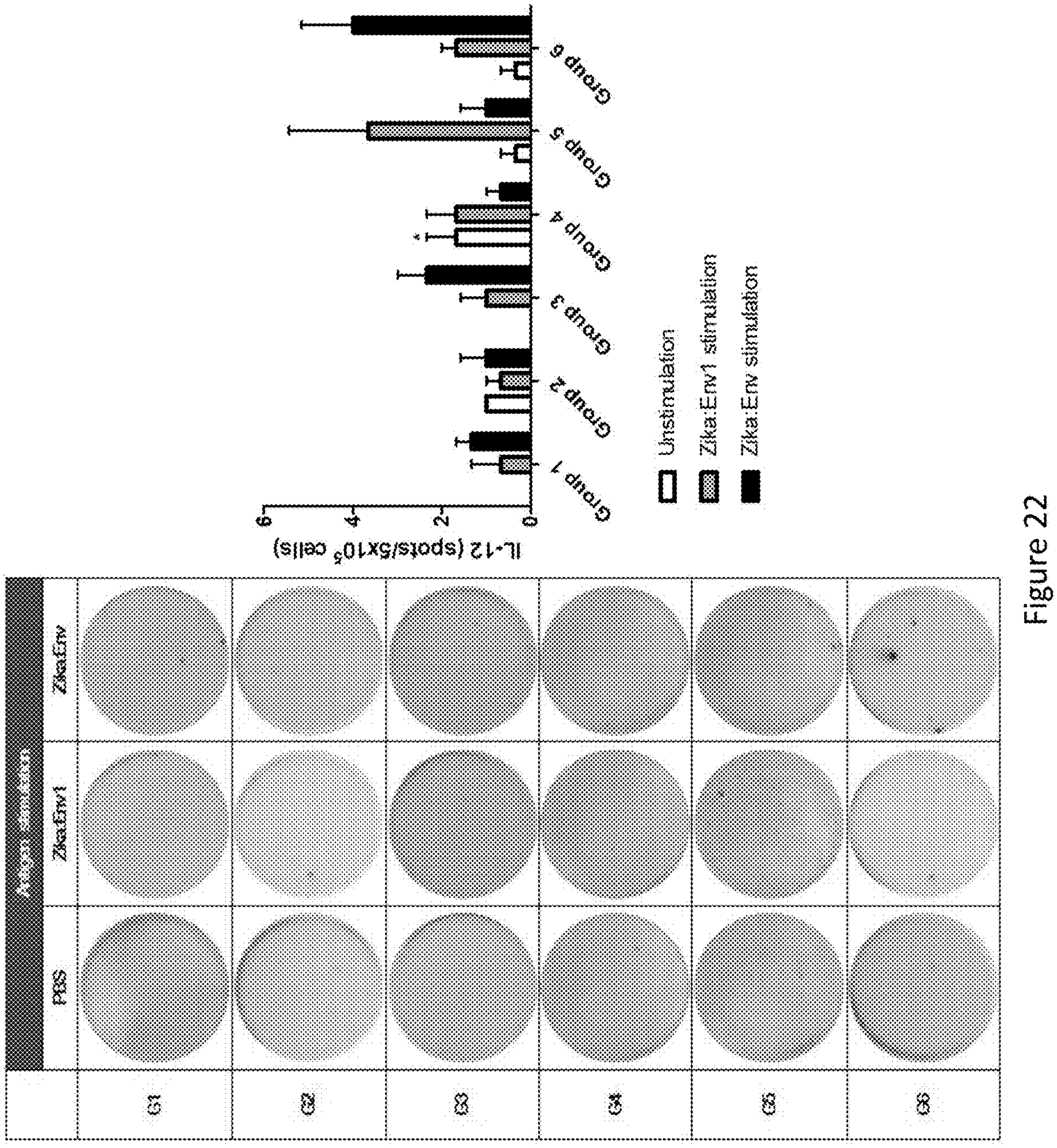
FIG. 22 is a set of views illustrating the results of measuring IL-12 producing cells through ELISPOT analysis and quantifying the number of spots by removing the spleens from offspring mice obtained by inoculating vaccine candidates (Zika:Envl, Zika:Env) three times and mating 7 days later, and stimulating spleen immune cells with each antigen for 48 hours (one-way ANOVA; *, p<0.05; , p<0.01; *, p<0.001).

Meanwhile, in the case of IL-12-producing immune cells, as shown in FIG. 22, the number of IL-12-producing immune cells showed a tendency to increase in Groups 3 to 6 compared to offspring mice born in the negative control group (PBS; Group 1), but there was no significant difference.

4.3. Comparison of Production Amounts of Cytokines in Offspring Mice

To analyze the effect of vaccine candidate inoculation on IFN-γ, IL-12, and TNF-α secretion amounts, and to perform a more detailed analysis of the ELISPOT test results, the production amounts were compared and evaluated using an ELISA kit for each cytokine.

Figure 23:
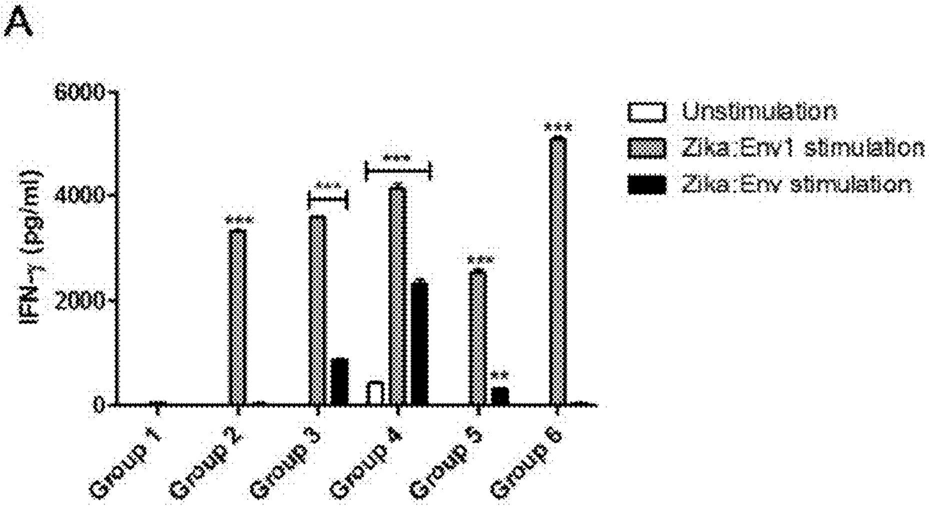
FIG. 23 is a set of views illustrating the results of measuring the production amounts of IFN-γ (A), IL-12 (B) and TNF-α (C) through ELISA analysis by removing the spleens from offspring mice obtained by inoculating vaccine candidates (Zika:Envl, Zika:Env) three times and mating 7 days later, and stimulating spleen immune cells with each antigen for 48 hours (one-way ANOVA; *, p<0.05; , p<0.01; *, p<0.001).
Figure 23:
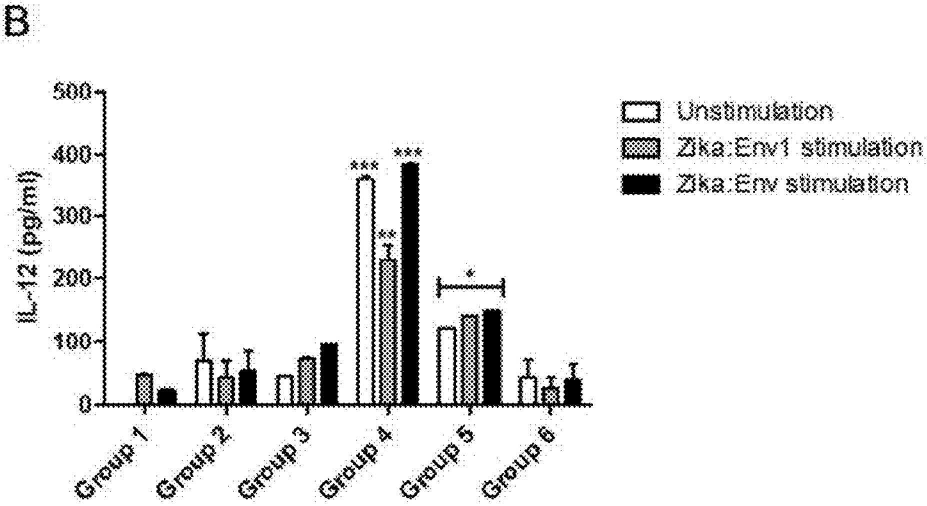
Figure 23:
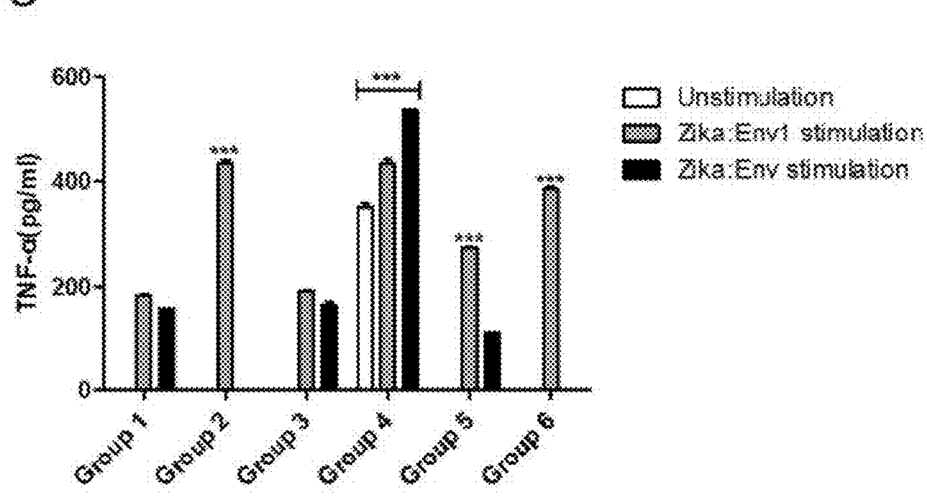

As a result, as shown in FIG. 23, it could be confirmed that IFN-γ-secretion amounts were generally increased in the offspring mice born in the vaccine candidate-inoculated groups compared to the offspring mice born in the negative control group (PBS; Group 1). In particular, in the case of Group 6, it was shown that the IFN-γ secretion amount was increased 104-fold or more compared to the PBS-inoculated group during antigen restimulation (see FIG. 23A).

For the IL-12 secretion amount, it could also be confirmed that the IL-12 production amount was significantly increased during antigen restimulation in offspring mice born in Groups 3, 4, and 5 compared to offspring mice born in the control group, and in particular, in the case of Group 4, it was found that when the group was not sensitized, the IL-12 secretion amount increased about 400-fold or more compared to the PBS-inoculated group (see FIG. 23B).

In the case of TNF-α secretion amount, it was confirmed that the amount of TNF-α secretion was significantly increased during antigen restimulation in offspring mice born in Groups 2, 4, 5, and 6 compared to offspring mice born in the control group, and in particularly, in the case of Group 4, it was confirmed that overall immunogenicity was increased by confirming that, when the group was not sensitized, the TNF-α production amount was increased about 400-fold or more, similar to IL-12, compared to the control.

4.4. Comparative Evaluation of Protective Efficacy

Figures 24, 24B:
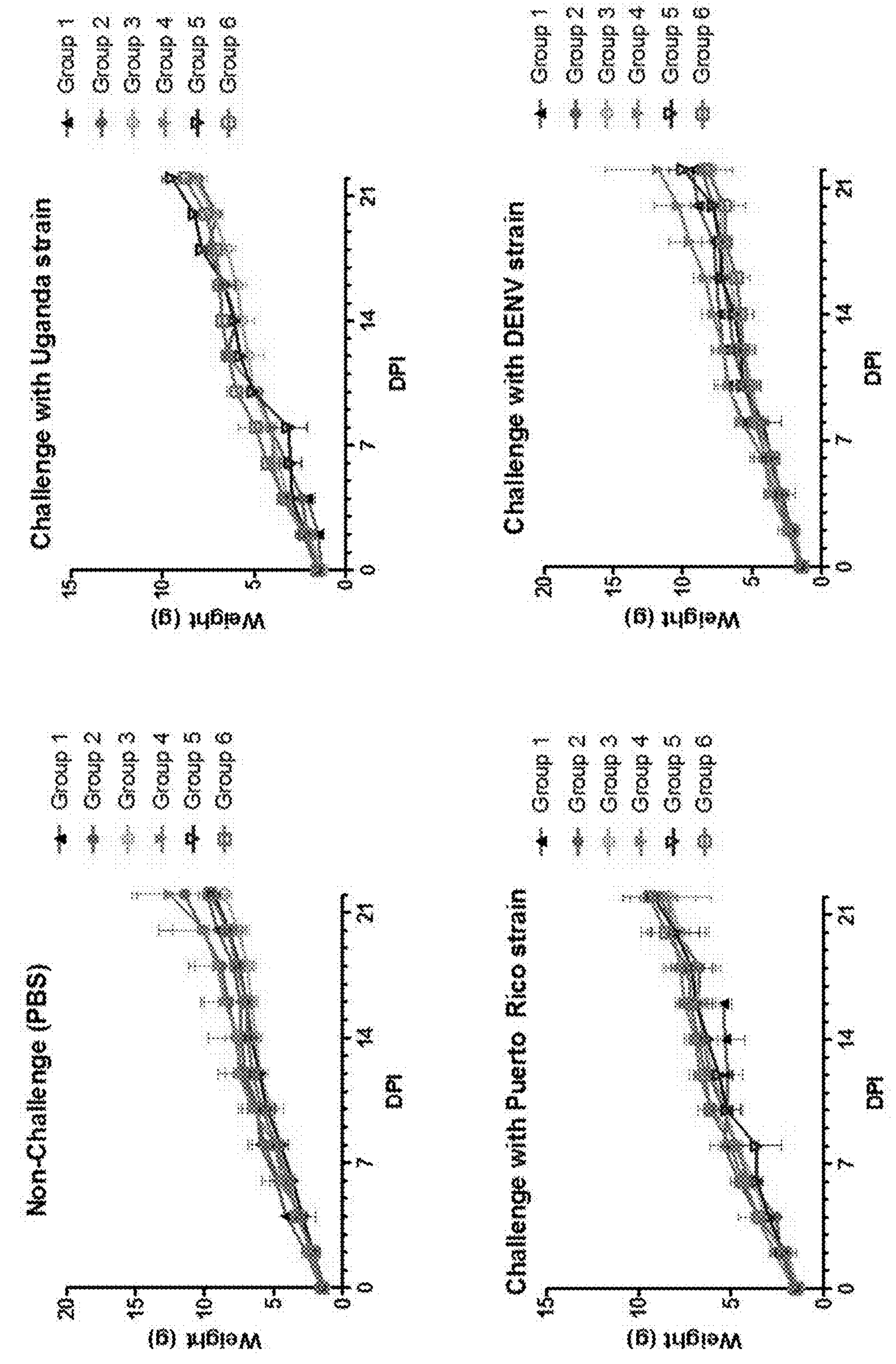

In order to evaluate the efficacy of cross-protection against two Zika viruses (PRVABC59, MR766 strains) of two-day-old offspring mice, which were born to mothers inoculated with the vaccine candidate 3 times (Day-0, 14, 42) by intramuscular injection and mated, dengue virus (DENV type 2) was inoculated subcutaneously and clinical symptoms according to each virus were observed. The amount of each inoculated virus was described in Table 2 above, and the results are shown in FIGS. 24A and 24B.

First, when the MR766 strain (Uganda strain) was subcutaneously inoculated into offspring mice at $10^{6.8}$TCID$_{50}$/mouse, all 5 offspring mice born to mothers in the negative control group (PBS; Group 1) died within 6 days (see FIG. 24A). Offspring mice born from mice in Groups 2 and 4, which are Zika:Envl-inoculated groups, died within 10 days of challenge inoculation, that is, 4 out of 5 mice in Group 2 and all 5 mice in Group 4 died. In contrast, 2 out of 5 mice born from mice in Group 3, which is a Zika:Env-inoculated group, died within 8 days, and 3 out of 5 mice born from mice in Group 5 died within 10 days. Only 1 out of 5 offspring mice born from mice in Group 6 died on day 6. The aforementioned results show that a Zika:Env-inoculated group has superior protective efficacy against the MR766 strain compared to a Zika:Envl-inoculated group.

Next, when the PRVABC59 strain (Puerto Rico strain) was challenged with $10^{6.3}$ TCID$_{50}$/mouse, 2 out of 5 offspring mice born to negative control mothers (PBS; Group 1) died on days 8 and 10, and one mouse lost body weight on day 16 of infection and 2 mice lost body weight from day 16 of infection, and died on day 18. In the case of offspring mice born from mice in Groups 2 and 4, which are Zika:Envl-inoculated groups, one mouse died on day-4 (Group 2) and day-12 (Group 4) of challenge inoculation, no body weight loss was observed in offspring mice of Group 2, but 2 mice showed clinical symptoms of lameness. In the offspring mouse group of Group 4, one mouse showed body weight loss from day-18, and two mice showed clinical symptoms of lameness. In contrast, all five offspring mice born from mice of Groups 3 and 6, which are Zika:Env-inoculated groups, survived the challenge inoculation, and did not show any clinical signs of body weight loss or lameness. However, two of the offspring mice born from mice of Group 5 showed body weight loss from day-7 and died on day-10. Summarizing the above results, it was found that a Zika:Env-inoculated group also has superior protective efficacy against the PRVABC59 strain compared to a Zika:Envl-inoculated group.

Finally, in order to confirm whether the vaccine candidate materials (Zika:Envl, Zika:Env) have a cross-protective effect against dengue virus (DENV), DENV was subcutaneously inoculated into two-day-old offspring mice born to mothers, who were inoculated 3 times (Day-0, 14, and 42) with the vaccine candidate, at $10^{6}$ TCID$_{50}$/mouse to observe the alleviation of symptoms. As a result, 3 out of 5 offspring mice born to mothers inoculated with PBS died within 12 days, whereas in the vaccine candidate-inoculated groups except for Groups 4 and 5, offspring mice born from Groups 2, 3, and 6 mice all survived, and no clinical signs of body weight loss or lameness were observed, after the challenge inoculation. In addition, 2 out of 5 offspring mice born from mice in Group 4 died on day-4 of challenge inoculation, and one out of 5 offspring mice born from mice of Group 5 lost body weight from day-6 and died on day-10. Based on these results, it was possible to confirm the cross-protective effect against dengue virus when the vaccine candidates were inoculated.

4.5. Measurement of Amount of Virus in Blood after Challenge Inoculation

Tissue culture infective dose 50 (TCID$_{50}$) in serum obtained 2 days after challenging inoculation with two Zika viruses (MR766, PRVABC59 strain) or dengue virus (DENV type 2) to two-day-old offspring mice born to mothers inoculated with vaccine candidates was measured to measure the content of viruses in serum. The serum of 5 mice of the same group was pooled and used, and after being non-assimilated at 56° C. for 30 minutes, the control serum and the experimental group serum were diluted decimally from $10^{1}$ to $10^{3}$, respectively. The diluted serum was inoculated into Vero cells or Vero 76 cells, and the presence or absence of CPE was observed while culturing the cells at 37° C., 5% $CO_2$ in an incubator to calculate a TCID$_{50}$ value. The results are shown in the following Table 4.

TABLE 4

Detection of neutralizing antibodies against ZIKV in immunized mice.

| Group | Injection Ag | Adjuvant | TCID$_{50}$/ml MR766 | PRVABC59 | DENV type 2 |
|---|---|---|---|---|---|
| G1 | PBS | — | $10^{2.5}$ | $10^{2.5}$ | $10^{2.5}$ |
| G2 | Zika:Env1 50 μg | Alum 50 μg | $10^{2.0}$ | — | — |
| G3 | Zika:Env 50 μg | Alum 50 μg | $10^{2.5}$ | $10^{1.5}$ | $10^{2.3}$ |
| G4 | Zika:Env1 50 μg | Alum 50 μg + MPL 20 μg | $10^{2.5}$ | — | $10^{2.5}$ |
| G5 | Zika:Env 50 μg | Alum 50 μg + MPL 20 μg | $10^{2.3}$ | $10^{1.5}$ | $10^{2.5}$ |
| G6 | Zika:Env 10 μg | Alum 500 μg + MPL 20 μg | — | $10^{1.5}$ | — |

As a result of the test, infectious virus was detected in the serum obtained 2 days after challenge inoculation with the MR766 strain in all groups except for mice born to mothers of Group 6 (Zika:Env 10 μg+Alum 500 μg+MPL 20 μg). However, by confirming that, in offspring mice born to mothers belonging to Group 2 (Zika:Envl 50 μg+Alum 50 μg) and Group 5 (Zika:Env 50 μg+Alum 50 μg+MPL 20 μg), the amount of virus in blood was reduced to $10^{2}$ and $10^{2.3}$ TCID$_{50}$/ml, respectively, compared to the control ($10^{2.5}$ TCID$_{50}$/ml), it was confirmed that the offspring born to mothers of some vaccine candidate-inoculated groups (Groups 2, 5, and 6) inherited the mother's antibody and exhibited protective ability against the MR766 strain.

Meanwhile, it could be confirmed that among the serum obtained 2 days after challenge inoculation of the PRVABC59 strain in 2-day-old mice born to mothers inoculated with the vaccine candidates and the control group, the amount of virus in blood was measured to be $10^{2.5}$ TCID$_{50}$/ml in offspring mice born to mothers inoculated with PBS, which is the control, and in offspring mice born to mothers belonging to Groups 3, 5, and 6, the amount of virus in blood was decreased to $10^{2}$, $10^{2.3}$ TCID$_{50}$/ml, respectively. Further, since the virus was not detected in blood of the offspring mice born to mothers of Groups 2 and 4, it was confirmed that the offspring born to mothers inoculated with the vaccine candidates inherited the mother's antibody and exhibited protective ability against the PRVABC59 strain.

In order to confirm whether the vaccine candidates (Zika: Envl, Zika:Env) have a cross-protective effect against dengue virus (DENV), DENV was subcutaneously inoculated into two-day-old offspring mice born to mothers who were inoculated 3 times (Day-0, 14, and 42) at $10^6$ $TCID_{50}$/mouse to observe the alleviation of symptoms. It could be confirmed that, in offspring mice born to mothers inoculated with PBS, which is the control, in the serum obtained 2 days after DENV challenge inoculation, the amount of virus in blood was measured to be $10^{2.5}$ $TCID_{50}$/ml, and in offspring mice born to mothers belonging to Group 3, the amount of virus in blood decreased to $10^{2.3}$ $TCID_{50}$/ml. In addition, it was confirmed that offspring mice born to mothers belonging to Groups 2 and 6 showed cross-protective ability against dengue virus when inoculating the vaccine candidate because no virus was detected in the blood.

Synthesis of Comparative Example Results

The results of the comparative examples are synthesized and summarized in the following Table 5. The number means the ranking, and the closer to 1 in the corresponding region, the better the effect.

TABLE 5

| Vaccine efficacy evaluation | | | Vaccine candidate | | | | |
|---|---|---|---|---|---|---|---|
| | | | Zika: Envl (50 μg) Alum (50 μg) | Zika: Env (50 μg) Alum (50 μg) | Zika: Env1 (50 μg) Alum (50 kg) + MPL (20 μg) | Zika: Env (50 μg) Alum (50 μg) + MPL (20 μg) | Zika: Env (50 μg) Alum (500 μg) + MPL (20 μg) |
| Humoral immunity | IgG | | 1 | 1 | 1 | 1 | 1 |
| Neutralizing antibody titer | PRNT | | 4 | 3 | 5 | 2 | 1 |
| Cellular immunity | ELISPOT | IFN-γ | 4 | 3 | 5 | 2 | 1 |
| | | IL-12 | 3 | 2 | 3 | 3 | 1 |
| | ELISA | IFN-γ | 4 | 3 | 4 | 2 | 1 |
| | | IL-12 | 3 | 2 | 3 | 3 | 1 |
| | | TNF-α | — | — | — | — | — |
| | | IL-4 | 2 | 1 | 2 | 2 | 2 |
| Maternal antibody | IgG | | 3 | 2 | 4 | 2 | 1 |
| Maternal cellular immunity | ELISPOT | IFN-γ | 2 | 2. | 2 | 2 | 1 |
| | | IL-12 | 3 | 3 | 3 | 2 | 1 |
| | ELISA | IFN-γ | 4 | 3 | 2 | 5 | 1 |
| | | IL-12 | 3 | 3 | 1 | 2 | 3 |
| | | TNF-α | 2 | 5 | 1 | 4 | 3 |
| Protective efficacy evaluation | Challenge strain | MR766 | 4 | 2 | 5 | 3 | 1 |
| | | PRVABC59 | 3 | 1 | 3 | 5 | 1 |
| | | DENV | 1 | 1 | 5 | 4 | 1 |
| | Sum | | 4 (2.9) | 2 (2.3) | 5 (3.1) | 3 (2.8) | 1 (1.3) |

*Each ranking was prepared based on results after the last inoculation

In summary, humoral immunity, cellular immunity and protective efficacy evaluation tests were performed to evaluate the immunogenicity and efficacy of each vaccine candidate, and first, in the humoral immunity test, it was confirmed that the inoculated antigen-recognizing antibody increased as the number of inoculations increased in all groups compared to the negative control group (PBS; Group 1). However, it was confirmed that the antibody titer was shown to be higher in the group in which MPL was mixed (Groups 4 to 6) compared to other groups when the vaccine candidate is inoculated once.

Subsequently, when the Zika virus-specific IgG subclass in the serum was measured by indirect ELISA, the IgG2c ratio was about 1.6 to 2.5-fold in the group in which MPL was mixed (Groups 4 to 6) when the vaccine candidate was administered once, showing a highTh1-cell-mediated immune response, but the IgG2c/IgG1 ratio was observed to be close to 1 when the vaccine candidate was repeatedly inoculated 2 to 3 times, and in addition, it was confirmed that the group in which only Alum was mixed (Groups 2 to 3) conversely had a high Th2 cell-mediated immune response with an IgG2c/IgG1 ratio of 0.2 to 0.4 when the vaccine candidate was administered once, and the IgG2c/IgG1 ratio was shown to be close to 1 when the vaccine candidate was repeatedly inoculated 2 or 3 times. These results mean that antibody isotype switching is influenced by the adjuvant during the first inoculation of the vaccine, whereas the ratio of Th1/Th2 responses is almost the same during repeated inoculations.

Furthermore, when the neutralizing ability of antibodies against two types of Zika virus (MR766, PRVABC59 strain) and dengue virus (type 2) in serum obtained from mice immunized three times with the vaccine candidates was confirmed by PRNT, the level of induction of neutralizing antibodies against MR766 and PRVABC Zika virus strains was shown to be high in Groups 3, 5 and 6, which are Zika:Env-inoculated groups, and in particular, it could be confirmed that in Group 6, the induction level of neutralizing antibodies against the MR766 strain and PRVABC59 strain was 3200, which was much higher than the other groups.

In the results of the cellular immunity test, unlike the expectation that IFN-γ and IL-12 secreting cells were most likely to be observed in Groups 4 to 6, which are groups in which MPL was mixed as a result of a single inoculation with the vaccine candidates, the highest levels of IFN-γ and IL-12 secreting cells were observed in Group 2 (Zika:Envl 50 μg+Alum 50 μg) in which MPL was not mixed and Group 6 (Zika:Env 10 μg+Alum 500 μg+MPL 20 μg), and in the ELISA results, the highest amounts of IFN-γ and TNF-α secretion were also observed in Groups 2 and 6. In contrast, when the vaccine candidate was inoculated 2 to 3 times, more IFN-γ-secreting cells were observed in Groups 3, 5, and 6, which are Zika:Env-inoculated groups, compared to the Zika:Envl-inoculated groups, and in the ELISA results, the highest amounts of IFN-γ secretion were observed in Groups 3, 5, and 6.

In addition, as a result of analyzing the immune cells activated during vaccine inoculation, the proportion of effector T cells did not show a significant difference between each group during the first and third vaccinations of the vaccine candidates, and the T cell population according to repeated inoculation of the vaccine did not show any change. In light of the results of the previous cellular immunity test, this is thought to be due to an increase in T cell activity when the vaccine candidates are inoculated. As a result of observation of exhausted T cells and regulatory T cells, it was confirmed that the population did not increase during repeated inoculation for all vaccine candidates, and thus effector T cell depletion or activation inhibition did not appear.

As a result of measuring maternal antibodies in the protective efficacy evaluation test, maternal antibodies were confirmed in all groups of offspring mice born from mice inoculated three times with the vaccine candidate, and in particular, it was confirmed that Groups 3, 5 and 6, which are Zika:Env-inoculated groups, showed higher antibody titers than the other groups. In addition, as a result of the maternal cellular immunity test, the highest levels of both IFN-γ secreting cells and secretion amounts were observed in Group 6. Subsequently, as a result of evaluating the protective efficacy by challenge inoculation of offspring mice with two types of Zika viruses (MR766, PRVABC59 strain) and dengue virus (type2), the best protective ability against Zika virus and dengue virus was observed in Group 6.

In conclusion, it was confirmed that the group inoculated with the Zika:Env antigen was better than the Zika:Envl-inoculated group in all the humoral immunity, cellular immunity and protective efficacy evaluations. In particular, when 10 μg of Zika:Env antigen was mixed with 500 μg of Alum+20 μg of MPL, the best vaccine efficacy is exhibited, indicating that even a small amount of antigen can induce significantly improved vaccine efficacy through combination with an adjuvant.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

Since the recombinant Zika virus envelope protein of the present invention can not only be effectively expressed even in plants, but also has high water solubility, and thus is easily isolated and purified, and also acts as an antigen in vivo to exhibit high immunogenicity and virus neutralizing ability, the recombinant Zika virus envelope protein of the present invention can be used as a novel Zika virus vaccine.

Further, since immune cells of mice inoculated with a vaccine composition containing the recombinant Zika virus envelope protein according to the present invention exhibit a specific increase in production of interferon-gamma (IFN-γ), interleukin-12 (IL-12) and tumor necrosis factor-alpha (TNF-α), which are cytokines specific for external stimulating antigens, it was found that the immunoprotective/preventive efficacy against Zika virus infection was enhanced. Therefore, the vaccine composition of the present invention can be usefully used for the prevention of Zika virus infection.

Furthermore, the present invention can verify an expression system with better immune efficacy by referring to the results of directly applying a recombinant Zika virus vaccine composition developed using a plant cell-derived expression system to an animal model, and this facilitates the development of a recombinant Zika virus vaccine applicable to humans, and can simultaneously be used to develop vaccines against other mosquito-borne diseases similar to Zika virus, and thus is expected to have great industrial applicability.

The invention claimed is:

1. A vaccine composition comprising, as active ingredients, a recombinant Zika virus envelope protein comprising an amino acid sequence of SEQ ID NO: 10 or SEQ ID NO: 12; and an adjuvant selected from alum, monophosphoryl lipid A (MPL), or a combination thereof.

2. The vaccine composition of claim 1, wherein the alum is comprised at a ratio of 1:1 to 50 (envelope protein:alum) relative to the weight of the recombinant Zika virus envelope protein.

3. The vaccine composition of claim 1, wherein the MPL is comprised at a ratio of 1:0.4 to 2 (envelope protein:MPL) relative to the weight of the recombinant Zika virus envelope protein.

4. The vaccine composition of claim 1, wherein a combination of the alum and the MPL is comprised at a ratio of 1:1 to 50:0.4 to 2 (envelope protein:alum:MPL) relative to the weight of the recombinant Zika virus envelope protein.

5. The vaccine composition of claim 1, wherein the vaccine composition is inoculated one to three times; and wherein the inoculation is performed at an interval of 14 to 28 days.

6. The vaccine composition of claim 1, wherein the vaccine composition has protective ability against one or more selected from the group consisting of a Zika virus PRVABC59 strain, a Zika virus MR766 strain and dengue virus type-2; or wherein the vaccine composition promotes the secretion of any one or more selected from the group consisting of interferon-gamma (IFN-$\gamma$), interleukin-12 (IL-12), and tumor necrosis factor-alpha (TNF-$\alpha$); or wherein the vaccine composition induces the formation of a maternal antibody.

* * * * *